US010081667B2

(12) United States Patent
Bidwell, III et al.

(10) Patent No.: US 10,081,667 B2
(45) Date of Patent: Sep. 25, 2018

(54) COMPOSITION AND METHOD FOR THERAPEUTIC AGENT DELIVERY DURING PREGNANCY

(71) Applicant: University of Mississippi Medical Center, Jackson, MS (US)

(72) Inventors: Gene L. Bidwell, III, Jackson, MS (US); Eric M. George, Jackson, MS (US)

(73) Assignee: University of Mississippi Medical Center, Jackson, MS (US)

( * ) Notice: Subject to any disclaimer, the term of this patent is extended or adjusted under 35 U.S.C. 154(b) by 0 days.

(21) Appl. No.: 14/917,460

(22) PCT Filed: Oct. 1, 2014

(86) PCT No.: PCT/US2014/058640
§ 371 (c)(1),
(2) Date: Mar. 8, 2016

(87) PCT Pub. No.: WO2015/051001
PCT Pub. Date: Apr. 9, 2015

(65) Prior Publication Data
US 2016/0297868 A1 Oct. 13, 2016

Related U.S. Application Data

(60) Provisional application No. 61/885,300, filed on Oct. 1, 2013.

(51) Int. Cl.
| | |
|---|---|
| *A61K 47/64* | (2017.01) |
| *C07K 14/78* | (2006.01) |
| *A61K 38/18* | (2006.01) |
| *C07K 7/08* | (2006.01) |
| *C07K 14/47* | (2006.01) |
| *C07K 14/49* | (2006.01) |
| *A61K 38/00* | (2006.01) |

(52) U.S. Cl.
CPC ............ *C07K 14/78* (2013.01); *A61K 38/005* (2013.01); *A61K 38/1866* (2013.01); *A61K 47/6435* (2017.08); *C07K 7/08* (2013.01); *C07K 14/4703* (2013.01); *C07K 14/49* (2013.01); *C07K 2319/00* (2013.01); *C07K 2319/33* (2013.01)

(58) Field of Classification Search
None
See application file for complete search history.

(56) References Cited

U.S. PATENT DOCUMENTS

| | | | | |
|---|---|---|---|---|
| 2003/0220262 A1 * | 11/2003 | Schreiner | ........... | A61K 38/1866 514/8.1 |
| 2010/0022455 A1 * | 1/2010 | Chilkoti | ................ | A61K 38/26 514/18.8 |
| 2010/0022466 A1 | 1/2010 | Raucher et al. | | |
| 2011/0110866 A1 | 5/2011 | Chilkoti et al. | | |
| 2012/0213781 A1 | 8/2012 | Hilbert | | |
| 2013/0085099 A1 | 4/2013 | Raucher et al. | | |

FOREIGN PATENT DOCUMENTS

| | | |
|---|---|---|
| WO | WO2008030968 A2 | 3/2008 |
| WO | 20150168321 | 11/2015 |

OTHER PUBLICATIONS

Loibl et al. ('Treatment of breast cancer during pregnancy: an observational study' Lancet Oncology v13 Sep. 2012 pp. 887-896). (Year: 2012).*
McDaniel et al. ('Recursive directional ligation by plasmid reconstruction allows rapid and seamless cloning of oligomeric genes' Biomacromolecules v11 2010 pp. 944-952) (Year: 2010).*
Saint-Ruf et al. ('Causes and consequences of DNA repair activity modulation during stationary phase in *Escherichia coli*' Critical Reviews in Biochemistry and Molecular Biology v42 2007 pp. 259-270) (Year: 2007).*
Erbach ('Neurodegenerative diseases in the workplace' Library of the European Parliament Mar. 7, 2013, 6 pages) (Year: 2013).*
Online article 'Why two thirds of cancer cases are not preventable' (retrieved from https://chewychunks.wordpress.com/2015/01/30/why-two-thirds-of-cancer-cases-are-not-preventable/ on Jun. 30, 2015, 4 pages) (Year: 2015).*
Alberts et al. (Molecular Biology of the Cell. 4th edition, New York: Garland Science; 2002; retrieved from http://www.ncbi.nlm.nih.gov/books/NBK26917/ on Mar. 2, 2015, 10 pages) (Year: 2015).*
George, EM et al. Delivery of an Anti-Inflammatory Nf-kappaB Inhibitory Polypeptide to Treat Preeclampsia. Hypertension. Sep. 2013; vol. 62, No. 3; AS; abstract.
Bidwell, III, GL. Peptides for Cancer Therapy: A Drug Development Opportunity and a Drug Delivery Challenge. Therapeutic Delivery. May 2012, vol. 3, No. 5, pp. 609-621.
George, et al., "Development of a Stabilized Bioactive VEGF Chimera for the Management of Preeclampsia", Hypertension, Lippincott Williams & Wilkins, US, vol. 62, No. 3, Suppl, Sep. 1, 2013 (Sep. 1, 2013).
Bidwell, et al., "A delivery system for protein and peptide-based therapeutics to treat preeclampsia", The FASEB Journal, Federation of American Societies for Experimental Biology, US, vol. 27, Apr. 1, 2013.

(Continued)

*Primary Examiner* — Karlheinz R. Skowronek
*Assistant Examiner* — Ronald T Niebauer
(74) *Attorney, Agent, or Firm* — Stites & Harbison PLLC; Mandy Wilson Decker

(57) ABSTRACT

A composition including an elastin-like polypeptide (ELP) coupled to a therapeutic agent is provided. The ELP comprises at least about 5 repeats of the amino acid sequence VPGXG. Further provided is a method of using the composition for therapeutic agent delivery during pregnancy to reduce the amount of the therapeutic agent crossing a placenta in a pregnant subject. The method includes administering to the pregnant subject an effective amount of the composition comprising the ELP coupled to the therapeutic agent.

20 Claims, 20 Drawing Sheets
Specification includes a Sequence Listing.

(56) References Cited

OTHER PUBLICATIONS

Massodi, et al., "Inhibition of ovarian cancer cell proliferation by a cell cycle inhibitory peptide fused to a thermally responsive polypeptide carrier", International Journal of Cancer, vol. 126, No. 2, Jan. 15, 2010 (Jan. 15, 2010), pp. 533-544.

Massodi, et al., "Evaluation of cell penetrating peptides fused to elastin-like polypeptide for drug delivery", Journal of controlled Release, vol. 108, No. 2 , pp. 396-408, 2005.

Bidwell, et al., "Cell penetrating elastin-like polypeptides for therapeutic peptide delivery", Advanced Drug Delivery Reviews, Elsevier, Amsterdam, NL, vol. 62, No. 15,Dec. 30, 2010 (Dec. 30, 2010), pp. 1486-1496.

Lyons, et al., "Structural and Hydrodynamic Analysis of a Novel Drug Delivery Vector: ELP[V5G3A2-150]", Biophysical Journal, vol. 104, No. 9, May 1, 2013 (May 1, 2013 ), pp. 2009-2021.

Chilkoti, et al., "Design of thermally responsive, recombinant polypeptide carriers for targeted drug delivery", Advanced Drug Delivery Reviews, Elsevier, Amsterdam, NL, vol. 54, No. 8, Oct. 18, 2002 (Oct. 18, 2002), pp. 1093-1111.

\* cited by examiner

US 10,081,667 B2

COMPOSITION AND METHOD FOR THERAPEUTIC AGENT DELIVERY DURING PREGNANCY

STATEMENT OF GOVERNMENT SUPPORT

This presently-disclosed subject matter was made with government support under grant number NIH R01HL121527 awarded by National Institutes of Health. The government has certain rights in it.

RELATED APPLICATIONS

This application claims priority from U.S. Provisional application Ser. No. 61/885,300, filed Oct. 1, 2013, the entire disclosure of which is incorporated herein by this reference.

TECHNICAL FIELD

The presently-disclosed subject matter relates to a composition and method for therapeutic agent delivery during pregnancy. More particularly, the presently-disclosed subject matter relates to a composition comprising an elastin-like polypeptide (ELP) coupled to a therapeutic agent and a method of using the composition to reduce an amount of the therapeutic agent crossing the placenta in a pregnant subject.

INTRODUCTION

Special considerations must be taken when giving drug therapies to pregnant mothers. Not only must normal concerns of maximizing efficacy while reducing side effects in such subjects be considered, but the effects of the therapeutic agent on the developing fetus must also be taken into account. Many therapeutic agents that are otherwise safe for an adult will cross the placental barrier in pregnant mothers and cause severe adverse effects on the developing fetus. Therefore, compositions and methods that reduce the amount of therapeutic agents crossing the placenta in a pregnant subject and which can be used to treat various diseases and disorders during pregnancy are both highly desirable and beneficial.

SUMMARY

This summary describes several embodiments of the presently-disclosed subject matter, and, in many cases, lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes a composition comprising an elastin-like polypeptide (ELP) coupled to a therapeutic agent and a method of delivering the composition to a pregnant subject. More particularly, the presently-disclosed subject matter relates to a method of using the composition to reduce the amount of the therapeutic agent crossing the placenta in the pregnant subject.

In some embodiments of the presently-disclosed subject matter, a method of delivering a therapeutic agent in a pregnant subject is provided. In some embodiments, the method includes administering to the pregnant subject an effective amount of a composition comprising an ELP coupled to a therapeutic agent. In some embodiments, the ELP sequence comprises at least about 5 repeats of the amino acid sequence VPGXG (SEQ ID NO: 1). In some embodiments, the composition reduces the amount of the therapeutic agent crossing the placenta in the pregnant subject. In some embodiments, the ELP sequences comprises about 5 repeats to about 160 repeats of the amino acid sequence VPGXG (SEQ ID NO: 1), and X in the sequence VPGXG (SEQ ID NO: 1) is any amino acid except proline. In some embodiments, the X in the amino acid sequence VPGXG (SEQ ID NO: 1) is Val, Ala, and Gly in a ratio of about 1:4-8:3-7. In some embodiments, the ELP comprises about 32 repeats of the amino acid sequence VPGXG (SEQ ID NO: 1) where X is Val, Ala, and Gly in a 1:8:7 ratio. A non-limiting example of the ELP amino acid sequence comprises SEQ ID NO: 2. In some embodiments, the ELP comprises about 80 repeats of the amino acid sequence VPGXG (SEQ ID NO: 1), where X is Val, Ala, and Gly in a 1:8:7 ratio. A non-limiting example of this ELP comprises the amino acid sequence of SEQ ID NO: 3. In some embodiments, the ELP comprises about 160 repeats of the amino acid sequence VPGXG (SEQ ID NO: 1), where X is Val, Ala, and Gly in a 1:8:7 ratio. One non-limiting example of the ELP comprises the amino acid sequence of SEQ ID NO: 4. In some embodiments, the ELP comprises about 40 repeats of the amino acid sequence VPGXG (SEQ ID NO: 1), where X is Gly. One non-limiting example of the ELP comprises the amino acid sequence of SEQ ID NO: 5. In some embodiments, the ELP comprises about 80 repeats of the amino acid sequence VPGXG (SEQ ID NO: 1), where X is Gly. One non-limiting example of the ELP comprises the amino acid sequence of SEQ ID NO: 6. In some embodiments, the ELP comprises about 160 repeats of the amino acid sequence VPGXG (SEQ ID NO: 1), and wherein X is Gly. One non-limiting example of the ELP comprises the amino acid sequence SEQ ID NO: 7. In some embodiments, the ELP comprises about 32 repeats of the amino acid sequence VPGXG (SEQ ID NO: 1), where X is Val, Ala, or Gly in a 1:4:3 ratio. One non-limiting example of the ELP comprises the amino acid sequence of SEQ ID NO: 8. In some embodiments, the ELP comprises about 80 repeats of the amino acid sequence VPGXG (SEQ ID NO: 1), and wherein X is Val, Ala, or Gly in a 1:4:3 ratio. Non-limiting example of the ELP comprises the amino acid sequence of SEQ ID NO: 9. In some embodiments, the ELP comprises about 160 repeats of the amino acid sequence VPGXG (SEQ ID NO: 1), where X is Val, Ala, or Gly in a 1:4:3 ratio. Non-limiting example of the ELP comprises the amino acid sequence of SEQ ID NO: 10. In some embodiments, the ELP comprises about 40 repeats of the amino acid sequence VPGXG (SEQ ID NO: 1), where X is Lys. One non-limiting example of the ELP comprises the amino acid sequence of SEQ ID NO: 11. In some embodiments, the ELP comprises about 80 repeats of the amino acid sequence VPGXG (SEQ ID NO: 1), where X is Lys. One non-limiting example of the ELP comprises the amino acid sequence of SEQ ID NO: 12. In some embodiments, the ELP comprises about 160 repeats of the amino acid sequence VPGXG (SEQ ID NO: 1), where X is Lys. One non-limiting example of the ELP comprises the amino acid sequence of SEQ ID NO: 13.

In some embodiments, the composition further comprises a cell-penetrating peptide coupled to the ELP. Non-limiting examples of the cell-penetrating peptide are penetratin, Tat, SynB1, Bac, polyArg, MTS, Transportan, or pVEC. In some embodiments, the composition further comprises an organ targeting peptide coupled to the ELP. Non-limiting examples of organ targeting peptide are kidney targeting peptide, a placenta targeting peptide, or a brain targeting peptide.

In some embodiments of the presently-disclosed subject matter, the therapeutic agent is selected from a peptide, an antibiotic, or a small molecule drug. In some embodiments, the therapeutic agent a peptide where the peptide is VEGF. In some embodiments, VEGF includes $VEGF_{121}$, $VEGF_{165}$, $VEGF_{189}$, $VEGF_{206}$, VEGF-A, VEGF-B, VEGF-C, VEGF-D, VEGF-E, or PIGF. A non-limiting example of the compositing comprises the amino acid sequence of SEQ ID NO: 14. In some embodiments, the therapeutic agent is a peptide, where the peptide is an NF-κB inhibitor peptide. A non-limiting example of the composition comprises the amino acid sequence of SEQ ID NO: 15. In some embodiments, the therapeutic agent is a peptide where the peptide is an NADPH oxidase inhibitory peptide. One non-limiting example of the composition comprises the amino acid sequence of SEQ ID NO: 16.

In some embodiments, the therapeutic agent is a small molecule drug that causes adverse events during pregnancy. In some embodiments, the small molecule drug is an anti-hypertensive agent, an anti-epileptic agent, an anti-emetic agent, or a cancer chemotherapeutic agent.

In some embodiments of the presently-disclosed subject matter, the therapeutic agent is for the treatment of preeclampsia, eclampsia, myocardial infarction, renovascular disease, spinocerebellar ataxia, lupus, rheumatoid arthritis, psoriatic arthritis, multiple sclerosis, cancer, Crohn's disease, ankylosing spondylitis, cardiac hypertrophy, plaque psoriasis, hypertension, atherosclerosis, stroke, kidney stones, Alzheimer's disease and other neurodegenerative disorders, prevention of allograft rejection, hepatic fibrosis, schizophrenia, muscular dystrophy, macular degeneration, pulmonary edema, chronic pulmonary hypertension, or disorders where reactive oxygen species are deleterious.

Further provided, in some embodiments of the presently-disclosed subject matter, is a method of treating a disease or disorder in a pregnant subject. In some embodiments, the method includes administering to the pregnant subject an effective amount of a composition comprising an elastin-like polypeptide coupled to a therapeutic agent. In some embodiments, the ELP includes at least 5 repeats of the amino acid sequence VPGXG (SEQ ID NO: 1).

In some embodiments of the presently-disclosed subject matter, a composition is provided that comprises an elastin-like polypeptide coupled to a therapeutic agent. In some embodiments, non-limiting examples of the therapeutic agent are VEGF, an NF-κB inhibitory peptide, and an NADPH oxidase inhibitory peptide.

Advantages of the presently-disclosed subject matter will become evident to those of ordinary skill in the art after a study of the description, Figures, and non-limiting Examples in this document.

BRIEF DESCRIPTION OF THE DRAWINGS

FIG. 2A. The ELP drug carrier was labeled with AlexalFluor633 and infused into normal pregnant Sprague Dawley rats by IV injection (100 mg/kg). 4 h after injection, ex vivo images of placentas, pups, and major organs were collected using an IVIS Spectrum. FIG. 2B. Fluorescence intensity was quantified in all tissues. Error bars represent the standard deviation of 3 rats.

FIG. 3A. After IV administration of fluorescently-labeled polypeptides or saline control, placentas, pups, and major organs were removed and imaged ex vivo using an IVIS Spectrum. Polypeptide deposition in placentas and pups is shown. FIG. 3B. Fluorescence levels in placentas, pups, and major organs was quantified using Living Image software. Error bars represent the standard deviation of four rats per treatment group. FIG. 3C. Frozen sections of intact placentas and pups were cut, stained with the actin-specific rhodamine-phalloidin to allow visualization of the placenta and pups, and scanned using a florescence slide scanner. FIG. 3D. The same slides were imaged using a florescence microscope to visualize the cellular localization of the polypeptides in the placenta (100× magnification).

FIG. 4A. Rhodamine-labeled ELP and SynB1-ELP were incubated in plasma from pregnant rats for the indicated time at 37° C. Percentage of dye release is shown for an average of two experiments, bars indicate s.d. In vivo protein stability was determined by SDS-PAGE analysis of plasma samples from the pharmacokinetic experiment (FIG. 4B-4E). A representative gel from one animal in each group (FIG. 4B, ELP; FIG. 4D, SynB1-ELP) is shown. The numbers indicate time points, and the final lane was loaded with 10 mg of the injected protein as a loading control. The total band intensity and %<50 kDa (FIG. 4C, ELP; FIG. 4E, SynB1-ELP) are shown for an average of four animals per group, bars indicate s.d.

FIG. 5A. Representative images from each animal were collected with identical scan settings. FIG. 5B. Data from all slide scans were quantified relative to fluorescence standards made from the injected protein cut to the same thickness. *Statistically significant as determined by a t-test ($p<0.05$). **Levels were not detectable over autofluorescence.

FIG. 7A. Rhodamine-labeled ELP or SynB1-ELP was administered chronically by IP minipump from GD14-GD19. Plasma was sampled throughout the experiment, and polypeptide levels were determined relative to standards of the injected protein. Data represent the mean±s.d. of four rats per group. FIG. 7B. Ex vivo fluorescence imaging of eight pups and corresponding placentas from one rat from each group is shown. FIG.

7C. Fluorescence intensities were quantified, corrected for autofluorescence, and fit to standards of the injected proteins. Data represent the mean±s.e. of eight placentas and eight pups per rat and four rats per group. *Statistically significant as determined by a two-way ANOVA with post-hoc Bonferroni multiple comparisons (p<0.05). **Levels were not detectable over autofluorescence.

Figure 8:
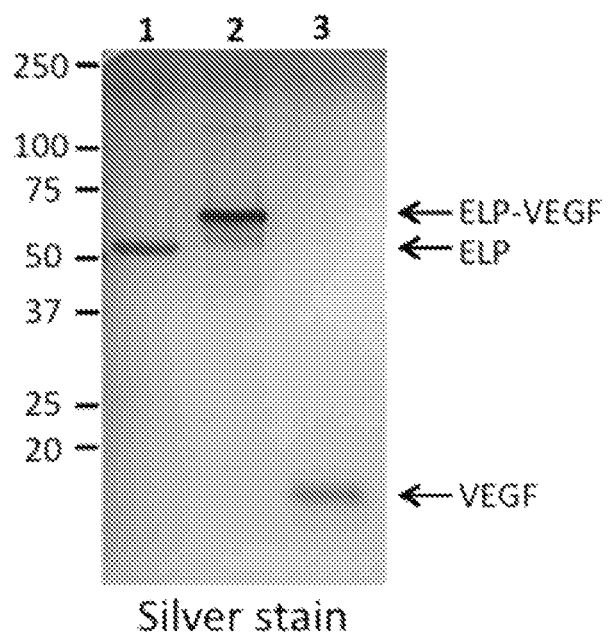

FIG. 8 is an image of a gel showing the purification of ELP-VEGF. SDS-PAGE gel with silver staining demonstrates the purity of ELP-VEGF and ELP control polypeptides. Lane 1, ELP; Lane 2, ELP-VEGF$_{121}$; Lane 3, VEGF$_{121}$.

Figure 9:
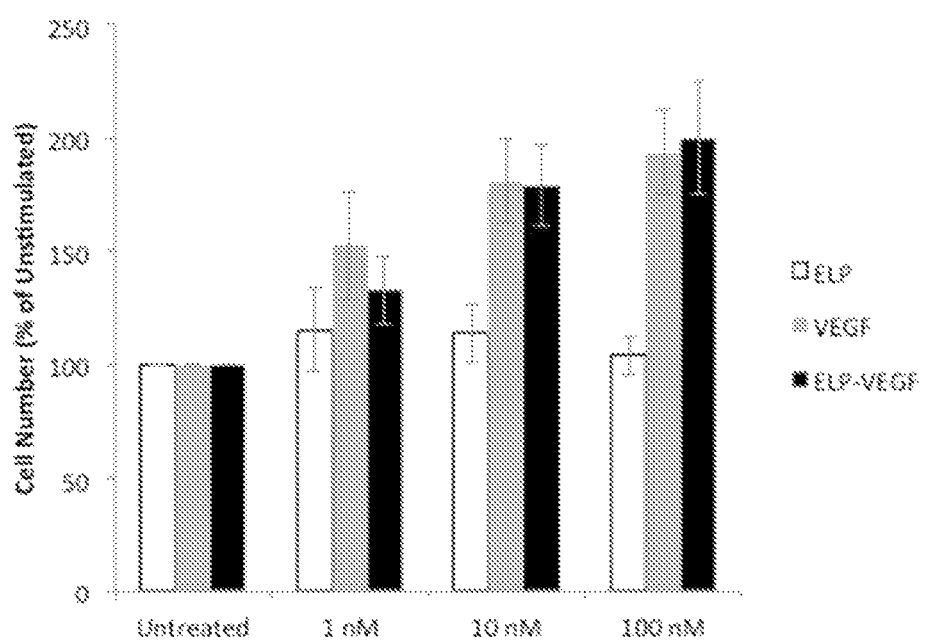

FIG. 9 is a bar graph showing ELP-VEGF stimulation of HUVEC proliferation. HUVEC cell proliferation was determined after 72 h exposure to ELP, VEGF, or ELP-VEGF at the indicated concentrations using the MTS cell proliferation assay.

Figure 10:
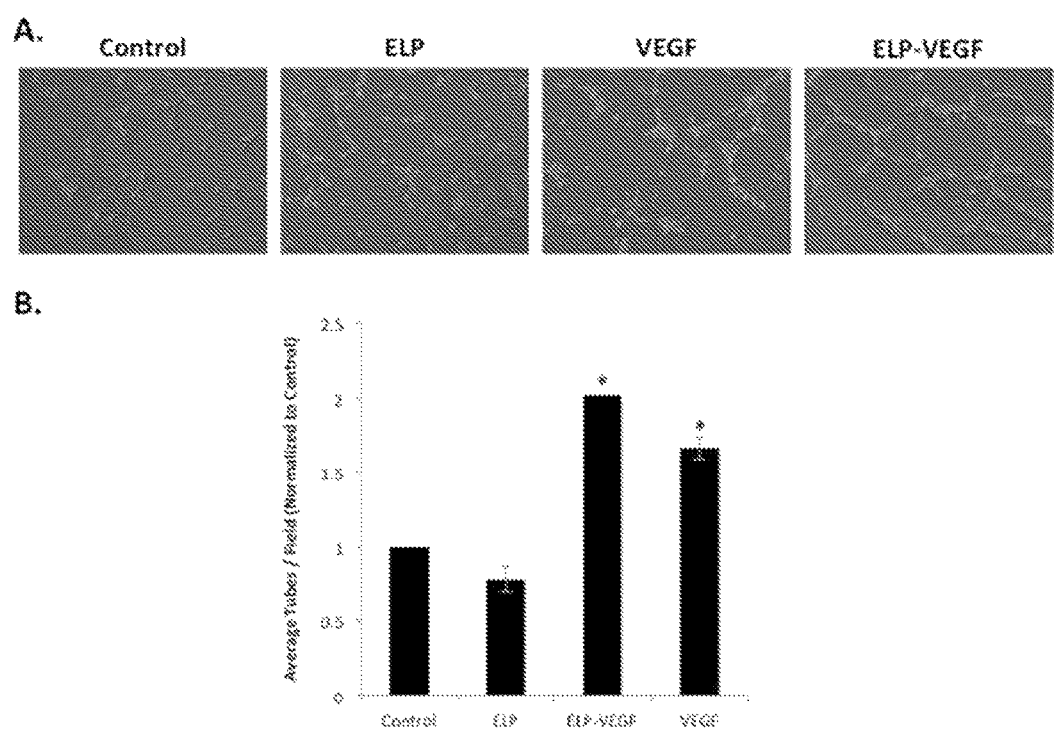

FIG. 10 is a series of images and a bar graph showing ELP-VEGF stimulation of tube formation in HUVECs. FIG. 10A. HUVEC tube formation was assessed 6 h after seeding on growth factor reduced Matrigel and supplementing the media with 20 nM ELP, VEGF, or ELP-VEGF. FIG. 10B. Average tubes per field were counted for six fields per sample. Data represent the mean±se of four independent experiments. *p<0.01, one way ANOVA with post-hoc Bonferonni multiple comparison.

Figure 11:
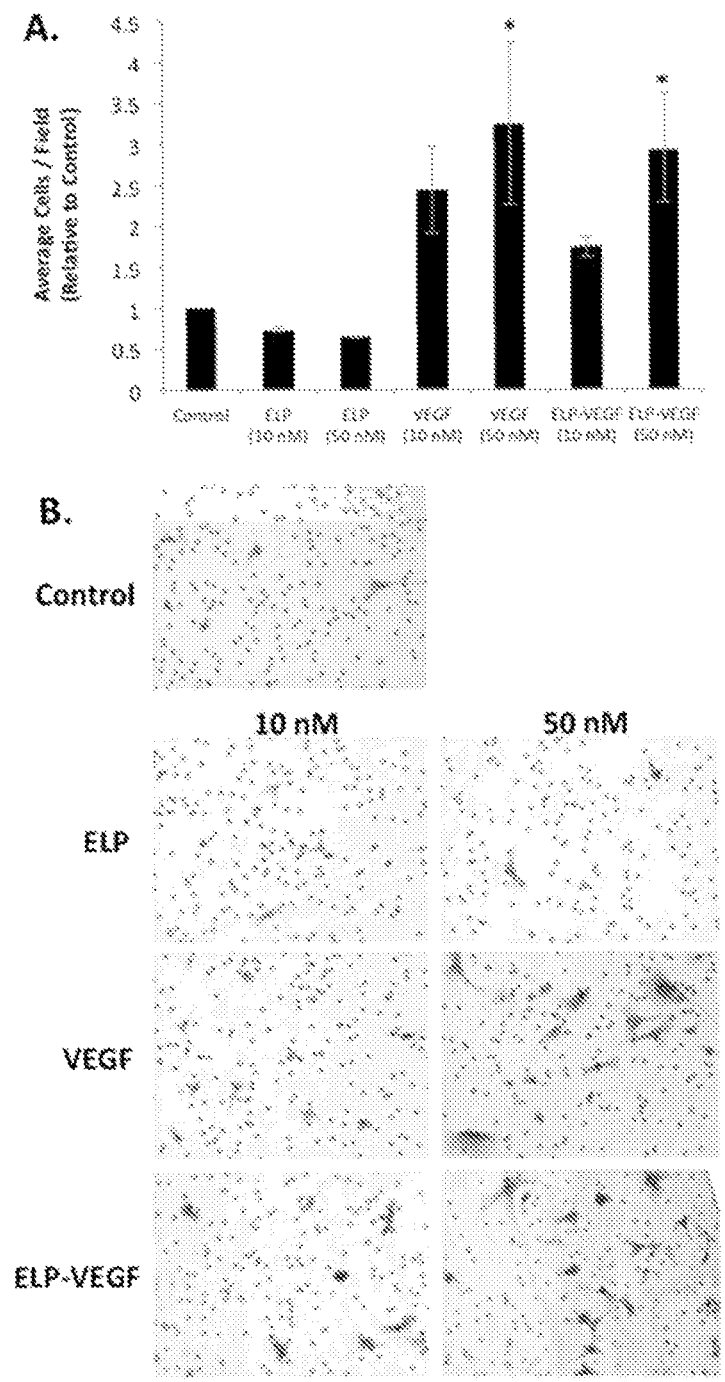

FIG. 11 is a bar graph and a series of images illustrating the ELP-VEGF stimulation of HUVEC migration. FIG. 11A. HUVEC migration was assessed 16 h after seeding in the top chamber of Matrigel-coated Boyden chambers in minimal media and supplementing the bottom chamber with minimal media plus ELP, VEGF, or ELP-VEGF at the indicated concentrations. FIG. 11B. Average cells per field were counted for four to seven fields per sample. Data represent the mean±se of three independent experiments. *p<0.01, one way ANOVA with post-hoc Bonferonni multiple comparison.

Figure 12:
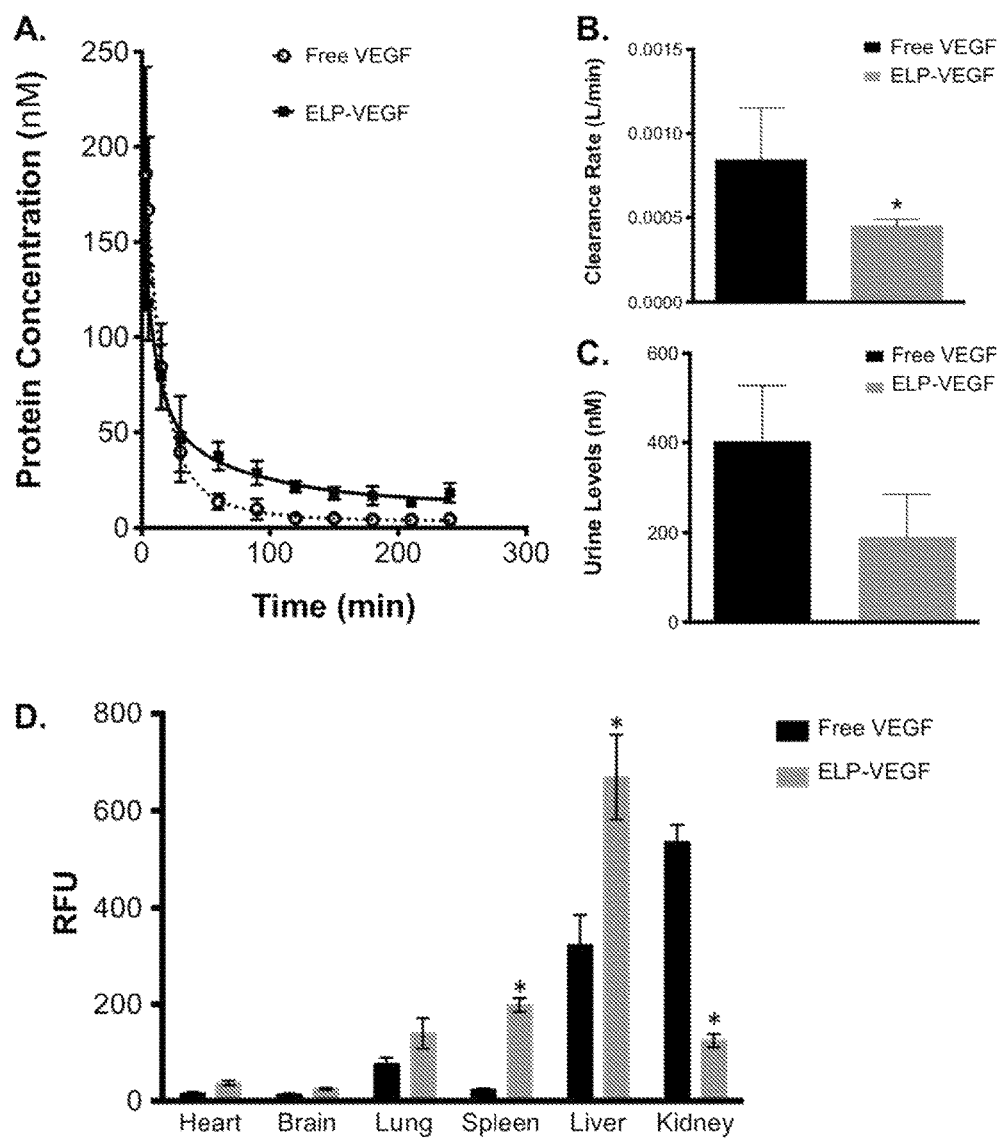

FIG. 12 includes graphs showing ELP-VEGF pharmacokinetics and biodistribution. FIG. 12A. Fluorescently labeled free VEGF or ELP-VEGF were administered by IV injection to C57/Bl6 mice. Plasma levels were determined by direct fluorescence quantitation and fit to a two-compartment pharmacokinetic model. FIG. 12B. ELP-VEGF had a significantly lower plasma clearance rate than free VEGF, as was evidenced by lower levels in the urine at the end of the experiment (FIG. 12C) Data represent the mean±sd of four mice per group. *p<0.01, Student's t-test. FIG. 12D. ELP fusion significantly altered the biodistribution of VEGF, increasing its levels in the spleen and liver and reducing its levels in the kidney. *p<0.01, one way ANOVA with post-hoc Bonferroni multiple comparison.

Figure 13:
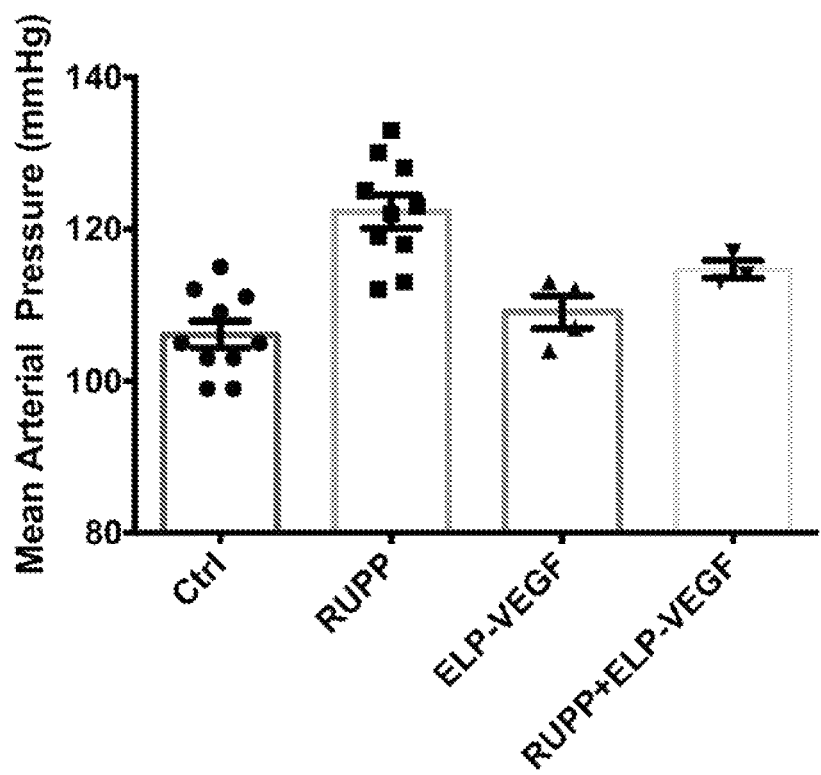

FIG. 13 is a bar graph showing effect of ELP-VEGF on blood pressure in the reduced uterine perfusion model. A study was conducted in pregnant rats subjected to surgical reduction of uterine blood flow (RUPP) on gestational day 14 (GD14). ELP-VEGF or saline control was administered by continuous infusion via IP minipump from GD14 to GD19 at a dose of 1 mg/kg/day. Data represent the mean arterial pressure as assessed by indwelling carotid catheters on GD19. Individual animal data are indicated by the points.

Figure 14:
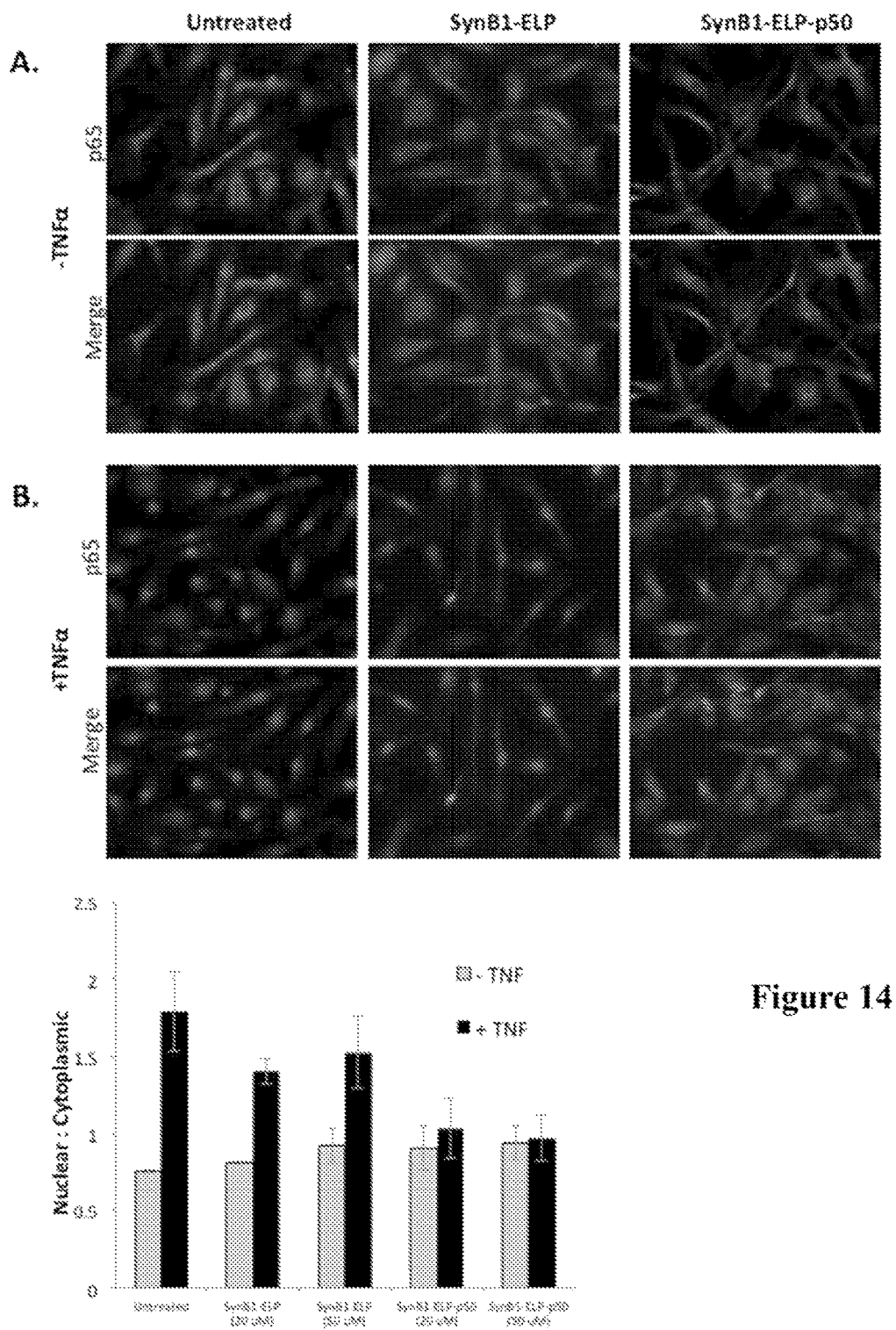

FIG. 14 includes images and a bar graph illustrating inhibition of NF-κB activation with an ELP-delivered p50 peptide. FIG. 14A. Localization of NF-κB in HUVEC cells before and after TNFα stimulation. HUVECs were treated with SynB1-ELP control or SynB1-ELP-p50 (20 μM) for 24 h. Cells were then stimulated for 1 h with TNFα, and NF-κB localization was determined by immunostaining for the p65 subunit (green) and for nuclei with DAPI (blue). FIG. 14B. The nuclear cytoplasmic ratio of NF-κB staining was determined under each treatment condition. Data represent the mean of 30-60 cells per treatment and are averaged over three experiments.

Figure 15:
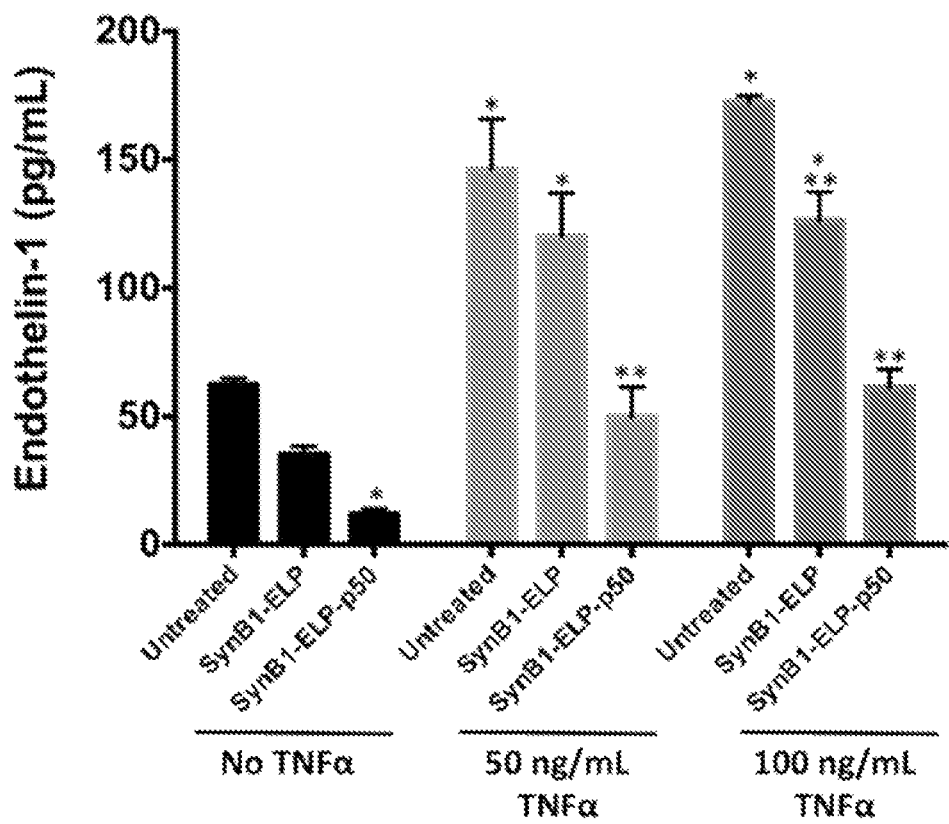

FIG. 15 includes a graph illustrating the inhibition of endothelin release by SynB1-ELP-p50. HUVECs growing in 24-well plates were treated with 50 μM SynB1-ELP or SynB1-ELP-p50 overnight, then 50 or 100 ng/mL was added. Cells were incubated overnight, and culture media was collected and frozen. Endothelin-1 concentration was determined by ELISA. *Levels are significantly different from untreated HUVECs. **Levels are significantly reduced relative to TNFα treatment only (p<0.01, one way ANOVA with post-hoc Bonferonni multiple comparison).

Figure 16:
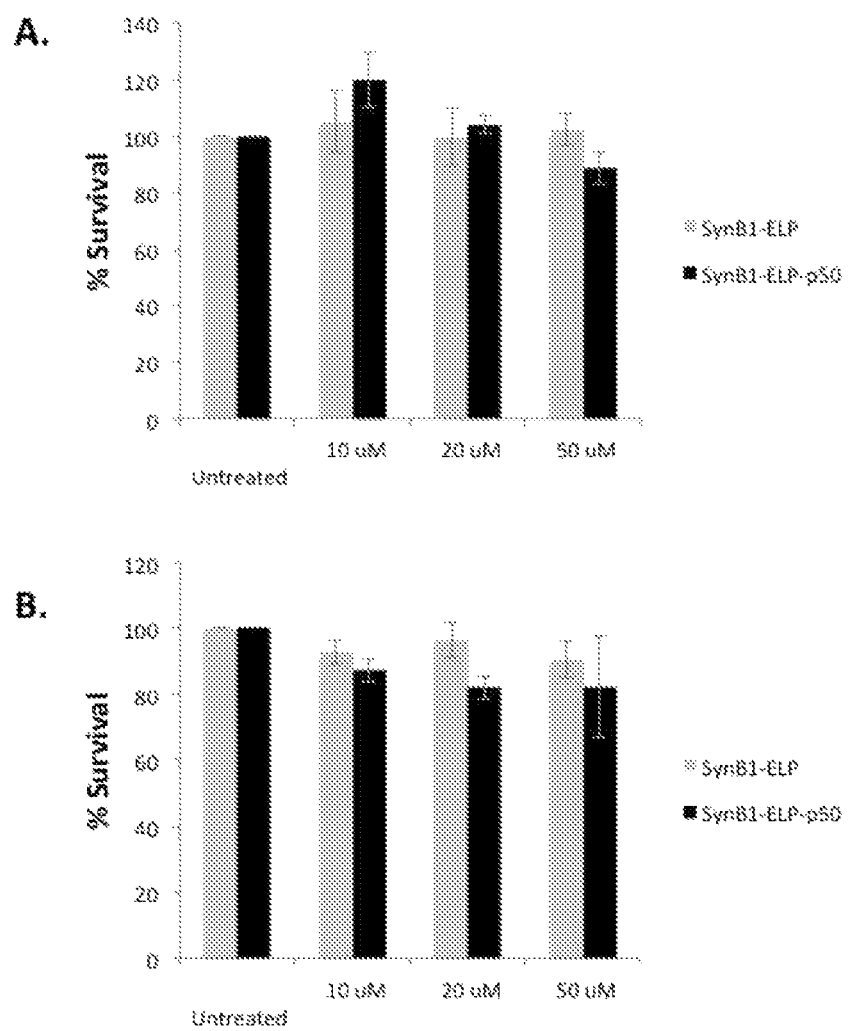

FIG. 16 includes graphs illustrating that the ELP-delivered NF-κB inhibitory peptide is not toxic to cells. HUVEC endothelial cells (FIG. 16A.) and BeWo chorionic cells (FIG. 16B.) were exposed to the indicated concentration of SynB1-ELP or SynB1-ELP-p50 for 72 h. Cell number was determined by MTS assay. Bars represent the standard error of the mean of five independent experiments.

Figure 17:
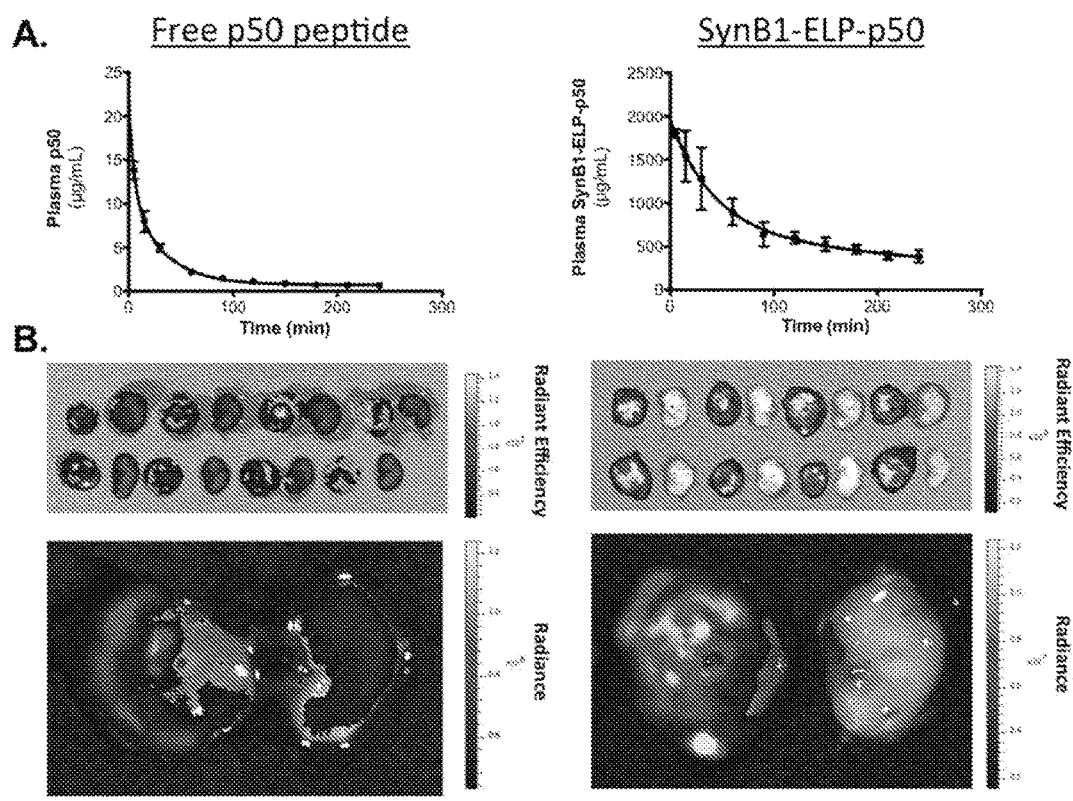

FIG. 17 includes graphs and images illustrating pharmacokinetics and biodistribution of the ELP-delivered p50 peptide. Free p50 peptide (10 amino acids) was synthesized with an N-terminal rhodamine label. Also, the SynB1-ELP-fused p50 peptide was purified and labeled with rhodamine. Each agent was administered by IV injection into pregnant rats at GD14. Plasma was sampled over time (FIG. 17A.), and peptide levels were determined by quantitative fluorescence analysis. Four hours after injection, placenta and pup levels were determined by ex vivo whole organ fluorescence imaging (FIG. 17B).

Figure 18:
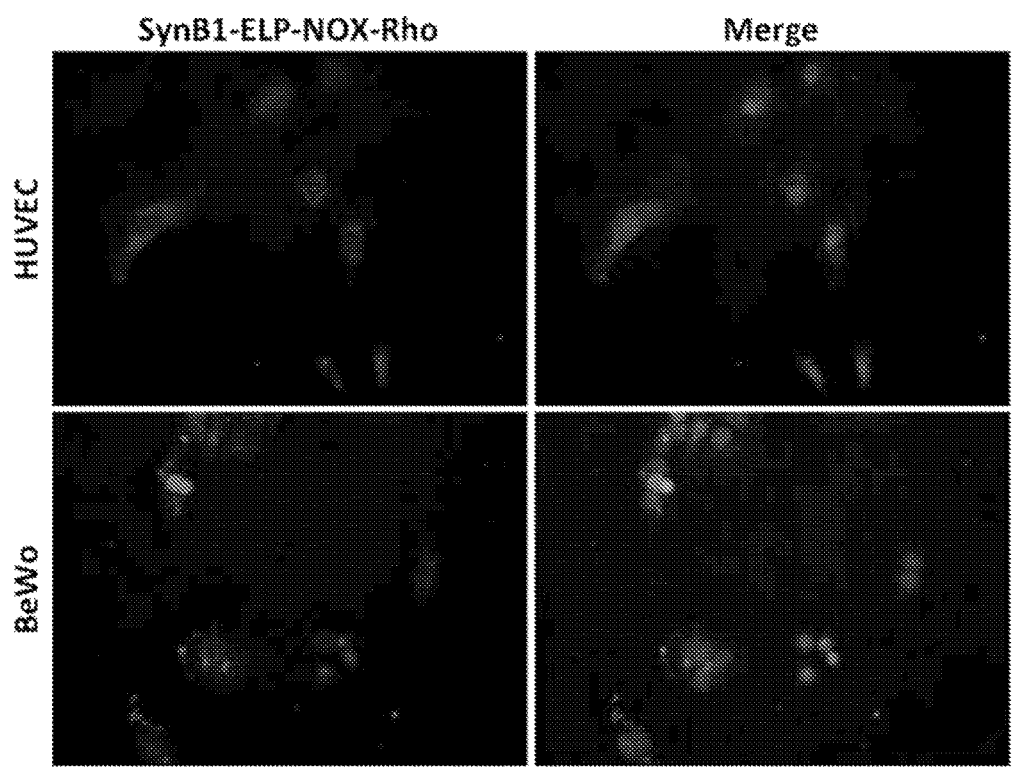

FIG. 18 includes images showing the cellular internalization of SynB1-ELP delivered NOX peptide. Rhodamine-labeled SynB1-ELP-NOX was exposed to cells for 1 h, cells were washed, fresh media was returned, and images were collected 24 h after initial exposure.

Figure 19:
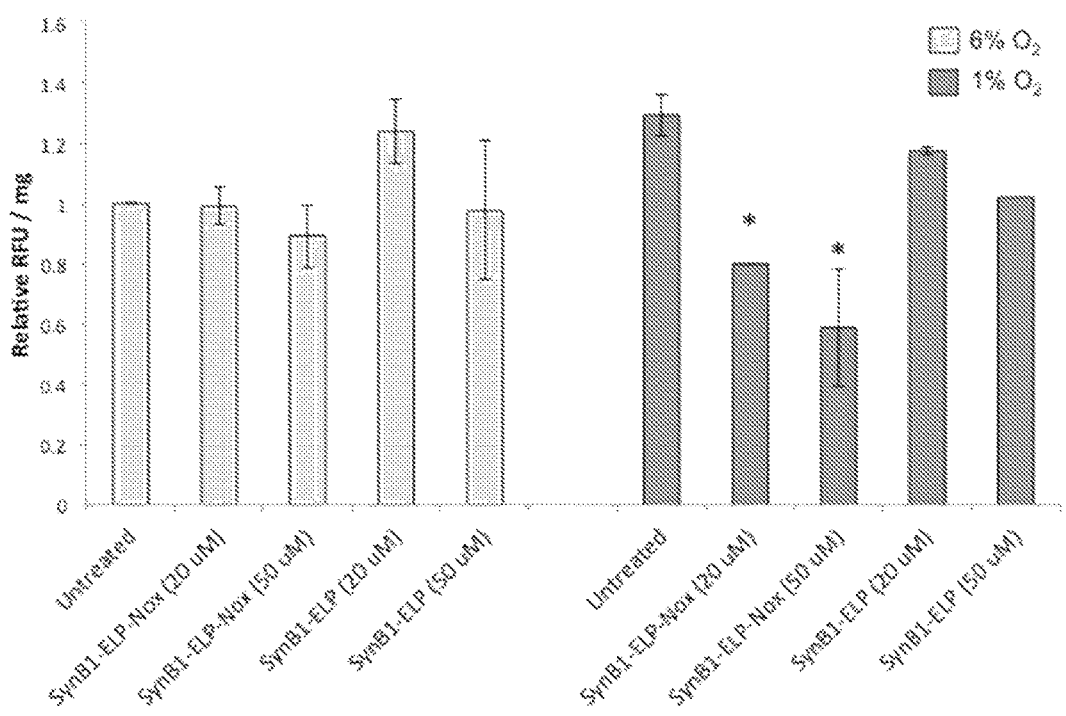

FIG. 19 includes a graph showing inhibition of reactive oxygen species production of placental villous explants. Villous explants were dissected from rat placentas at day 19 of gestation. Explants were grown ex vivo on a bed of Matrigel in cell culture medium. 24 h after equilibration of explants, media was replaced with media plus SynB1-ELP or SynB1-ELP-NOX, and explants were incubated at 37° C. in a 6% or 1% $O_2$ environment for 48 h. ROS was detected by incubation with 5 μM dihydroethdium for 1 hour, and fluorescence was measured using a florescence plate reader. The assay was performed in triplicate, and data represent the mean±s.e. of three independent experiments each performed with 4 explants per treatment group. *p<0.01, one way ANOVA with post-hoc Bonferonni multiple comparison.

Figure 20:
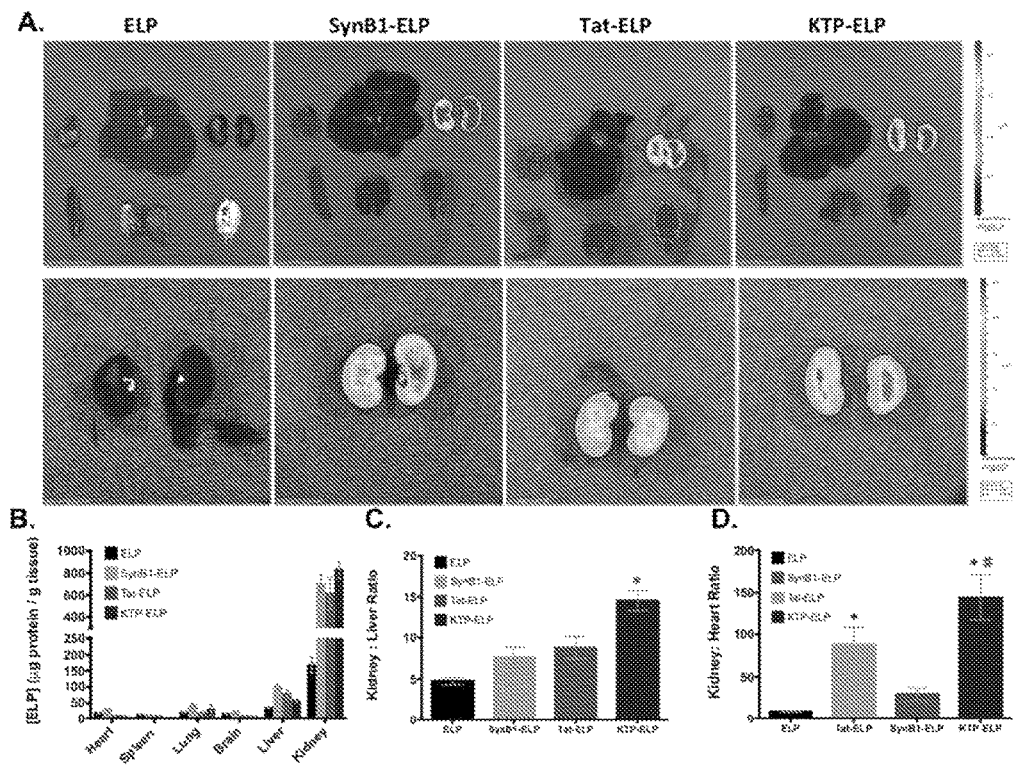

FIG. 20 includes images and bar graphs illustrating enhancement of kidney specificity using kidney targeting peptides. Rats were administered fluorescently labeled ELP, SynB1-ELP, Tat-ELP, or KTP-ELP, and organ biodistribution was determined by ex vivo fluorescence imaging (FIG. 20A). Quantitative analysis showed that the highest accumulation of all peptides was in the kidney, and the targeting agents significantly increased kidney deposition (FIG. 20B.). KTP-ELP had the highest specificity for the kidney as assessed by kidney:liver and kidney:heart ratios (FIG. 20C and FIG. 20D).

BRIEF DESCRIPTION OF THE SEQUENCE LISTING

SEQ ID NO: 1 is a ELP amino acid sequence VPGXG, where X can be any amino acid except proline.

SEQ ID NO: 2 is a ELP sequence of 32 repeats of the amino acid sequence VPGXG, where X is Val, Ala, and Gly in a 1:8:7 ratio SEQ ID NO: 3 is a ELP sequence of 80 repeats of the amino acid sequence VPGXG, where X is Val, Ala, and Gly in a 1:8:7 ratio.

SEQ ID NO: 4 is a ELP sequence of 160 repeats of the amino acid sequence VPGXG, where X is Val, Ala, and Gly in a 1:8:7 ratio.

SEQ ID NO: 5 is a ELP sequence of 40 repeats of the amino acid sequence VPGXG, where X is Gly.

SEQ ID NO: 6 is a ELP sequence of 80 repeats of the amino acid sequence VPGXG, where X is Gly.

SEQ ID NO: 7 is a ELP sequence of 160 repeats of the amino acid sequence VPGXG, where X is Gly.

SEQ ID NO: 8 is a ELP sequence of 32 repeats of the amino acid sequence VPGXG, where X is Val, Ala, or Gly in a 1:4:3 ratio.

SEQ ID NO: 9 is a ELP sequence of 80 repeats of the amino acid sequence VPGXG, where X is Val, Ala, or Gly in a 1:4:3 ratio.

SEQ ID NO: 10 is a ELP sequence of 160 repeats of the amino acid sequence VPGXG, where X is Val, Ala, or Gly in a 1:4:3 ratio.

SEQ ID NO: 11 is a ELP sequence of 40 repeats of the amino acid sequence VPGXG, where X is Lys.

SEQ ID NO: 12 of a ELP sequence of 80 repeats of the amino acid sequence VPGXG, where X is Lys.

SEQ ID NO: 13 is a ELP sequence of 160 repeats of the amino acid sequence VPGXG, where X is Lys.

SEQ ID NO: 14 is a ELP-VEGF amino acid sequence, where a ELP sequence (SEQ ID NO: 4) fused to a C-terminal VEGF121 sequence.

SEQ ID NO: 15 is a SynB1-ELP-p50 amino acid sequence, where a SynB1 peptide fused to N-terminus of a ELP sequence (SEQ ID NO: 4), and a p50 peptide sequence fused to the C-terminus of the ELP sequence.

SEQ ID NO: 16 is a SynB1-ELP-NOX amino acid sequence, where a SynB1 peptide sequence fused to the N-terminus of a ELP sequence (SEQ ID NO: 4), and NOX peptide fused to the C-terminus of the ELP sequence.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. Further, while the terms used herein are believed to be well-understood by one of ordinary skill in the art, definitions are set forth to facilitate explanation of the presently-disclosed subject matter.

Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. Unless otherwise indicated or apparent, the references to the GENBANK® database are references to the most recent version of the database as of the filing date of this Application.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

The presently-disclosed subject matter relates to compositions and methods for therapeutic agent delivery during pregnancy. More particularly, the presently-disclosed subject matter relates to a composition comprising an elastin-like polypeptide (ELP) coupled to a therapeutic agent, and a method of using the composition to reduce the amount of the therapeutic agent crossing the placenta in a pregnant subject.

As used herein, the term "elastin-like polypeptide" or "ELP" refers to a synthetic protein containing structural peptide units, which may be repeating units, structurally related to, or derived from, sequences of the elastin protein, ELP is a macromolecular carrier that has several advantages. It is an inert and biodegradable macromolecule, giving it a good pharmacokinetic profile and very low immunogenicity. Also, as opposed to chemically synthesized polymers, ELP is expressed in and easily purified from *E. coli*. Further, the sequence of a particular ELP can be controlled such that it is possible to generate chimeras of ELP fused to therapeutic proteins or peptides or to add reactive sites for attachment of therapeutic agents. Such ELP chimeras provide certain therapeutic advantages to the therapeutic agent, such as comparatively better stability, solubility, bioavailability, half-life, persistence, and/or biological action of the therapeutic proteinaceous component or attached small molecule drug.

It has now been determined, that ELP does not cross the placenta, and that it can be used as a carrier for therapeutic peptides, antibiotics, and small molecule drugs in a manner that allows pregnant mothers to be treated with a therapeutic agent, while the amount of therapeutic agent crossing the placenta is reduced to thereby protect the developing fetus from damage by the therapeutic agent. Thus, in some embodiments of the presently-disclosed subject matter, the ELP is a therapeutic agent delivery vector that does not cross the placental barrier. As described in further detail below, this therapeutic agent delivery vector is capable of fusion to many types of therapeutic agents, including small molecules, antibiotics, and therapeutic peptides, and allows those therapeutic agents to be stabilized in the maternal circulation, while also preventing them from entering the fetal circulation.

In some embodiments of the presently-disclosed subject matter, a method of delivering a therapeutic agent to a pregnant subject is provided. In some embodiments, an exemplary method includes administering to the pregnant subject an effective amount of a composition comprising an elastin-like polypeptide (ELP) coupled to a therapeutic agent, where the ELP sequence comprises at least about 5 repeats of the amino acid sequence VPGXG (SEQ ID NO: 1). In some embodiments, the method reduces the amount of the therapeutic agent crossing the placenta in a pregnant subject. In some embodiments, the ELP comprises repeated units of the amino acid sequence VPGXG (SEQ ID NO: 1), where X can be any amino acid except proline. In some embodiments, the ELP sequences comprises about 5 repeats to about 160 repeats of the amino acid sequence VPGXG (SEQ ID NO: 1). In some embodiments, the X in the amino acid sequence VPGXG (SEQ ID NO: 1) is Val, Ala, and Gly in a ratio of 1:4-8:3-7.

Non-limiting examples of ELP which may be used in accordance with the presently-disclosed subject matter include ELPs having: about 32 repeats of the amino acid sequence VPGXG (SEQ ID NO: 1), where X is Val, Ala, and Gly in a 1:8:7 ratio (see, e.g., SEQ ID NO: 2); about 80 repeats of the amino acid sequence VPGXG (SEQ ID NO: 1) where X is Val, Ala, and Gly in a 1:8:7 ratio (see, e.g., SEQ ID NO: 3); about 160 repeats of the amino acid sequence VPGXG (SEQ ID NO: 1) where X is Val, Ala, and Gly in a 1:8:7 ratio (see, e.g., SEQ ID NO: 4); about 40 repeats of the amino acid sequence VPGXG (SEQ ID NO: 1) where X is Gly (see, e.g., SEQ ID NO: 5); about 80 repeats of the amino acid sequence VPGXG (SEQ ID NO: 1) where X is Gly (see, e.g., SEQ ID NO: 6); about 160 repeats of the amino acid sequence VPGXG (SEQ ID NO: 1) where X is Gly (see, e.g., SEQ ID NO: 7); about 32 repeats of the amino acid sequence VPGXG (SEQ ID NO: 1) where X is Val, Ala, or Gly in a 1:4:3 ratio (see, e.g., SEQ ID NO: 8); about 80 repeats of the amino acid sequence VPGXG (SEQ ID NO: 1) where X is Val, Ala, or Gly in a 1:4:3 ratio (see, e.g., SEQ ID NO: 9); and about 160 repeats of the amino acid sequence VPGXG (SEQ ID NO: 1) where X is Val, Ala, or Gly in a 1:4:3 ratio (see, e.g., SEQ ID NO: 10); about 40 repeats of the amino acid sequence VPGXG (SEQ ID NO: 1) where X is Lys (see, e.g., SEQ ID NO: 11); about 80 repeats of the amino acid sequence VPGXG (SEQ ID NO: 1) where X is Lys (see, e.g., SEQ ID NO: 12); and about 160 repeats of the amino acid sequence VPGXG (SEQ ID NO: 1) where X is Lys (see, e.g., SEQ ID NO: 13). In some embodiments, the ELP sequence has an amino acid sequence selected from SEQ ID NOS: 2-13.

Turning now to the therapeutic agents that can be coupled to an exemplary ELP, various therapeutic agents known to those skilled in the art can be used in accordance with the presently-disclosed subject matter. As used herein, the terms "therapeutic agent" and "therapeutic agents" refer to any agent(s) that can be used in the "treatment" of a disease or disorder as defined herein below. In some embodiments, the therapeutic agent is selected from proteins, antibodies, and small molecule drugs, or functional analogs thereof.

The terms "polypeptide," "protein," and "peptide," which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

As used herein, the term "analog" refers to any member of a series of peptides having a common biological activity, including antigenicity/immunogenicity and antiangiogenic activity, and/or structural domain and having sufficient amino acid identity as defined herein.

As noted, in certain embodiments of the presently-disclosed subject matter, the therapeutic agents coupled to ELPs are those therapeutic agents that are desirable for introduction into the maternal circulation, but that should preferably be prevented from crossing the placenta and entering fetal circulation. Thus, in some embodiments, the compositions described herein are useful for delivery of any type of therapeutic agent that is regarded as harmful to fetal development. Such therapeutic agents include, but are not limited to, agents for the treatment of preeclampsia, chemotherapeutics, many drugs for cardiovascular diseases, anti-epileptic drugs, anti-emetic drugs, many immune modulating agents for autoimmune disorders, many drugs for endocrine disorders, certain antibiotics and antivirals, some anti-inflammatory agents, hormonal agents, and some analgesics. A partial list of drugs in pregnancy category X (i.e., drugs with known fetal toxicities) are listed in Table 1 below. In addition, many other drugs in pregnancy categories B, C, or D, which are identified as having some risk in pregnancy can benefit from delivery by coupling the drugs to an exemplary ELP in accordance with the presently-disclosed subject matter.

Additionally, the presently-disclosed subject matter is not limited to delivery of small molecule drugs, but is also useful for delivery of peptide agents, therapeutic proteins, and antibodies. A partial list of such other types of agents that can be improved by ELP delivery during pregnancy is included in Table 2 below.

In some embodiments, the therapeutic agent coupled to the ELP and used in accordance with the presently-disclosed subject matter is a therapeutic agent useful for the treatment of preeclampsia, eclampsia, myocardial infarction, renovascular disease, spinocerebellar ataxia, lupus, rheumatoid arthritis, psoriatic arthritis, multiple sclerosis, cancer, Crohn's disease, ankylosing spondylitis, cardiac hypertrophy, plaque psoriasis, hypertension, atherosclerosis, stroke, kidney stones, Alzheimer's disease and other neurodegenerative disorders, prevention of allograft rejection, hepatic fibrosis, schizophrenia, muscular dystrophy, macular degeneration, pulmonary edema, chronic pulmonary hypertension, or other disorders where ROS are deleterious. In some embodiments, the therapeutic agent coupled to the ELP is selected from the therapeutic agents listed in Tables 1 and 2 below.

TABLE 1

Exemplary cytotoxic drugs capable of couples to an ELP, including a partial list of Pregnancy Category X drugs (adapted from Monthly Prescribing Reference, Jan. 9, 2013).

ALLERGIC DISORDERS

Vistaril (hydroxyzine) Early pregnancy

CARDIOVASCULAR SYSTEM

| | |
|---|---|
| Advicor (niacin ext-rel/lovastatin) | Letairis (ambrisentan) |
| Aggrenox (dipyridamole/aspirin) 3rd trimester | Lipitor (atorvastatin) |
| | Livalo (pitavastatin) |
| Altoprev (lovastatin) | Mevacor (lovastatin) |
| Bayer (aspirin) 3rd trimester | Multaq (dronedarone) |
| Caduet (amlodipine/atorvastatin) | Pravachol (pravastatin) |
| Coumadin (warfarin sodium) | Simcor (niacin ext-rel/simvastatin) |
| Crestor (rosuvastatin) | Tracleer (bosentan) |
| Ecotrin (aspirin) 3rd trimester | Vytorin (ezetimibe/simvastatin) |
| Juvisync (sitagliptin/simvastatin) | Zocor (simvastatin) |
| Lescol (fluvastatin) | |
| Lescol XL (fluvastatin) | |

CENTRAL NERVOUS SYSTEM

| | |
|---|---|
| Beyaz (drospirenone/ethinyl estradiol) | Halcion (triazolam) |
| Doral (quazepam) | Restoril (temazepam) |
| Estazolam | Vistaril (hydroxyzine) Early pregnancy |
| Flurazepam | Yaz (drospirenone/ethinyl estradiol) |

DERMATOLOGICAL DISORDERS

| | |
|---|---|
| Amnesteem (isotretinoin) | Solaraze (diclofenac sodium) 3rd trimester |
| Avage (tazarotene) | |
| Beyaz (drospirenone/ethinyl estradiol) | Soriatane (acitretin) |
| Carac (fluorouracil) | Sotret (isotretinoin) |
| Claravis (isotretinoin) | SSD (silver sulfadiazine) Late pregnancy |
| Efudex (fluorouracil) | SSD AF (silver sulfadiazine) Late pregnancy |
| Estrostep Fe (norethindrone acetate/ethinyl estradiol) | Tazorac (tazarotene) |
| Fluoroplex (fluorouracil) | Tilia Fe (norethindrone acetate/ethinyl estradiol) |
| Loryna (drospirenone/ethinyl estradiol) | |
| Ortho Tri-Cyclen 28 (norgestimate/ethinyl estradiol) | Tri-Legest 21 (norethindrone acetate/ethinyl estradiol) |
| Propecia (finasteride) | Tri-Legest Fe (norethindrone acetate/ethinyl estradiol) |
| Silvadene (silver sulfadiazine) Late pregnancy | Tri-previfem(norgestimate/ethinyl estradiol) |
| Solage (mequinol/tretinoin) | Tri-sprintec (norgestimate/ethinyl estradiol) |
| | Yaz (drospirenone/ethinyl estradiol) |

ENDOCRINE DISORDERS

| | |
|---|---|
| Androderm (testosterone) | Lupron (leuprolide acetate) |
| Androgel (testosterone) | Methitest (methyltestosterone) |
| Android (methyltestosterone) | Oxandrin (oxandrolone) |
| Axiron (testosterone) | Striant (testosterone) |
| Delatestryl (testosterone enanthate) | Supprelin LA (histrelin acetate) |
| Depo-testosterone (testosterone cypionate) | Synarel (nafarelin) |
| | Testim (testosterone) |
| Egrifta (tesamorelin) | Testred (methyltestosterone) |
| Fluoxymesterone | Virilon (methyltestosterone) |
| Fortesta (testosterone) | |
| Juvisync (sitagliptin/simvastatin) | |

GASTROINTESTINAL TRACT

| | |
|---|---|
| Bellergal-S (phenobarbital/ergotamine tartrate) | Cytotec (misoprostol) |

INFECTIONS & INFESTATIONS

| | |
|---|---|
| Bactrim (sulfamethoxazole/trimethoprim) 3rd trimester | Macrodantin (nitrofurantoin macrocrystals) Pregnancy at term |
| Copegus (ribavirin) | Rebetol (ribavirin) |
| Flagyl (metronidazole) 1st trimester for trichomoniasis | Rebetron (ribavirin/interferon alfa -2b) |
| | Septra (sulfamethoxazole/trimethoprim) 3rd trimester |
| Furadantin (nitrofurantoin) Pregnancy at term | |

TABLE 1-continued

Exemplary cytotoxic drugs capable of couples to an ELP, including a partial list of Pregnancy Category X drugs (adapted from Monthly Prescribing Reference, Jan. 9, 2013).

| | |
|---|---|
| Gantrisin (sulfisoxazole) 3rd trimester | Sulfadiazine Pregnancy at term |
| Grifulvin V (griseofulvin) | Tindamax (tinidazole) 1st trimester |
| Gris-Peg (griseofulvin) | Urobiotic-250 |
| Macrobid (nitrofurantoin as macrocrystals and monohydrate) Pregnancy at term | (oxytetracycline HCl/sulfamethizole/phenazopyridine) Late pregnancy |
| | Virazole (ribavirin) |

METABOLIC DISORDERS

Zavesca (miglustat)

MUSCULOSKELETAL DISORDERS

| | |
|---|---|
| Advil (ibuprofen) 3rd trimester | Evista (raloxifene HCl) |
| Aleve (naproxen sodium) 3rd trimester | Feldene (piroxicam) Late pregnancy |
| Ansaid (flurbiprofen) Late pregnancy | Ibuprofen 3rd trimester |
| Arava (leflunomide) | Ketoprofen Late pregnancy |
| Arthrotec (diclofenac sodium/misoprostol) | Mobic (meloxicam) 3rd trimester |
| | Nabumetone 3rd trimester |
| Bayer (aspirin) 3rd trimester | Nalfon (fenoprofen calcium) 3rd trimester |
| BC Arthritis Strength (aspirin/caffeine/salicylamide) 3rd trimester | Naprelan (naproxen) 3rd trimester |
| | Prevacid Naprapac (lansoprazole/naproxen) 3rd trimester |
| Cataflam (diclofenac potassium) Late pregnancy | Probenecid + Colchicine |
| | Prolia (denosumab) |
| Celebrex (celecoxib) 3rd trimester | Rheumatrex (methotrexate sodium) |
| Choline magnesium trisalicylate Pregnancy at term | Salsalate 3rd trimester |
| | Soma Compound w. Codeine |
| Dantrium (dantrolene) | (carisoprodol/aspirin/codeine) 3rd trimester |
| Daypro (oxaprozin) 3rd trimester | |
| Diclofenac sodium Late pregnancy | Vimovo (naproxen/esomeprazole) Late pregnancy (≥30 wks) |
| Diflunisal 3rd trimester | |
| Duexis (ibuprofen/famotidine) Late pregnancy (≥30 wks) | Zipsor (diclofenac potassium) Late pregnancy |
| Ecotrin (aspirin) 3rd trimester | |
| Etodolac Late pregnancy | |

NEOPLASMS

| | |
|---|---|
| Bexxar (tositumomab) | Menest (esterified estrogens) |
| Casodex (bicalutamide) | Revlimid (lenalidomide) |
| Delestrogen (estradiol valerate) | Targretin (bexarotene) |
| Efudex (fluorouracil) | Thalomid (thalidomide) |
| Eligard (leuprolide acetate) | Trelstar (triptorelan pamoate) |
| Estrace (estradiol) | Trexall (methotrexate) |
| Evista (raloxifene HCl) | Vantas (histrelin acetate) |
| Firmagon (degarelix) | Zytiga (abiraterone acetate) |
| Fluoxymesterone | |

NUTRITION

| | |
|---|---|
| Didrex (benzphetamine) | Megace Suspension (megestrol acetate) |
| Fosteum (genistein/citrated zinc/cholecalciferol) | Xenical (orlistat) |
| Megace ES (megestrol acetate) | |

OB/GYN

| | |
|---|---|
| ALL ORAL CONTRACEPTIVES | Lupron Depot (leuprolide acetate) |
| ALL HORMONE REPLACEMENT THERAPY | Luveris (lutropin alfa) |
| | Menopur (menoptropins) |
| Advil (ibuprofen) 3rd trimester | Methergine (methylergonovine) |
| Aleve (naproxen sodium) 3rd trimester | Midol cramp (ibuprofen) 3rd trimester |
| Aygestin (norethindrone acetate) | Midol menstrual (acetaminophen/caffeine/pyrilamine) 3rd trimester |
| Betadine douche (povidone-iodine) | |
| Bravelle (urofollitropin) | |
| Cataflam (diclofenac potassium) Late pregnancy | Midol PMS (acetaminophen/pamabrom/pyrilamine) 3rd trimester |
| Celebrex (celecoxib) 3rd trimester | |
| Cetrotide (cetrorelix) | Midol teen (acetaminophen/pamabrom) 3rd trimester |
| Clomid (clomiphene citrate) | |
| Depo-subQ provera (medroxyprogesterone acetate) | Mifeprex (mifepristone) |
| | Naprelan (naproxen) 3rd trimester |
| Endometrin (micronized progesterone) | Ovidrel (choriogonadotropin alfa) |
| Ectopic pregnancy | Ponstel (mefenamic acid) Late pregnancy |
| Flagyl (metronidazole) 1st trimester for trichomoniasis | Repronex 75 IU (follicle-stimulating hormone/luteinizing hormone) |
| Follistim (follitropin beta) | |

TABLE 1-continued

Exemplary cytotoxic drugs capable of couples to an ELP, including a partial list of Pregnancy Category X drugs (adapted from Monthly Prescribing Reference, Jan. 9, 2013).

| | |
|---|---|
| Ganirelix acetate | Repronex 150 IU |
| Gonal-F (follitropin alfa) | (follicle-stimulating hormone/luteinizing |
| Ibuprofen 3rd trimester | hormone) |
| | Serophene (clomiphene citrate) |
| | Synarel (nafarelin acetate) |
| | Tindamax (tinidazole) 1st trimester |
| | Zoladex (goserelin) |

PAIN MANAGEMENT

| | |
|---|---|
| Advil (ibuprofen) 3rd trimester | Excedrin Migraine |
| Advil Migraine (ibuprofen) 3rd trimester | (acetaminophen/aspirin/caffeine) 3rd |
| Aleve (naproxen sodium) 3rd trimester | trimester |
| Bayer (aspirin) 3rd trimester | Fiorinal (butalbital/aspirin/caffeine) 3rd |
| BC Original Formula | trimester |
| (aspirin/caffeine/salicylamide) 3rd | Fiorinal w. Codeine |
| trimester | (butalbital/aspirin/caffeine/codeine |
| Cafergot (ergotamine tartrate/caffeine) | phosphate) 3rd trimester |
| Caldolor (ibuprofen) 3rd trimester | Ibudone |
| Cataflam (diclofenac potassium) Late | (hydrocodone bitartrate/ibuprofen) 3rd |
| pregnancy | trimester |
| Celebrex (celecoxib) 3rd trimester | Ketorolac Late pregnancy |
| Choline magnesium trisalicylate | Migranal (dihydroergotamine mesylate) |
| Pregnancy at term | Motrin Migraine Pain (ibuprofen) 3rd |
| D.H.E. 45 (dihydroergotamine mesylate) | trimester |
| Diflunisal 3rd trimester | Nalfon (fenoprofen calcium) 3rd trimester |
| Etodolac Late pregnancy | Naprelan (naproxen) 3rd trimester |
| | Percodan (oxycodone HCl/aspirin) 3rd |
| | trimester |
| | Ponstel (mefenamic acid) Late pregnancy |
| | Synalgos-DC |
| | (dihydrocodeine |
| | bitartrate/aspirin/caffeine) 3rd trimester |
| | Vicoprofen (hydrocodone |
| | bitartrate/ibuprofen) 3rd trimester |

UROGENITAL SYSTEM

| | |
|---|---|
| Avodart (dutasteride HCl) AVOID | Jalyn (dutasteride/tamsulosin HCl) |
| HANDLING CAPSULES | Lithostat (acetohydroxamic acid) |
| Caverject (alprostadil) | Proscar (finasteride) |
| Edex (alprostadil) | |

TABLE 2

Partial list of peptide, protein, and antibody agents that can be coupled to a ELP for delivery during pregnancy.

THERAPEUTIC PEPTIDES

| Peptide Name | Protein of origin | GenBank No. (of gene from which peptide is derived) | Amino Acids |
|---|---|---|---|
| PNC-2 | Ras | 3265 | 96-110 |
| PNC-7 | Ras | 3265 | 35-47 |
| PNC-25 | SOS | 6654 | 994-1004 |
| n.s.* | Raf | 5894 | 97-110 |
| n.s.* | Raf | 5894 | 143-150 |
| n.s.* | NF1-GAP | 4763 | 1121-1128 |
| SP1068 | EGFR | 1956 | 1063-1073 |
| SY317 | Shc | 6464 | 312-323 |
| n.s.* | MEK1 | 5604 | 1-13 |
| n.s.* | GST-pi | 2950 | 34-50 |
| JNKI1 | JIP1/IB1 | 9479 | 153-172 |
| JNKI2 | JIP2/IB2 | 9479 | 134-151 |
| I-JIP | JIP1/IB1 | 9479 | 143-163 |
| TI-JIP | JIP1/IB1 | 9479 | 153-163 |
| NBD | IKKβ | 3551 | 735-745 |
| CC2 | NEMO | 8517 | 253-287 |
| LZ | NEMO | 8517 | 294-336 |
| SN50 | NF-κB p50 | 4790 | 360-369 |
| pp21 | IκBα | 4792 | 21-41 |
| p65-P1 | NF-κB p65 | 5970 | 271-282 |
| p65-P6 | NF-κB p65 | 5970 | 525-537 |

TABLE 2-continued

Partial list of peptide, protein, and antibody agents that can be coupled to a ELP for delivery during pregnancy.

| | | | |
|---|---|---|---|
| C1 | p53 | 7157 | 369-383 |
| Peptide 46 | p53 | 7157 | 361-382 |
| CDB3 | 53BP2 | 7159 | 490-498 |
| TIP | p53 | 7157 | 12-30 |
| Super-TIP | (phage selected) | | |
| PNC-27 | p53 | 7157 | 12-26 |
| PNC-21 | p53 | 7157 | 12-20 |
| PNC-28 | p53 | 7157 | 17-26 |
| αHDM2 | p53 | 7157 | 16-27 |
| Peptide 3 | $p14^{ARF}$ | 1029 | 1-20 |
| H1-S6A, F8A | c-Myc | 4609 | 368-381 |
| n.s.* | p21 | 1026 | 17-33 |
| n.s.* | p21 | 1026 | 63-77 |
| Peptide 10 | p21 | 1026 | 141-160 |
| W10 | p21 | 1026 | 139-164 |
| Peptide 6 | p16 | 1029 | 84-103 |
| Peptide 5a | p27 | 1027 | Modified from 30-34 |
| C4 | cyclin A | 890/8900 | 285-306 |
| n.s.* | E2F | 1869 | 87-64 |
| n.s.* | Rb | 5925 | 864-880 |
| Akt-in | TCL1 | 8115 | 10-24 |
| Peptide2 | FKHRL1 | 2309 | 16-24 |
| n.s.* | Bak | 578 | 72-87 |
| TO4 | Bax | 581 | 52-72 |
| n.s.* | Bax | 581 | 53-86 |
| n.s.* | Bad (*mus musculis*) | 12015 | 140-165 |
| n.s.* | Bad | 572 | 103-127 |
| BH3 BAD | Bad | 572 | 103-123 |
| Bim | Bim | 10018 | 145-165 |
| n.s.* | Bid | 637 | 84-99 |
| $SAHB_A$ | Bid | 637 | 80-101 |
| Smac-7 | Mature Smac | 56616 | 1-7 |
| n.s.* | Mature Smac | 56616 | 1-4 |
| dAVPI | Mature Smac | 56616 | 1-4 |
| Nox2ds | NADPH oxidase 2 | 1536 | 86-94 |
| Nox2 C-terminal peptide 1 | NADPH oxidase 2 | 1536 | 552-570 |
| Nox2 C-terminal peptide 2 | NADPH oxidase 2 | 1536 | 550-569 |
| Nox2 C-terminal peptide (with mutation at residue 500) | NADPH oxidase 2 | 1536 | 491-504 |
| $p22^{phox}$ derived peptide 1 | $p22^{phox}$ | 1535 | 9-23 |
| $p22^{phox}$ derived peptide 2 | $p22^{phox}$ | 1535 | 31-45 |
| $p22^{phox}$ derived peptide 3 | $p22^{phox}$ | 1535 | 47-61 |
| $p22^{phox}$ derived peptide 4 | $p22^{phox}$ | 1535 | 85-99 |
| $p22^{phox}$ derived peptide 5 | $p22^{phox}$ | 1535 | 113-127 |
| $p22^{phox}$ derived peptide 6 | $p22^{phox}$ | 1535 | 82-95 |
| $p22^{phox}$ derived peptide 7 | $p22^{phox}$ | 1535 | 175-194 |
| $p47^{phox}$ derived peptide 1 | $p47^{phox}$ | 653361 | 323-332 |
| $p47^{phox}$ derived peptide 2 | $p47^{phox}$ | 653361 | 314-331 |
| $p47^{phox}$ derived peptide 3 | $p47^{phox}$ | 653361 | 315-328 |
| $p47^{phox}$ derived peptide 4 | $p47^{phox}$ | 653361 | 323-332 |
| $p47^{phox}$ derived peptide 5 | $p47^{phox}$ | 653361 | 334-347 |

THERAPEUTIC PROTEINS

| | | |
|---|---|---|
| VEGF | Insulin | β-Gluco-cerebrosidase |
| PIGF | Growth hormone | Alglucosidase-α |
| IL10 | Mecasermin | Laronidase |
| IL11 | Factor VIII | Idursulphase |
| Erythropoietin | Factor IX | Galsulphase |
| Darbepoetin | Antithormbin III | Agalsidase-β |
| G-CSF | Protein C | α-1-Proteinase inhibitor |
| Peg-G-CSF | tPA | Lipase |
| GM-CSF | Urokinase | Amylase |
| α-interferon | Factor VIIa | Adenosine deaminase |
| Interferon-α2a | Calcitonin | Albumin |
| Interferon-α2b | Teriparatide | FSH |
| Peg-Interferon-α2a | Exenatide | HCG |
| Peg-Interferon-α2b | Octreotide | Lutropin |

TABLE 2-continued

Partial list of peptide, protein, and antibody agents that
can be coupled to a ELP for delivery during pregnancy.

| | | |
|---|---|---|
| Interferon-αN3 | rhBMP2 | Nesiritide |
| Interferon-β1a | rhBMP7 | Botulinum Toxin type A |
| Interferon-β1b | GnRH | Botulinum Toxin type B |
| Interferon-γ1b | KGF | Collagenase |
| IL2 | PDGF | DNAse I |
| ETAF | Trypsin | Hyaluronidase |
| Peg-Asparaginase | Bivalirudin | Papain |
| Rasb peptide containing a p50 NLS capable of blocking the nuclear import of NF-κB upon stimulation in a variety of cell lines is fused to an exemplary ELP carrier described herein. In some embodiments, and as described in further detail below, such a polypeptide also contains a cell penetrating peptide (CPP) to mediate uptake into target cells. A non-limiting example of the composition is Shown as SynB1-ELP-p50 (SEQ ID NO: 15) where a SynB1 peptide fused to N-terminus of a ELP sequence (SEQ ID NO: 4), and a p50 peptide sequence fused to the C-terminus of the ELP sequence.

In still other embodiments, the therapeutic agent coupled to the ELP is a NADPH oxidase inhibitory peptide. Another contributing factor to many cardiovascular disorders, including preeclampsia, is the production of reactive oxygen species (ROS). ROS are a natural byproduct of metabolism, but if produced in excessive levels, they can cause damage to key cellular components. For example, high ROS levels can induce DNA damage, lipid peroxidation in the plasma membrane, and oxidation of cellular proteins, and downstream results of these effects can include cell death. One major producer of the ROS superoxide is NADPH oxidase (NOX). NOX activity has been shown to be important for pathological ROS production in hypertension, atherosclerosis, stroke, preeclampsia, kidney stones, Alzheimer's disease and other neurodegenerative disorders, schizophrenia, muscular dystrophy, macular degeneration, pulmonary edema, chronic pulmonary hypertension, among others (Paravicine T M, et al., 2008; Park Y M, et al., 2009; Radermacher K A, et al., 2013; Matsubara S, et al., 2001; Khan S R, 2013; Block M L, 2008; Wang X, et al., 2013; Whitehead N P, et al., 2010; Monaghan-Benson E, et al., 2010; Araneda O F, et al., 2012). Thus, in some embodiments, a peptide inhibitor of NADPH oxidase called Nox2ds (abbreviated NOX) is coupled to an ELP. NOX is a 9 amino acid sequence from the cytosolic portion of Nox2 that prevents the interaction of the p47phox structural subunit with Nox2 (Cifuentes-Pagano E, et al., 2012; Csanyi G, et al., 2011). In some embodiments, a CPP is also coupled to the NOX polypeptide composition to mediate its uptake into target cells. A non-limiting sequence is shown as SynB1-ELP-NOX (SEQ ID NO: 16) where SynB1 peptide sequence fused to the N-terminus of a ELP sequence (SEQ ID NO: 4), and NOX peptide fused to the C-terminus of the ELP sequence.

In some embodiments, the therapeutic agent is a small molecule drug, where the size of the small molecule drug is less than 2,000 Dalton. In some embodiments, the small molecule drug is known to cause adverse events during pregnancy. Non-limiting examples of adverse events include teratogenicity, fetal growth restriction, embryotoxicity, or fetal demise. In some embodiments, the small molecules include pregnancy category C, D, or X drugs classified by the US FDA (Federal Register, Vol. 73, No. 104, May 29, 2008; Postmarket Drug Safety Information for Patients and Providers, Index to Drug-Specific Information). In some embodiments, the small molecule drug includes anti-hypertensive drugs. Non-limiting examples of the anti-hypertensive drugs include lovastatin, atorvastatin, pitavastatin, pravastatin, simvastatin, rosuvastatin, fluvastatin, aspirin, captopril, zofenopril, enalapril, ramipril, perindopril, quinapril, lisinopril, cilazapril, trandolapril, benazepril, imidapril, foninopril. In some embodiments, the small molecule drug includes anti-epileptic agents. Non-limiting examples of the anti-epileptic agents include phenytoin, valproate, phenobarbital, valproic acid, trimethadione, paramethadione, topiramate, carbamazepine, levetiracetam, lamotrigine. In some embodiments, the small molecule drug includes anti-emetic drugs. Non-limiting anti-emetic drugs include doxylamine, pyridoxine, prochlorperazine, chlorpromazine, promethazine, trimethobenzamide, ondansetron. In some embodiments, the small molecule drug includes cancer chemotherapeutics. Non-limiting examples of the cancer chemotherapeutics are taxanes including paclitaxel and decetaxel; vinca alkaloids including vinblastine, vincristine, venorelbine, and vinflunin; antimetabolites including methotrexate and 5-fluorouracil; topoisomerase inhibitors including doxorubicin, daunorubicin, epirubicin, etoposide, and camptothecin; cyclophosphamide or related alkylating agents.

Various means of coupling the ELP to therapeutic agents can be used in accordance with the presently-disclosed subject matter and are generally known to those of ordinary skill in the art. Such coupling techniques include, but are not limited to, chemical coupling and recombinant fusion technology. Depending on the particular coupling techniques utilized, in some embodiments, the number of ELPs or therapeutic agents per molecule, and their respective positions within the molecule, can be varied as needed. Further, in some embodiments, the therapeutic agent may further include one or more spacer or linker moieties, which in addition to providing the desired functional independence of the ELP and therapeutic agents, can optionally provide for additional functionalities, such as a protease-sensitive feature to allow for proteolytic release or activation of the therapeutic agent. Moreover, in certain embodiments, the therapeutic agent may be coupled to one or more targeting components such as, for example, a peptide or protein that targets the therapeutic agent to a particular cell type, e.g., a cancer cell, or to a particular organ, e.g., the liver.

To facilitate entry of the peptide compositions described herein into a cell where the therapeutic effect of the compositions can be exerted, in some embodiments, the polypeptide compositions further include a cell-penetrating peptide (CPP) sequence or an organ targeting peptide sequence that is coupled to the ELP.

As used herein, the term "cell penetrating peptide" refers to short peptides sequences that facilitate cellular uptake of various agents, such as polypeptides, nanoparticles, small chemical molecules, and fragments of DNA. The function of the CPPs are to deliver the agents into cells, a process that commonly occurs through endocytosis with the cargo delivered to the endosomes of living mammalian cells. In some embodiments, the cell penetrating peptides or organ targeting peptides couple to the ELP carrier either through chemical linkage via covalent bonds or through non-covalent interactions. Non-limiting examples of the cell-penetrating peptide that can be coupled to the therapeutic agent or ELP include penetratin, Tat, SynB1, Bac, polyArg, MTS, Transportan, or pVEC.

The term "organ targeting peptide refers to short peptides designed to have specificity for the vascular beds or other cell types of specific organs. In some embodiments, the organ targeting peptide is selected from kidney targeting peptides, placenta targeting peptides, or brain targeting peptides.

Further provided, in some embodiments of the presently-disclosed subject matter are methods for the treatment of various diseases and disorders using the exemplary ELP-therapeutic agent-containing compositions described herein. In some embodiments, the presently-disclosed subject matter includes a method of treating a disease or disorder in a pregnant subject wherein the pregnant subject is administered an effective amount of a composition comprising an ELP coupled to a therapeutic agent, wherein the ELP is at least 5 repeats of amino acid sequence VPGXG (SEQ ID NO: 1). Exemplary diseases or disorders that can be treated in accordance with the presently-disclosed subject matter include, but are not limited to, preeclampsia, eclampsia, myocardial infarction, renovascular disease, spinocerebellar ataxia, lupus, rheumatoid arthritis, psoriatic arthritis, multiple sclerosis, cancer, Crohn's disease, ankylosing spondylitis, cardiac hypertrophy, plaque psoriasis, hypertension, atherosclerosis, stroke, kidney stones, Alzheimer's disease and other neurodegenerative disorders, prevention of allograft rejection, hepatic fibrosis, schizophrenia, muscular dystrophy, macular degeneration, pulmonary edema, chronic pulmonary hypertension, or other disorders where ROS are deleterious.

As used herein, the terms "treatment" or "treating" relate to any treatment of a disease or disorder, including but not limited to prophylactic treatment and therapeutic treatment. As such, the terms "treatment" or "treating" include, but are not limited to: preventing a disease or disorder or the development of a disease or disorder; inhibiting the progression of a disease or disorder; arresting or preventing the further development of a disease or disorder; reducing the severity of a disease or disorder; ameliorating or relieving symptoms associated with a disease or disorder; and causing a regression of a disease or disorder or one or more of the symptoms associated with a disease or disorder.

For administration of a therapeutic composition as disclosed herein (e.g., an ELP coupled to a therapeutic agent), conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al, (Freireich et al., 1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082).

Regardless of the route of administration, the compositions of the presently-disclosed subject matter are typically administered in an amount effective to achieve the desired response. As such, the term "effective amount" is used herein to refer to an amount of the therapeutic composition (e.g., en ELP coupled to a therapeutic agent, and a pharmaceutical vehicle, carrier, or excipient) sufficient to produce a measurable biological response. Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, N.J.; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties, Choice, Therapeutic Use and Economic Value of Drugs in Disease Management, 4th ed, Adis International, Auckland/Philadelphia; Duch et al., (1998) *Toxicol. Lett.* 100-101:255-263.

In some embodiments of the presently-disclosed subject matter, the compositions described herein have been found to be particularly useful for the treatment of preeclampsia during pregnancy. However, it is contemplated that the exemplary compositions described are also useful not only for the treatment of a number of other diseases and disorders, but also both during pregnancy and in non-pregnant populations. For example, the ELP-delivered VEGF can be useful for treatment of myocardial infarction, renovascular disease, spinocerebellar ataxia, or other disorders in which VEGF levels are reduced. Additionally, the ELP-delivered NF-κB inhibitory peptide could be useful for a variety of disorders with an inflammatory component, including lupus, rheumatoid arthritis, psoriatic arthritis, multiple sclerosis, cancer, Crohn's disease, ankylosing spondylitis, cardiac hypertrophy, plaque psoriasis, or other disorders in which NF-κB plays a central regulatory role. Moreover, the ELP-delivered NOX peptide could be used for hypertension, atherosclerosis, stroke, kidney stones, Alzheimer's disease and other neurodegenerative disorders, prevention of allograft rejection, hepatic fibrosis, schizophrenia, muscular dystrophy, macular degeneration, pulmonary edema, chronic pulmonary hypertension, or other disorders where ROS are deleterious.

In addition to the advantageous properties and uses described above, and without wishing to be bound by any particular theory, it is believed that the fusion of therapeutic agents to the ELP carrier provides many other advantages as well. For instance, in certain embodiments, ELP fusion increases the plasma half-life of therapeutic agents as many small molecule drugs, peptides, and therapeutic proteins are typically rapidly cleared from circulation by renal filtration. As another example, in some embodiments, ELP fusion increases the solubility of therapeutics as ELP fusion has been shown to increase the solubility of many poorly soluble therapeutics. As yet another example, in some embodiments, ELP fusion protects labile peptide therapeutics from degradation in vivo as ELP fusion provides a large sized carrier for labile therapeutics that protects them from enzymes that would degrade them (Bidwell G L, et al., 2013; Bidwell G L, 3rd, et al., 2012). Further, in some embodiments, ELP fusion decreases the immunogenicity of therapeutics that may be otherwise recognized as foreign by the immune system as ELP has been shown to be non-immunogenic and to decrease the immunogenicity of attached therapeutics (Urry D W, et al., 1991).

As an additional example of the advantageous use of an ELP, in some embodiments, the ELP sequence can be easily modified to carry any desired protein or peptide, or to incorporate labeling sites for attachment of small molecules. Indeed, when an ELP is genetically encoded, and its coding sequence is inserted into a plasmid vector, doing so allows manipulation of the ELP sequence, and fusions of peptides and therapeutic proteins can be made by molecular biology techniques (Bidwell G L, 2012; Bidwell G L, et al, 2005; Bidwell G L, et al., 2010; Bidwell G L, 3rd, Wittom A A, et al., 2010; Massodi I, et al., 2005; Massodi I, et al., 2009; Meyer D E, 1999; Moktan S, et al., 2012; Moktan S, et al., 2012). Moreover, ELP can be purified after recombinant expression in bacteria. The genetically encoded nature of ELP also allows for expression in bacteria. Large amounts of ELP or ELP fusion proteins can be expressed recombinantly using E. coli-based expression systems. Additionally, ELP has the property of being thermally responsive. Above a characteristic transition temperature, ELP aggregates and precipitates, and when the temperature is lowered below the transition temperature, ELP re-dissolves. Therefore, purification of ELP after expression in bacteria can include heating the bacterial lysate above the transition temperature and collecting ELP or ELP fusion proteins by centrifugation. Repeated centrifugations above and below the transition temperature then results in pure ELP (Meyer D E, et al., 1999).

Furthermore, in some embodiments of the presently-disclosed subject matter, by using ELPs, ELPs can be targeted to desired tissues in vivo using targeting agents or peptides. As noted above, because of the ease of generating ELP fusions, ELP can be conjugated with any targeting agent, be it a peptide, small molecule, or antibody. Indeed, fusion with CPPs or organ targeting peptides can be used to not only increase cell and tissue uptake of ELPs, but also to direct ELP to specific tissues in vivo and even to specific intracellular compartments within a particular subject (Bidwell G L, et al., 2013; Bidwell G L, et al., 2009).

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Polynucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; Sec Methods in Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc, N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Example 1. Design and Method for Generation of ELP-Fusion Polypeptides

ELP sequences were made by recursive directional ligation. A synthetic nucleotide cassette containing the coding sequence for 5 to 10 VPGXG (SEQ ID NO: 1) repeats with the desired amino acids at the X position and flanked by PflMI and BlgI restriction sites was cloned into the pUC19 vector at the EcoRI and HinDIII sites. The sequence of this construct was confirmed by DNA sequencing using standard M13 forward and reverse primers. Once one block of 5 to 10 VPGXG (SEQ ID NO: 1) repeats was inserted and confirmed, it was excised from pUC19 using PflMI and BglI restriction digestion and purified using agarose electrophoresis. A second aliquot of pUC19 containing the VPGXG (SEQ ID NO: 1) repeated sequence was linearized by digestion with PflMI only, and the gel purified cassette was ligated into the PflMI restriction site. This resulted in an in-frame fusion of the block of 5-10 VPGXG (SEQ ID NO: 1) repeats with a second block of 5 to 10 VPGXG (SEQ ID NO: 1) repeats, effectively doubling the number of ELP repeats. This process was repeated, doubling the ELP repeat number each time, until the desired molecular weight was reached. If necessary, smaller blocks (such as the original 5-10 repeat block) were used to increase the ELP repeat size in 5 to 10 block increments until the exact desired VPGXG (SEQ ID NO: 1) repeat number was achieved. The final ELP sequence was then excised from pUC19 using PflMI and BglI and inserted into a modified pET25b expression vector at an engineered SfiI site for recombinant protein expression.

N- and C-terminal modifications of ELP were made by cloning desired N- and/or C-terminal peptide or protein coding sequence into the pET25b expression vector between the NdeI and BamHI restriction sites. In all cases, the N- and/or C-terminal modifications were separated by an SfiI restriction site for later insertion of ELP. For peptide modification (such as CPPs, the NADPH oxidase inhibitory peptide, or the NF-κB inhibitory peptide), the coding sequence for the peptides was generated as a synthetic oligonucleotide cassette with ends compatible with the desired restriction sites. For larger protein insertions, such as VEGF, the coding sequence was either commercially synthesized with *E. coli*-optimized codons and flanked by the desired restriction sites, or the coding sequence was amplified from human cDNA by PCR with custom primers used to add any necessary N- or C-terminal amino acids and to add the desired restriction sites. The intermediate constructs containing only the N- and/or C-terminal modifications in the pET25b vector were confirmed by DNA sequencing using the standard T7 promoter and T7 terminator primers. The desired ELP coding sequence was extracted from pUC19 using PflMI and BglI digestion and cloned into the modified pET25b vector at the engineered SfiI site. This resulted in in-frame fusions of ELP with the desired N- and/or C-terminal peptide or protein modifications. The final constructs were again confirmed by DNA sequencing.

Example 2. Recombinant Expression and Purification of Polypeptides

ELPs and ELP fusion proteins were expressed and purified from *E. coli* BLR (DE3) or Rosetta2®(DE3) (for constructs resulting from human cDNA containing human-optimized codons). Briefly, 500 mL of TB Dry liquid culture media (MoBio) was inoculated with the expression strain and cultured at 37° C. with 250 rpm agitation for 16-18 h. In the absence of the pLysS lysozyme-expressing plasmid, the pET expression system allows for leaky production of the recombinant protein even without inducing agents. Bacteria were harvested by centrifugation and lysed by sonication (10×10 sec pulses, 75% amplitude, Fisher Sonic Dismembrator). Cell debris was removed by centrifugation, and nucleic acids were precipitated with 10% polyethylene imine and removed by centrifugation. NACl was added to the soluble bacterial lysate to lower the ELP transition temperature (4 g/30 mL), and the lysate was heated to 42° C. to induce aggregation of the ELP-containing polypeptides. Polypeptides were collected by centrifugation at 42° C., the supernatant containing other soluble proteins was discarded, then the ELPs or ELP-fusion proteins were re-solubilized in ice cold PBS. Any remaining debris was removed after re-dissolving the ELP-containing proteins by centrifugation at 4° C. This heat-induced aggregation process was repeated two to three times to achieve purified ELP or ELP-fusion proteins. Purity of the resulting polypeptides was confirmed by SDS-PAGE analysis.

Example 3. Use of ELP for Drug Delivery During Pregnancy

Figure 1:
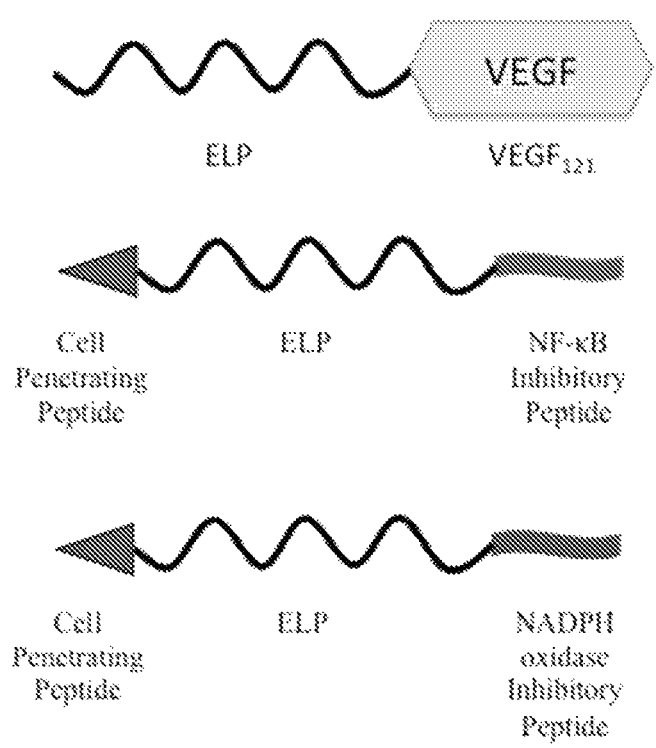
FIG. 1 includes schematic diagrams showing some of the exemplary compositions described herein, including: a schematic diagram showing an Elastin-like polypeptide (ELP) drug carrier fused to $VEGF_{121}$; an ELP carrier fused to a peptide inhibitor of the NF-κB pathway; and an ELP carrier fused to a peptide inhibitor of NADPH oxidase. The polypeptides also contain a cell penetrating peptide to mediate uptake into target cells.
Figure 2:
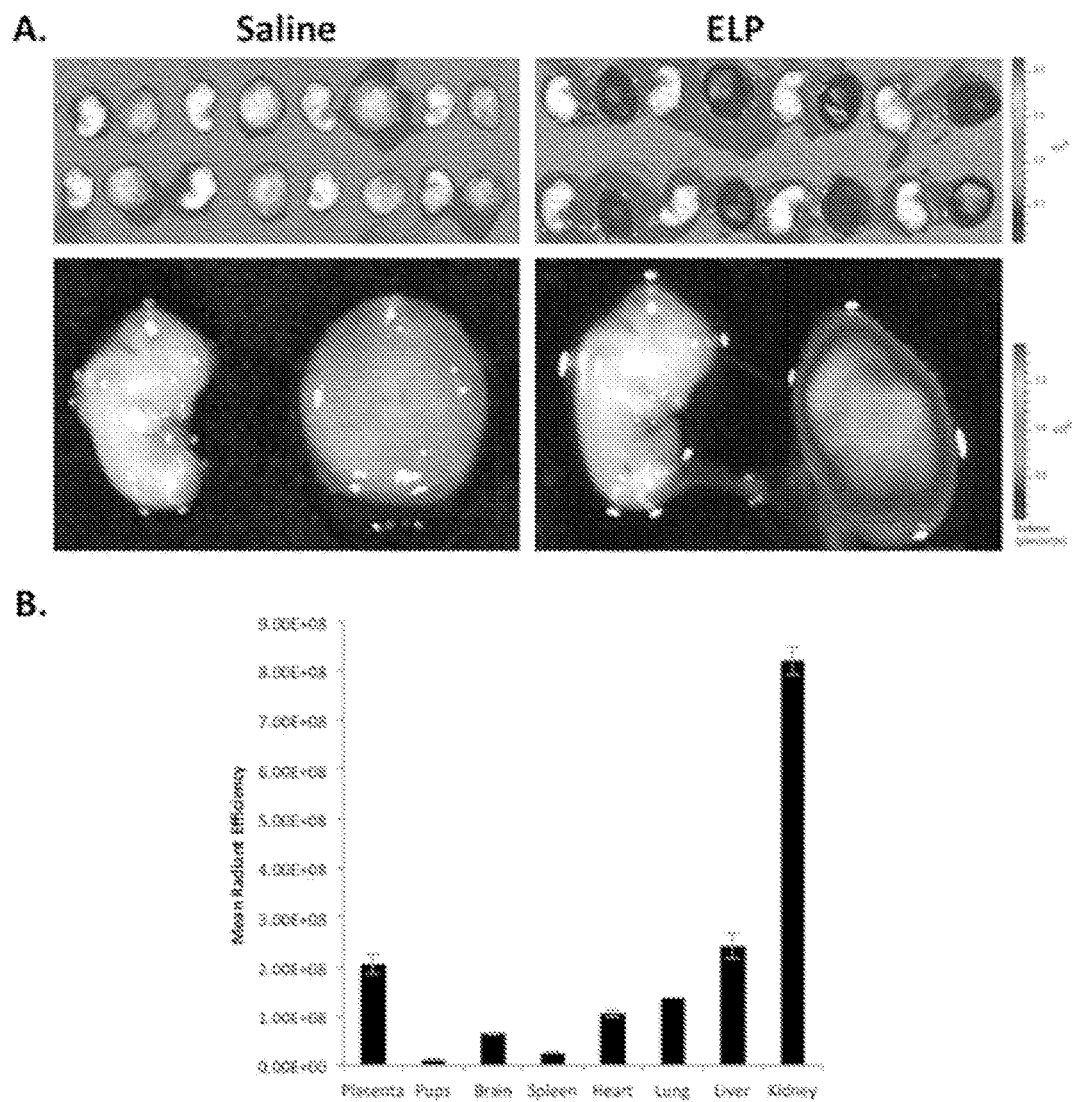
FIG. 2 includes a series of images and a graph showing the biodistribution of ELP in pregnant rats.

In order to test the hypothesis that ELP-fused therapeutics do not cross the placenta, an experiment was performed using the unmodified ELP carrier. Pregnant Sprague Dawley rats on day 14 of gestation were injected with fluorescently labeled ELP (100 mg/kg IV). Four hours after injection, which is about one half-life for this polypeptide, the rats were sacrificed and the placentas, pups, and major organs were removed for examination. Placentas and pups were dissected from the amniotic sacks and imaged ex vivo using an IVIS Spectrum animal imager to detect and quantitate the ELP levels. As shown in FIG. 2A, the placentas of animals injected with ELP-Alexa633 stained brightly, indicating that much protein had accumulated in them. In contrast, almost no ELP was detectable in the pups. The image intensities of the placentas, pups, and major organs were quantitated using Living Image software, and the results are shown in FIG. 2B. ELP accumulated strongly in the placenta, but ELP was barely detectable over autofluorescence in the pups. The placental accumulation was nearly equivalent to levels in the liver, an organ known to accumulate high levels of macromolecules due to its role in the reticuloendothelial system (Seymour L W, et al., 1987), and was second only to the kidney, which is likely actively involved in excretion and/or reuptake of the polypeptide. These high ELP levels in the placenta are unprecedented with this molecule. By way of comparison, the placenta levels are 2 to 10 fold higher than the tumors levels (Bidwell G L, et al., *PloS One,* 2013; Bidwell G L, 3rd, *Cancer Lett.,* 2012). This is a reflection of the strong vascular perfusion of this organ and indicates that ELP is a great candidate carrier for placental drug delivery.

This example also examined whether the addition of a CPP to ELP would affect its penetration across the placenta. SynB1-ELP was labeled with Alexa633 and injected as described above. For comparison, animals were injected with saline control or ELP-Alexa633 at an equivalent dose. Four hours after injection, placental, fetal, and organ levels were determined by ex vivo fluorescence imaging. As shown in FIG. 3A, the addition of the SynB1 CPP to the ELP carrier increased its uptake in the placenta, but did not affect its delivery to the pups. FIG. 3B shows that the addition of SynB1 also increased the polypeptide deposition in the heart, liver, and kidneys relative to ELP, and SynB1 decreased deposition in the spleen. In addition to the ex vivo fluorescence imaging, the fetal-amnio-placental complex was removed, rapidly frozen, and sectioned using a cryo-microtome. Tissue sections were stained with the actin-specific rhodamine-phalloidin to allow visualization of all tissue and imaged directly using a fluorescence slide scanner. As shown in FIG. 3C, both ELP-Alexa633 and SynB1-ELP-Alexa633 accumulated at high levels in the placenta relative to autofluorescence controls. In both cases, however, no polypeptide was detectable in the pups. The intraplacental distribution SynB1-ELP-Alexa633 differed slightly from ELP-Alexa633. The unmodified ELP accumulated at high levels throughout the placenta, whereas SynB1-ELP accumulation was localized more strongly at the chorionic plate. Both polypeptides could be detected within the cells of the placenta when examined microscopically (FIG. 3D).

Figure 4:
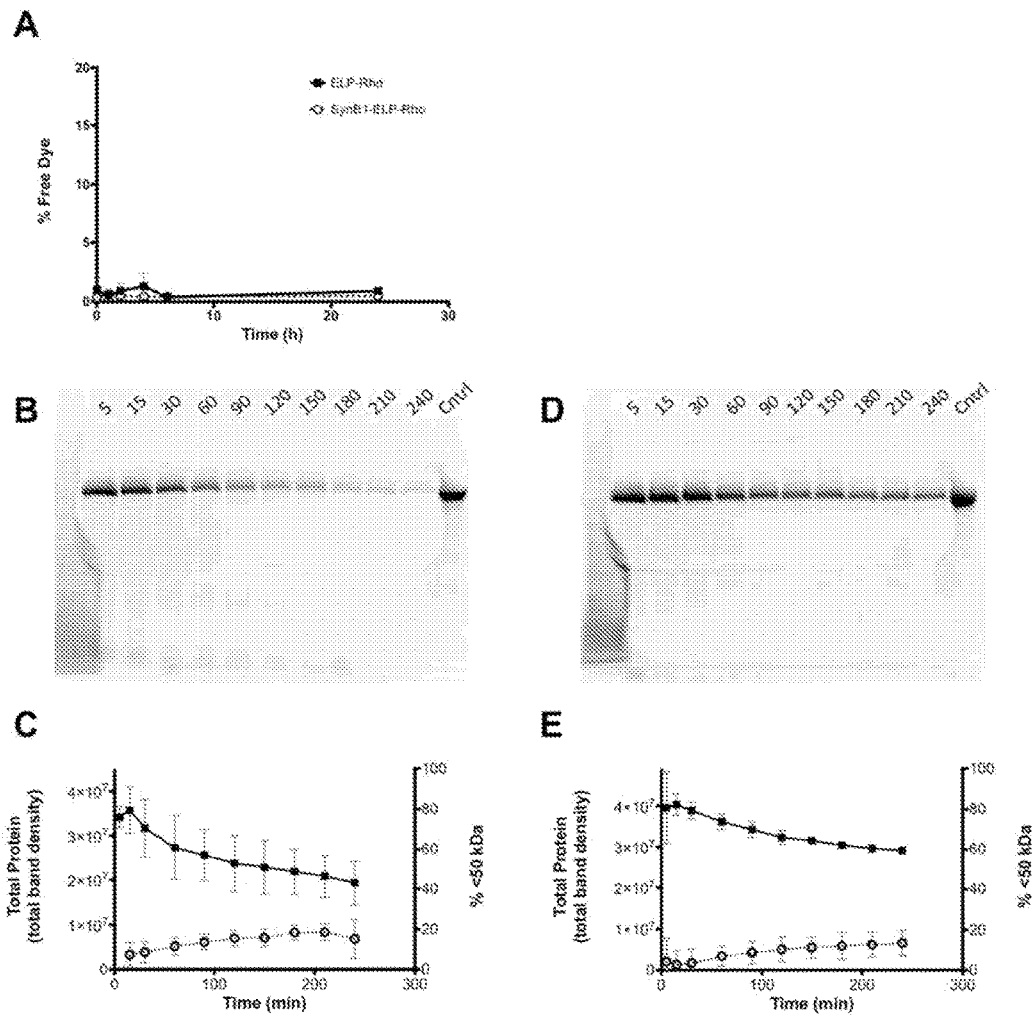
FIG. 4 includes graphs and images illustrating dye release and protein stability in plasma.

When using fluorescently labeled proteins, it is imperative that the label be stably bound in order to get accurate pharmacokinetic and biodistribution data. To determine the stability of the rhodamine label attached to the proteins via maleimide chemistry, the labeled protein is incubated in plasma from pregnant rats for various times at 37° C. After incubation, all proteins were precipitated using a 1:1 mixture with 10% trichloroacetic acid, and the fluorescence of the remaining supernatant was measured and compared to the pre-precipitation fluorescence. As shown in FIG. 4A, almost no label separated from the protein when incubated in rat plasma. Even after 24 h incubation, less than 2% of the dye was released from the protein. This demonstrates that the chemistry used to label these proteins is sufficient to produce a stable bond and confirms that the measurements are indeed of the labeled protein and not of released dye.

In addition to measuring dye release in vitro, the degradation of the protein in plasma samples in vivo is also examined. Plasma from the pharmacokinetic experiment above was analyzed by SDS-PAGE using direct fluorescence imaging to detect the labeled protein. As shown in FIGS. 4B and D, the total protein intensity decreased over time as the protein was cleared from circulation. However, very little protein degradation was apparent in either the ELP or the SynB1-ELP plasma samples. The amount of degradation was determined by measuring the total band intensity of the entire lane versus the total intensity of all bands <50 kDa. Plotting the total lane intensity (FIGS. 4C and E) revealed a clearance curve that closely overlayed the clearance seen with direct plasma fluorescence measurement. Analysis of the percentage of the band intensities at <50 kDa molecular weight revealed that very little degraded protein was present (right axis in FIGS. 4C and E). Even at the 4 hour time point, less than 20% of the total signal was present in these degraded bands. This analysis revealed that these proteins were quite stable in circulation.

Figure 3:
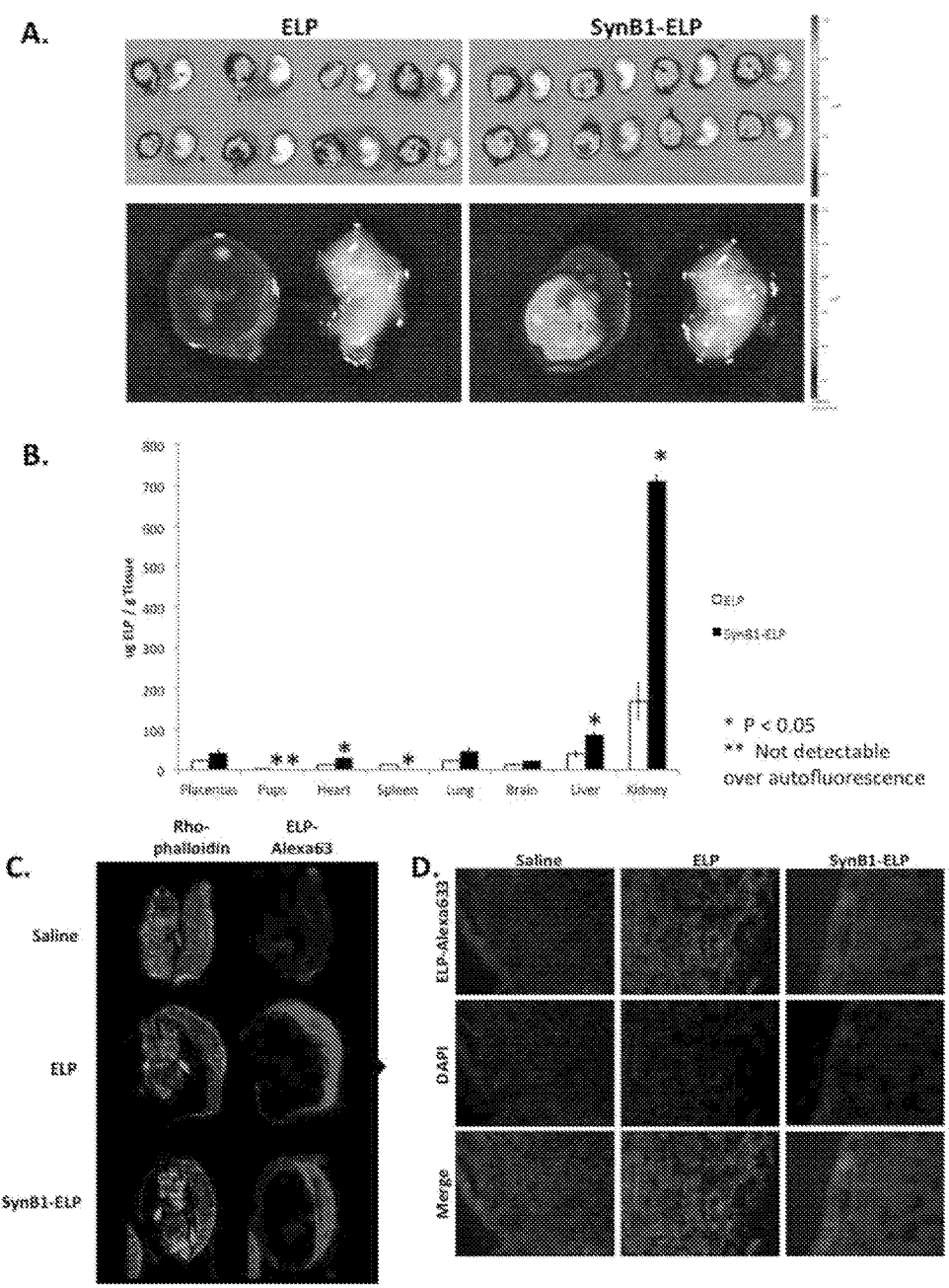
FIG. 3 includes a series of images and a graph illustrating placental distribution of ELP and SynB1-ELP.
Figure 5:
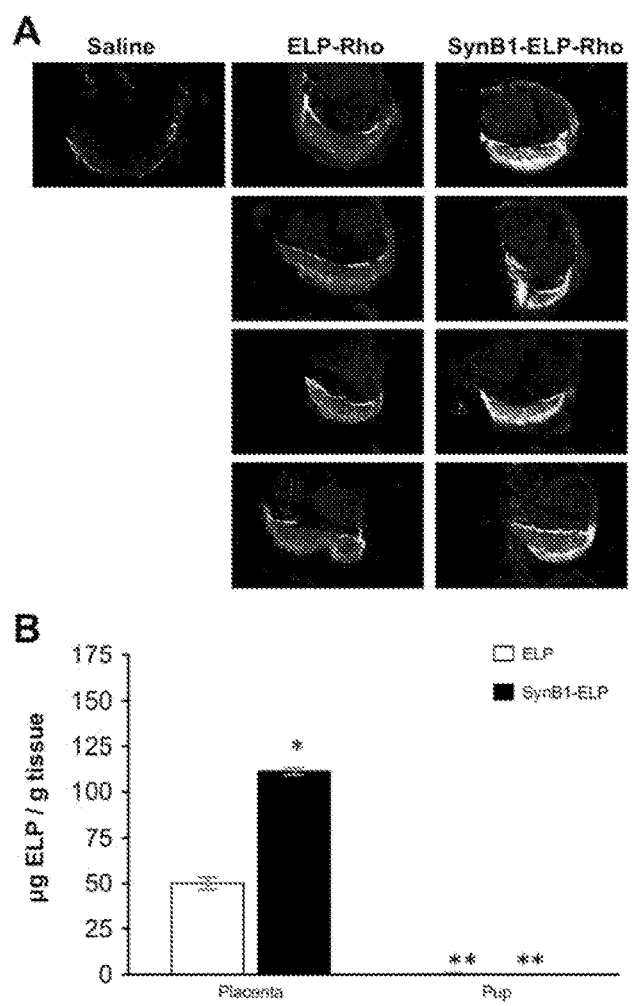
FIG. 5 includes image and bar graph showing Quantitative Fluorescence Histology of Feto-amnio-placental Units. Frozen feto-amnio-placental units were cut to 20 mm sections, and slides were scanned with a fluorescence slide scanner.

The ex vivo whole organ analysis shown in FIG. 3 above gives a good snapshot of the polypeptide's biodistribution and an estimate of the actual tissue polypeptide levels. However, due to differences in organ size and therefore variability in the transmission of light through the tissue, combined with the difficulty of creating appropriate standards to correctly assess the absorbance and scattering of light, this technique has a limited ability to assess absolute tissue polypeptide levels. Therefore, quantitative fluorescence analysis of placental and pup polypeptide levels is also carried out using cryosections of intact feto-amnio-placental units. By sectioning tissue and polypeptide standards to the same thickness, this technique allows for accurate quantitation of tissue polypeptide levels. As shown in FIG. 5A, this analysis confirmed that both polypeptides accumulated strongly in the placenta, but no polypeptide was detectable over autofluorescence in the pups. The images in FIG. 5A, all collected at the same scan settings, also indicate that SynB1-ELP accumulated at higher levels in the placenta than did ELP. The quantitative analysis revealed that ELP placental levels were approximately 50 µg/g of tissue (FIG. 5B). The placental level was increased over two-fold by the addition of the SynB1 CPP (p<0.0001). The quantitative fluorescence analysis also confirmed the fetal exclusion of both ELP and SynB1-ELP. Neither peptide was detectable in the pups using this method (FIG. 5B).

Figure 6:
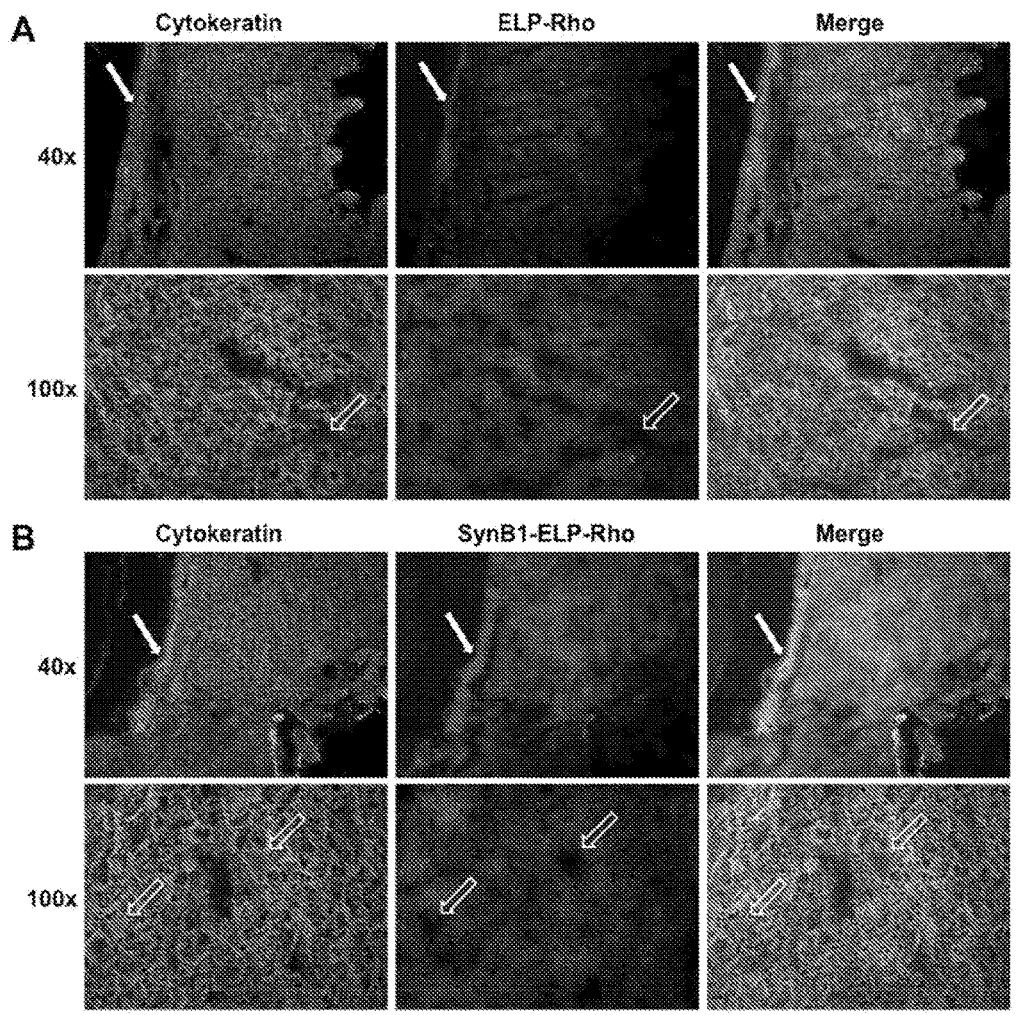
FIG. 6 includes images illustrating intra-placental distribution of ELPs. Slides of cryosections were immunostained with a cytokeratin antibody to mark trophoblast cells (green), and fluorescence of the rhodamine-labeled ELP (FIG. 6A) and SynB1-ELP (FIG. 6B) was detected (red). The 40× magnification shows polypeptide accumulation at the chorionic plate (solid arrows) and in the labyrinth. The 100× magnification shows polypeptide in the cytoplasm of trophoblast cells but excluded from the fetal chorionic villi (open arrows).

The placental tissue is also examined microscopically with a cytokeratin counterstain to detect trophoblast cells. Low magnification revealed that both ELP and SynB1-ELP accumulated highly at the chorionic plate (FIGS. 6A and B, solid arrows) and distributed diffusely within the labyrinth zone. Higher magnification revealed that both polypeptides accumulated in the cytoplasm of trophoblast cells. However, the interior of chorionic villi, which contain fetal blood and are detected by voids in the cytokeratin staining, contained no ELP or SynB1-ELP (open arrows in FIGS. 6A and B). These results confirm at the cellular level the observations from the whole-organ and cryosection imaging that the ELP-based drug carrier is capable of entering cytotrophoblasts in the placenta but is excluded from transport into fetal circulation.

Figure 7:
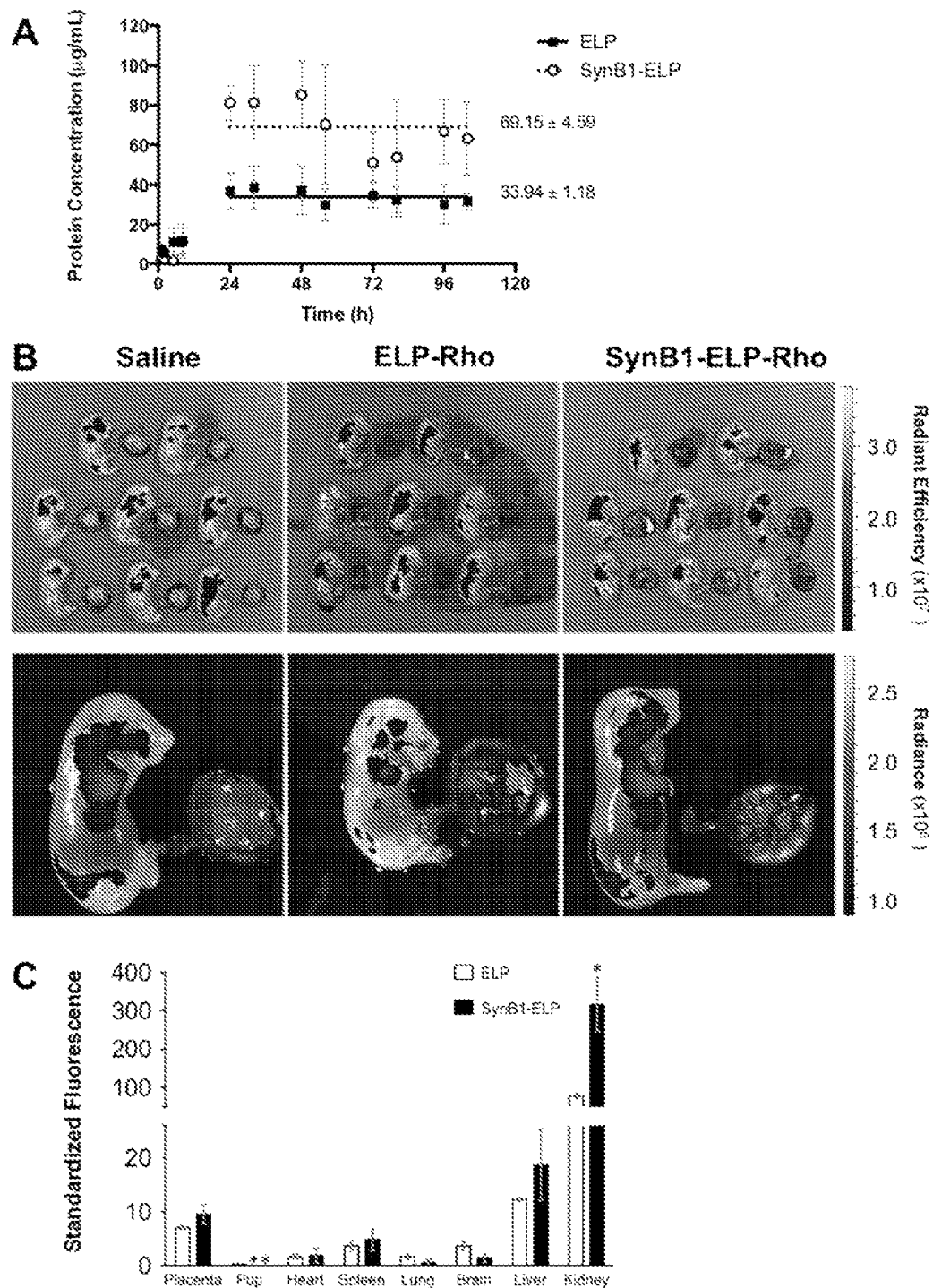
FIG. 7 includes images and graphs showing plasma levels and biodistribution of FLPs after Chronic Infusion.

Ex vivo whole organ and quantitative histological fluorescence analysis revealed that ELP and SynB1-ELP accumulate highly in the placenta but are excluded from the fetus four hours after bolus administration on GD14. Whether the fetal exclusion held after five days of continuous infusion of the polypeptides is also examined. ELP or SynB1-ELP was administered continuously from GD14 to GD19 using an IP minipump. As shown in FIG. 7A, this technique lead to a steady state plasma level of the polypeptides beginning 24 h after pump implantation. At the dose used (30 mg/kg/day), the plasma levels were maintained at 33.94 µg/mL for ELP and 69.15 µg/mL for SynB1-ELP. These plasma levels are a reflection of many in vivo kinetic processes, including the rate of transport from the peritoneal fluid to the blood, the rate of extravasation from the blood to the tissues, and the plasma clearance rate. Since SynB1-ELP has a longer terminal plasma half-life than ELP, this likely explains why there is a higher steady-state level of SynB1-ELP in the plasma than ELP. These plasma concentration data also provide useful information for the formulation of dosages when ELP is fused with therapeutic agents.

Ex vivo whole organ fluorescence analysis of the placentas is performed, pups, and organs on GD19 following five days of continuous polypeptide infusion. Relative to the acute experiment, the placental levels of the polypeptides were lower, which resulted from the difference in dose (100 mg/kg in the bolus dosing versus 30 mg/kg/day in the chronic infusion). However, similar to the acute data, the polypeptides accumulated at high levels in the placenta but were undetectable over autofluorescence in the pups (FIG. 7B). The kidneys still accumulated the most polypeptide, followed by the liver and the placenta (FIG. 7C). Also, after chronic infusion, the effect of the CPP on the polypeptide biodistribution was much less pronounced. Only the kidneys contained significantly more SynB1-ELP than ELP (kidney levels of SynB1-ELP were increased four-fold relative ELP kidney levels, p=0.01). This indicates that the increases seen in the tissues immediately after infusion were the result of faster tissue deposition kinetics for SynB1-ELP relative to ELP, and after chronic administration, the tissue levels of the two polypeptides eventually became equivalent (with the exception of the kidneys).

In summary, this work has shown that the ELP and CPP-ELP carrier do not cross the placental barrier, even after five days of continuous infusion. These data demonstrate that a CPP can be used to direct intracellular delivery of the drug carrier within the placenta without affecting the penetration into the fetus.

Example 4. ELP-Delivered VEGF

The coding sequence for VEGF was amplified from a human cDNA for VEGF-A. The sequence was modified by addition of C-terminal amino acids to generate a sequence identical to $VEGF_{121}$ and to add restriction sites for cloning into the ELP expression vector. The coding sequence was cloned in frame with the ELP coding sequence to generate the ELP-VEGF chimeric construct. ELP-VEGF was expressed in *E. coli* BL21-Rosetta cells using the pET expression system with IPTG induction, and ELP-VEGF was purified by three to five rounds of inverse transition cycling (Bidwell G L, 3rd, et al., *Mol Cancer Ther,* 2005; Meyer D E, et al., 1999), taking advantage of the thermally responsive nature of ELP. The result was a 73 kDa protein that was very pure (FIG. 8).

This example demonstrates that the ELP-VEGF was active and that ELP fusion did not alter the potency of VEGF. Proliferation of human umbilical vein endothelial cells (HUVECs) is stimulated when the cell are exposed to VEGF. As shown in FIG. 9, both free recombinant VEGF and ELP-VEGF stimulated HUVEC proliferation with equal potency. Furthermore, ELP-VEGF activated tube formation in HUVECs plated on growth factor reduced Matrigel, and the potency was again similar to or even slightly superior to that of free VEGF (FIGS. 10A and B). Finally, ELP-VEGF induced HUVEC migration in a Matrigel transwell cell migration assay with a similar potency as free VEGF (FIGS. 11A and B). These data indicate that a purified and highly potent ELP-VEGF chimeric protein is obtained, and the next phase of its preclinical testing is poised to carry out.

In addition to examining the ELP-VEGF activity in vitro, the pharmacokinetics (PK) and biodistribution of ELP-VEGF in comparison to free $VEGF_{121}$ is also determined. Both free $VEGF_{121}$ and ELP-VEGF were fluorescently labeled, and their PK and biodistribution were determined in mice after bolus intravenous administration. Free $VEGF_{121}$ had a very rapid plasma clearance (FIG. 12A), and fitting to a 2-compartment PK model revealed a terminal plasma half-life of approximately 30 minutes. This is consistent with other reports of approximately a 30 minute half-life for recombinant VEGF in humans. ELP-VEGF cleared more slowly than free $VEGF_{121}$ (FIG. 12A). The plasma clearance rate of ELP-VEGF after IV infusion was about half the rate of free $VEGF_{121}$ (FIG. 12B), and as a result, there was less fluorescence detectable in the urine at the end of the experiment (FIG. 12C). Four hours after the infusion, the biodistribution was determined by ex vivo whole organ fluorescence imaging. $VEGF_{121}$ accumulated most highly in the kidneys and the liver and had very low levels in other organs. In contrast, ELP-VEGF accumulated more highly in the spleen and liver than did free $VEGF_{121}$, and the kidney deposition of ELP-VEGF was significantly lower than for free $VEGF_{121}$ (FIG. 12D).

Whether ELP-VEGF was effective for lowering blood pressure in a rat model of preeclampsia is texted next. Pregnant rats at gestational day 14 (GD14) were subjected to surgery to reduce ale blood flow to the placentas. It has previously been shown that this model, achieved by partially restricting the ovarian arteries and the dorsal aorta, results in a preeclampsia-like syndrome in the rat. The effects mirror human preeclampsia in that the rats develop hypertension, proteinuria, reduced renal function, fetal growth restriction, and some fetal loss. The model also induces molecular markers that mirror the human syndrome, including elevated sFlt-1 levels, increased pro-inflammatory cytokines, and increased placental reactive oxygen species. The hypertension associated with this model can be seen in FIG. 13, where the mean arterial pressure increased from about 105 mmHg in normal pregnant rats on GD19 to over 120 mmHg in the preeclampsia model as measured by a pressure transducer inserted into a carotid arterial catheter. When ELP-VEGF was administered at a low dose of 1 mg/kg/day using an intraperitoneal minipump from GD14 to GD19, it effectively lowered the blood pressure of the preeclampsia-induced rats to near normal levels.

Example 5. ELP-Delivered NF-κB Inhibitory Peptide

This investigation has developed an ELP-fused peptide inhibitor of activated NF-κB. NF-κB activation upon extracellular signaling is mediated by phosphorylation and release of the natural inhibitor I-κB from the NF-κB p50/p65 heterodimer. I-κB release exposes a nuclear localization sequence (NLS) on the p50 subunit of NF-κB, and once exposed, this NLS mediates nuclear import of NF-κB. Once inside the nucleus, NF-κB binds to response elements on its target genes and regulates gene expression. A synthetic cell permeable peptide containing the p50 NLS is capable of blocking the nuclear import of NF-κB upon stimulation in a variety of cell lines (Lin Y Z, et al., 1995). A copy of the p50 NLS is fused to the SynB1-ELP carrier and validated its activity using an in vitro NF-κB activation assay. Stimulation of cultured HUVECs with TNF-α leads to rapid activation of the NF-κB pathway, and this can be detected by monitoring nuclear localization of NF-κB (FIG. 14A, left panel). As shown in FIG. 14, pretreatment of the cells with SynB-ELP-p50, but not the SynB1-ELP control polypeptide, completely blocks this nuclear translocation of NF-κB (FIG. 14A, middle and right panels, quantified in 30-60 cells/sample in FIG. 14B).

TNFα stimulation also leads to the secretion of the vasoactive peptide endothelin-1 by HUVECs. This endothelin release contributes to the hypertension associated with the pro-inflammatory environment in preeclampsia. As shown in FIG. 15, endothelin levels in the culture media increase about three-fold when the cells are stimulated with TNFα. However, when the cells are pre-treated with the SynB1-ELP-p50 peptide, the endothelin release is completely blocked. In addition, SynB1-EIT-p50 decreases the endothelin release from unstimulated HUVECs.

To test whether the NF-κB inhibitory polypeptide had any effect on proliferation of normal tissue cell types, were determined its effects on proliferation of endothelial and chorionic cells. As shown in FIG. 16, HUVEC endothelial cells and BeWo chorionic cells were exposed to the indicated concentrations of SynB1-ELP or SynB1-ELP-p50 for 72 h, and cell number was determined by MTS assay. Neither SynB1-ELP or SynB1-ELP-p50 had any detectable effect on proliferation of HUVEC or BeWo cells at concentrations up to 50 μM. These data indicate that an active NF-κB inhibitory polypeptide with potent anti-inflammatory and anti-hypertensive properties and low cytotoxicity has been synthesized and purified.

Using pregnant Sprague Dawley rats, the pharmacokinetics and biodistribution of the SynB1-ELP-delivered p50 peptide with the free p50 peptide is determined. Rats were given a single bolus dose of 100 mg/kg of rhodamine-labeled SynB1-ELP-p50 or free p50, blood was sampled intermittently for four hours, and organs, placentas, and pups were removed for ex vivo fluorescence analysis. As shown in FIG. 17, SynB1-ELP delivery had massive effects in the pharmacokinetics and the biodistribution of the p50 peptide. Initial plasma levels of the p50 peptide were about 100-fold lower than SynB1-ELP-p50 levels, indicated very rapid clearance of the majority of the injected peptide. Also, when the plasma clearance data were fit to a two-compartment pharmacokinetic model, the p50 peptide cleared with a terminal half-life of 21 minutes, whereas SynB1-ELP-p50 had a terminal half-life of greater than two hours (FIG. 17A). Placenta and pups levels were determined four hours after injection by ex vivo fluorescence analysis. As shown in FIG. 17B, total placental levels of the free p50 peptide were thirty fold lower than placental SynB1-ELP-p50 levels. Importantly, in addition to vastly lower therapeutic levels in the placenta, the unconjugated p50 peptide freely entered the fetal circulation and was visible in the pups. These data indicate that ELP fusion greatly enhances the plasma half-life and tissue levels of a therapeutic peptide, and it effectively prevents the peptide from entering the fetal circulation.

Example 6. ELP-Delivered NADPH Oxidase Inhibitory Peptide

The cell penetrating NADPH oxidase inhibitory polypeptide was generated by modifying the coding sequence for ELP with the addition of the coding sequence for the SynB1 CPP at its N-terminus and with the coding sequence for the NOX inhibitory peptide at its C-terminus. A DNA cassette encoding the SynB1 and NOX peptides separated by an SfiI restriction site and containing sticky ends compatible with NdeI and BamHI restriction sites was synthesized (Integrated DNA Technologies). The cassette was cloned into pET25b between the NdeI and BamHI restriction sites. The coding sequence for ELP was restricted from its pUC19 host vector using PflMI and BglI, the DNA was gel purified, and it was ligated into the SfiI site of the modified pET25b vector. The result was an in-frame fusion of SynB1, ELP, and the NOX peptide (SynB1-ELP-NOX). The final construct was confirmed by DNA sequencing and transformed into the BLR(DE3) expression strain (Novagen). A construct containing the SynB1 peptide fused to the N-terminus of ELP, but lacking the NOX peptide (SynB1-ELP) was generated in a similar manner. Polypeptides were purified by three to five rounds of inverse transition cycling.

It is confirmed that the SynB1-ELP-NOX polypeptide was internalized by cells. Both endothelial cells (HUVECs) and chorionic cells (BeWo choriocarcinoma cells) were exposed to fluorescently labeled SynB1-ELP-NOX for 1 h. The cells were then washed and given fresh media for 24 h. Internalization was confirmed by fluorescence microscopy as shown in FIG. 18. The SynB1-ELP-NOX polypeptide was detectable in a punctate cytoplasmic distribution in both cell lines.

Next, the ability of the SynB1-ELP-NOX polypeptide to block ROS production in placental chorionic villous explants is demonstrated. Chorionic villous explants were cut on GD19 and cultured ex vivo on Matrigel coated wells with complete cell culture medium. After equilibration, culture medium was replaced with medium containing SynB1-ELP-NOX or the SynB1-ELP control polypeptides at 20 or 50 µM, and explants were incubated at 6% $O_2$ (representing a healthy placenta) or 1% $O_2$ (representing a preeclamptic placenta). After 48 h exposure to hypoxia, detection of ROS was performed using the dihydroethidium (DHE) assay. As shown in FIG. 19, explants cultured at 1% $O_2$ produced more ROS than explants cultured at 6% $O_2$. Incubation with SynB1-ELP-NOX inhibited this ROS production and even resulted in ROS levels in hypoxic explants that were lower than normoxic controls. The SynB1-ELP polypeptide that lacks the NOX inhibitory domain had no effect on ROS production. These results demonstrate that SynB1-ELP-NOX can block NADPH oxidase induces ROS production, and they show the promise of this agent for therapy of ROS-driven diseases.

Example 7. Using Cell Penetrating Peptides and Organ Targeting Peptides to Direct ELP's Biodistribution For various diseases, it is often beneficial to deliver therapeutics to specific organs of interest. Organ targeting can increase the efficacy of the delivered therapeutic, and it can reduce off-target side effects. For treatment of preeclampsia, which mediated by factors produced in the placenta which act in systemic vascular beds and in the kidney, it would be beneficial to deliver pro-angiogenic, anti-inflammatory, or anti-oxidant therapeutics to both the placenta and the kidneys. ELP naturally accumulates at high levels in the kidneys, and FIGS. 3 and 17 above show that ELP or a CPP-fused ELP accumulates at high levels in the placenta. Here, it is sought to optimize the kidney targeting by testing multiple CPPs and by testing a peptide designed to target the vascular endothelium of the kidney (kidney targeting peptide (KTP)). Sprague Dawley rats were administered ELP, the CPP-fused ELPs Tat-ELP and SynB1-ELP, or the kidney targeting peptide-fused KTP-ELP by bolus IV injection. Plasma was sampled intermittently for four hours, then organs were removed and analyzed by ex vivo fluorescence imaging. The CPPs or KTP did not have dramatic effects on the plasma clearance rate of ELP (not shown), but the peptides did dramatically alter the biodistribution. All three peptides increased ELP deposition in the kidney by over five-fold (FIGS. 20A and B). Also, the CPPs Tat and SynB1 increased ELP deposition in the liver. When kidney specificity was assessed by measuring kidney: liver and kidney: heart ratios, KTP was found to be the most specific peptide for targeting the kidney (inducing a three-fold enhancement of ELP levels relative to the liver and over 15-fold enhancement relative to the heart). These data demonstrate that cell penetrating peptides and organ targeting peptides can be employed to direct the biodistribution of the ELP drug carrier.

Throughout this document, various references are mentioned. All such references are incorporated herein by reference, including the references set forth in the following list.

REFERENCES

1. Clark D E, Smith S K, He Y, et al. A vascular endothelial growth factor antagonist is produced by the human placenta and released into the maternal circulation. *Biology of reproduction*. December 1998; 59(6):1540-1548.
2. Banai S, Jaklitsch M T, Shou M, et al. Angiogenic-induced enhancement of collateral blood flow to ischemic myocardium by vascular endothelial growth factor in dogs. *Circulation*. May 1994; 89(5):2183-2189.
3. Pearlman J D, Hibberd M G, Chuang M L, et al. Magnetic resonance mapping demonstrates benefits of VEGF-induced myocardial angiogenesis. *Nat Med*. October 1995; 1(10):1085-1089.
4. Chade A R, Kelsen S. Reversal of renal dysfunction by targeted administration of VEGF into the stenotic kidney: a novel potential therapeutic approach. *American journal of physiology. Renal physiology*. May 15, 2012; 302(10): F1342-1350.
5. Chade A R. VEGF: Potential therapy for renal regeneration. *F1000 medicine reports,* 2012; 4:1.
6. Cvetanovic M, Patel J M, Marti H H, Kini A R, Opal P. Vascular endothelial growth factor ameliorates the ataxic phenotype in a mouse model of spinocerebellar ataxia type 1. *Nat Med*. 2011; 17(11):1445-1447.
7. Eppler S M, Combs D L, Henry T D, et al. A target-mediated model to describe the pharmacokinetics and hemodynamic effects of recombinant human vascular endothelial growth factor in humans. *Clinical pharmacology and therapeutics*. July 2002; 72(1):20-32.
8. Miquerol L, Langille B L, Nagy A. Embryonic development is disrupted by modest increases in vascular endothelial growth factor gene expression. *Development*. September 2000; 127(18):3941-3946.
9. Drake C J, Little C D. Exogenous vascular endothelial growth factor induces malformed and hyperfused vessels during embryonic neovascularization. *Proc Natl Acad Sci USA*. Aug. 15, 1995; 92(17):7657-7661.
10. He Y, Smith S K, Day K A, Clark D E, Licence D R, Charnock-Jones D S. Alternative splicing of vascular endothelial growth factor (VEGF)-R1 (FLT-1) pre-mRNA is important for the regulation of VEGF activity. *Mol Endocrinol*. April 1999; 13(4):537-545.
11. Makarov S S. NF-kappa B in rheumatoid arthritis: a pivotal regulator of inflammation, hyperplasia, and tissue destruction. *Arthritis research*. 2001; 3(4):200-206.

12. Lin Y Z, Yao S Y, Veach R A, Torgerson T R, Hawiger J. Inhibition of nuclear translocation of transcription factor NF-kappa B by a synthetic peptide containing a cell membrane-permeable motif and nuclear localization sequence. *J Biol Chem*. Jun. 16, 1995; 270(24):14255-14258.
13. Paravicini T M, Touyz R M. NADPH oxidases, reactive oxygen species, and hypertension: clinical implications and therapeutic possibilities. *Diabetes care*. February 2008; 31 Suppl 2:S170-180.
14. Park Y M, Febbraio M, Silverstein R L. CD36 modulates migration of mouse and human macrophages in response to oxidized LDL and may contribute to macrophage trapping in the arterial intima. *J Clin Invest*. January 2009; 119(1):136-145.
15. Radermacher K A, Wingler K, Langhauser F, et al. Neuroprotection After Stroke by Targeting NOX4 As a Source of Oxidative Stress. *Antioxidants & redox signaling*. Apr. 20, 2013; 18(12):1418-1427.
16. Matsubara S, Sato I. Enzyme histochemically detectable NAD(P)H oxidase in human placental trophoblasts: normal, preeclamptic, and fetal growth restriction-complicated pregnancy. *Histochemistry and cell biology*. July 2001; 116(1):1-7.
17. Khan S R. Reactive oxygen species as the molecular modulators of calcium oxalate kidney stone formation: evidence from clinical and experimental investigations. *J Urol*. March 2013; 189(3):803-811.
18. Block M L. NADPH oxidase as a therapeutic target in Alzheimer's disease. *BMC neuroscience*. 2008; 9 Suppl 2:S8.
19. Wang X, Pinto-Duarte A, Sejnowski T J, Behrens M M. How Nox2-Containing NADPH Oxidase Affects Cortical Circuits in the NMDA Receptor Antagonist Model of Schizophrenia. *Antioxidants & redox signaling*. Apr. 20, 2013; 18(12):1444-1462.
20. Whitehead N P, Yeung E W, Froehner S C, Allen D G. Skeletal muscle NADPH oxidase is increased and triggers stretch-induced damage in the mdx mouse. *PloS one*. 2010; 5(12):e15354.
21. Monaghan-Benson E, Hartmann J, Vendrov A E, et al. The role of vascular endothelial growth factor-induced activation of NADPH oxidase in choroidal endothelial cells and choroidal neovascularization. *Am J Pathol*. October 2010; 177(4):2091-2102.
22. Araneda O F, Tuesta M. Lung oxidative damage by hypoxia. *Oxidative medicine and cellular longevity*. 2012; 2012: 856918.
23. Cifuentes-Pagano E, Csanyi G, Pagano P J. NADPH oxidase inhibitors: a decade of discovery from Nox2ds to HTS. *Cell Mol Life Sci*. July 2012; 69(14):2315-2325.
24. Csanyi G, Cifuentes-Pagano E, Al Ghouleh I, et al. Nox2 B-loop peptide, Nox2ds, specifically inhibits the NADPH oxidase Nox2. *Free Radic Biol Med*. Sep. 15, 2011; 51(6):1116-1125.
25. Moktan S, Perkins E, Kratz F, Raucher D. Thermal targeting of an acid-sensitive doxorubicin conjugate of elastin-like polypeptide enhances the therapeutic efficacy compared with the parent compound in vivo. *Mol Cancer Ther*. July 2012; 11(7):1547-1556.
26. Moktan S, Ryppa C, Kratz F, Raucher D. A thermally responsive biopolymer conjugated to an acid-sensitive derivative of paclitaxel stabilizes microtubules, arrests cell cycle, and induces apoptosis. *Invest New Drugs*. Oct. 12, 2010.
27. Bidwell G L, Perkins E, Hughes J, Khan M, James J, Raucher D. Thermally Targeted Delivery of a c-Myc inhibitory Polypeptide Inhibits Tumor Progression and Extends Survival in a Rat Glioma Model. *PloS one*. 2013; In Press.
28. Bidwell G L, 3rd, Perkins E, Raucher D. A thermally targeted c-Myc inhibitory polypeptide inhibits breast tumor growth. *Cancer Lett*. Jun. 28, 2012; 319(2):136-143.
29. Urry D W, Parker T M, Reid M C, Gowda D C. *Bioact Compat Polym*. 1991; 6(3):263-282.
30. Bidwell G L. Peptides for Cancer Therapy—A Drug Development Opportunity and a Drug Delivery Challenge. *Therapeutic Delivery*. 2012; in press.
31. Bidwell G L, 3rd, Raucher D. Application of thermally responsive polypeptides directed against c-Myc transcriptional function for cancer therapy. *Mol Cancer Ther*. July 2005; 4(7):1076-1085.
32. Bidwell G L, 3rd, Raucher D. Cell penetrating elastin-like polypeptides for therapeutic peptide delivery. *Adv Drug Deliv Rev*. Dec. 30, 2010; 62(15):1486-1496.
33. Bidwell G L, 3rd, Whittom A A, Thomas E, Lyons D, Hebert M D, Raucher D. A thermally targeted peptide inhibitor of symmetrical dimethylation inhibits cancer-cell proliferation. *Peptides*. May 2010; 31(5):834-841.
34. Massodi I, Bidwell G L, 3rd, Raucher D. Evaluation of cell penetrating peptides fused to elastin-like polypeptide for drug delivery. *J Control Release*. Nov. 28, 2005; 108(2-3):396-408.
35. Massodi I, Thomas E, Raucher D. Application of thermally responsive elastin-like polypeptide fused to a lactoferrin-derived peptide for treatment of pancreatic cancer. *Molecules*. 2009; 14(6):1999-2015.
36. Meyer D E, Chilkoti A. Purification of Recombinant Proteins by Fusion with Thermally Responsive Polypeptides. *Nat. Biotechnol*. 1999; 17:1112-1115.
37. Moktan S, Raucher D. Anticancer activity of proapoptotic peptides is highly improved by thermal targeting using elastin-like polypeptides. *International journal of peptide research and therapeutics*. September 2012; 18(3):227-237.
38. Bidwell G L, 3rd, Davis A N, Raucher D. Targeting a c-Myc inhibitory polypeptide to specific intracellular compartments using cell penetrating peptides. *J Control Release*. Apr. 2, 2009; 135(1):2-10.
39. Luan C H, Parker T M, Gowda D C, Urry D W. Hydrophobicity of amino acid residues: differential scanning calorimetry and synthesis of the aromatic analogues of the polypentapeptide of elastin. *Biopolymers*. September 1992; 32(9):1251-1261.
40. Luan C H, Parker T M, Prasad K U, Urry D W. Differential scanning calorimetry studies of NaCl effect on the inverse temperature transition of some elastin-based polytetra-, polypenta-, and polynonapeptides. *Biopolymers*. April 1991; 31(5):465-475.
41. Urry D W, Long M M, Cox B A, Ohnishi T, Mitchell L W, Jacobs M. The synthetic polypentapeptide of elastin coacervates and forms filamentous aggregates. *Biochim Biophys Acta*. Dec. 18, 1974; 371(2):597-602.
42. Meyer D E, Kong G A, Dewhirst M W, Zalutsky M R, Chilkoti A. Targeting a Genetically Engineered Elastin-like Polypeptide to Solid Tumors by Local Hyperthermia. *Cancer Res*. Feb. 15, 2001 2001; 61(4):1548-1554.
43. Meyer D E, Shin B C, Kong G A, Dewhirst M W, Chilkoti A. Drug targeting using thermally responsive polymers and local hyperthermia. *J Control Release*. Jul. 6, 2001; 74(1-3):213-224.
44. Dreher M R, Raucher D, Balu N, Michael Colvin O, Ludeman S M, Chilkoti A. Evaluation of an elastin-like polypeptide-doxorubicin conjugate for cancer therapy. *J Control Release*. Aug. 28, 2003; 91(1-2):31-43.

45. Massodi I, Moktan S, Rawat A, Bidwell G L, 3rd, Raucher D. Inhibition of ovarian cancer cell proliferation by a cell cycle inhibitory peptide fused to a thermally responsive polypeptide carrier. *Int J Cancer*. Jan. 15, 2010; 126(2):533-544.

46. Furgeson D Y, Dreher M R, Chilkoti A. Structural optimization of a "smart" doxorubicin-polypeptide conjugate for thermally targeted delivery to solid tumors. *J Control Release*. Jan. 10, 2006; 110(2):362-369.

47. Bidwell G L, 3rd, Davis A N, Fokt I, Priebe W, Raucher D. A thermally targeted elastin-like polypeptide-doxorubicin conjugate overcomes drug resistance. *Invest New Drugs*. August 2007; 25(4):313-326.

48. Bidwell G L, 3rd, Fokt I, Priebe W, Raucher D. Development of elastin-like polypeptide for thermally targeted delivery of doxorubicin. *Biochem Pharmacol*. Mar. 1, 2007; 73(5):620-631.

49. Massodi I, Bidwell G L, 3rd, Davis A, et al. Inhibition of ovarian cancer cell metastasis by a fusion polypeptide Tat-ELP. *Clin Exp Metastasis*. 2009; 26(3):251-260.

50. Liu W, Mackay J A, Dreher M R, et al. Injectable intratumoral depot of thermally responsive polypeptide-radionuclide conjugates delays tumor progression in a mouse model. *J Control Release*. Jan. 31, 2010; in press.

51. Liu W, McDaniel J, Li X, et al. Brachytherapy using injectable seeds that are self-assembled from genetically encoded polypeptides in situ. *Cancer Res*. Nov. 15, 2012; 72(22):5956-5965.

52. MacKay J A, Chen M, McDaniel J R, Liu W, Simnick A J, Chilkoti A. Self-assembling chimeric polypeptide-doxorubicin conjugate nanoparticles that abolish tumors after a single injection. *Nat Mater*. December 2009; 8(12):993-999.

53. Simnick A J, Amiram M, Liu W, et al. In vivo tumor targeting by a NGR-decorated micelle of a recombinant diblock copolypeptide. *J Control Release*. Oct. 30, 2011; 155(2):144-151.

54. Na K, Lee S A, Jung S H, Hyun J, Shin B C. Elastin-like polypeptide modified liposomes for enhancing cellular uptake into tumor cells. *Colloids and surfaces. B, Biointerfaces*. Mar. 1, 2012; 91:130-136.

55. Callahan D J, Liu W, Li X, et al. Triple stimulus-responsive polypeptide nanoparticles that enhance intratumoral spatial distribution. *Nano letters*. Apr. 11, 2012; 12(4):2165-2170.

56. McDaniel J R, Macewan S R, Dewhirst M, Chilkoti A. Doxorubicin-conjugated chimeric polypeptide nanoparticles that respond to mild hyperthermia. *J Control Release*. May 10, 2012; 159(3):362-367.

57. Walker L, Perkins E, Kratz F, Raucher D. Cell penetrating peptides fused to a thermally targeted biopolymer drug carrier improve the delivery and antitumor efficacy of an acid-sensitive doxorubicin derivative. *Int J Pharm*. Oct. 15, 2012; 436(1-2):825-832.

58. Betre H, Setton L A, Meyer D E, Chilkoti A. Characterization of a genetically engineered elastin-like polypeptide for cartilaginous tissue repair. *Biomacromolecules*. September-October 2002; 3(5):910-916.

59. McHale M K, Setton L A, Chilkoti A. Synthesis and in vitro evaluation of enzymatically cross-linked elastin-like polypeptide gels for cartilaginous tissue repair. *Tissue engineering*. November-December 2005; 11(11-12):1768-1779.

60. Shamji M F, Chen J, Friedman A H, Richardson W J, Chilkoti A, Setton L A. Synthesis and characterization of a thermally-responsive tumor necrosis factor antagonist. *J Control Release*. Aug. 7, 2008; 129(3):179-186.

61. Shamji M F, Jing L, Chen J, et al. Treatment of neuroinflammation by soluble tumor necrosis factor receptor Type II fused to a thermally responsive carrier. *Journal of neurosurgery. Spine*. August 2008; 9(2):221-228.

62. Moss I L, Gordon L, Woodhouse K A, Whyne C M, Yee A J. A novel thiol-modified hyaluronan and elastin-like polypeptide composite material for tissue engineering of the nucleus pulposus of the intervertebral disc. *Spine*. June 2011; 36(13):1022-1029.

63. Dreher M R, Elas M, Ichikawa K, et al. Nitroxide conjugate of a thermally responsive elastin-like polypeptide for noninvasive thermometry. *Med Phys*. October 2004; 31(10):2755-2762.

64. Chen T H, Bae Y, Furgeson D Y. Intelligent biosynthetic nanobiomaterials (IBNs) for hyperthermic gene delivery. *Pharm Res*. March 2008; 25(3):683-691.

65. Conrad U, Plagmann I, Malchow S, et al. ELPylated anti-human TNF therapeutic single-domain antibodies for prevention of lethal septic shock. *Plant biotechnology journal*. January 2011; 9(1):22-31.

66. Na K, Jung J, Lee J, Hyun J. Thermoresponsive pore structure of biopolymer microspheres for a smart drug carrier. *Langmuir: the ACS journal of surfaces and colloids*. Jul. 6, 2010; 26(13):11165-11169.

67. Blit P H, McClung W G, Brash J L, Woodhouse K A, Santerre J P. Platelet inhibition and endothelial cell adhesion on elastin-like polypeptide surface modified materials. *Biomaterials*. September 2011; 32(25):5790-5800.

68. Hearst S M, Walker L R, Shao Q, Lopez M, Raucher D, Vig P J. The design and delivery of a thermally responsive peptide to inhibit S100B-mediated neurodegeneration. *Neuroscience*. Dec. 1, 2011; 197:369-380.

69. Chen T H, Bae Y, Furgeson D Y, Kwon G S. Biodegradable hybrid recombinant block copolymers for non-viral gene transfection. *Int J Pharm*. May 1, 2012; 427(1):105-112.

70. Amruthwar S S, Puckett A D, Janorkar A V. Preparation and characterization of novel elastin-like polypeptide-collagen composites. *J Biomed Mater Res A*. Feb. 20, 2013.

71. Amruthwar S S, Janorkar A V. In vitro evaluation of elastin-like polypeptide-collagen composite scaffold for bone tissue engineering. *Dental materials: official publication of the Academy of Dental Materials*. February 2013; 29(2):211-220.

72. Lee K M, Jung G S, Park J K, Choi S K, Jeon W B. Effects of Arg-Gly-Asp-modified elastin-like polypeptide on pseudoislet formation via up-regulation of cell adhesion molecules and extracellular matrix proteins. *Acta Biomater*. March 2013; 9(3):5600-5608.

73. Amiram M, Luginbuhl K M, Li X, Feinglos M N, Chilkoti A. Injectable protease-operated depots of glucagon-like peptide-1 provide extended and tunable glucose control. *Proc Natl Acad Sci USA*. Feb. 19, 2013; 110(8):2792-2797.

74. Senger D R, Galli S J, Dvorak A M, Perruzzi C A, Harvey V S, Dvorak H F. Tumor cells secrete a vascular permeability factor that promotes accumulation of ascites fluid. *Science*. Feb. 25, 1983; 219(4587):983-985.

75. Hayden M S, Ghosh S. Shared principles in NF-kappaB signaling. *Cell*. Feb. 8, 2008; 132(3):344-362.

76. May M J, D'Acquisto F, Madge L A, Glockner J, Pober J S, Ghosh S. Selective inhibition of NF-kappaB activation by a peptide that blocks the interaction of NEMO with the IkappaB kinase complex. *Science*. Sep. 1, 2000; 289(5484):1550-1554.

77. Dasgupta S, Jana M, Zhou Y, Fung Y K, Ghosh S, Pahan K. Antineuroinflammatory effect of NF-kappaB essential modifier-binding domain peptides in the adoptive transfer model of experimental allergic encephalomyelitis. *J Immunol*. Jul. 15, 2004; 173(2):1344-1354.

78. di Meglio P, Ianaro A, Ghosh S. Amelioration of acute inflammation by systemic administration of a cell-permeable peptide inhibitor of NF-kappaB activation. *Arthritis Rheum*. March 2005; 52(3):951-958.

79. Tas S W, Vervoordeldonk M J, Hajji N, May M J, Ghosh S, Tak P P. Local treatment with the selective IkappaB kinase beta inhibitor NEMO-binding domain peptide ameliorates synovial inflammation. *Arthritis Res Ther*. 2006; 8(4):R86.

80. Ghosh A, Roy A, Liu X, et al. Selective inhibition of NF-kappaB activation prevents dopaminergic neuronal loss in a mouse model of Parkinson's disease. *Proc Natl Acad Sci USA*. Nov. 20, 2007; 104(47):18754-18759.

81. Rehman K K, Bertera S, Bottino R, et al. Protection of islets by in situ peptide-mediated transduction of the Ikappa B kinase inhibitor Nemo-binding domain peptide. *J Biol Chem*. Mar. 14, 2003; 278(11):9862-9868.

82. Thomas R P, Farrow B J, Kim S, May M J, Hellmich M R, Evers B M. Selective targeting of the nuclear factor-kappaB pathway enhances tumor necrosis factor-related apoptosis-inducing ligand-mediated pancreatic cancer cell death. *Surgery*. August 2002; 132(2):127-134.

83. Biswas D K, Shi Q, Baily S, et al. NF-kappa B activation in human breast cancer specimens and its role in cell proliferation and apoptosis. *Proc Natl Acad Sci USA*. Jul. 6, 2004; 101(27):10137-10142.

84. Tapia M A, Gonzalez-Navarrete I, Dalmases A, et al. Inhibition of the canonical IKK/NF kappa B pathway sensitizes human cancer cells to doxorubicin. *Cell Cycle*. Sep. 15, 2007; 6(18):2284-2292.

85. Ianaro A, Tersigni M, Belardo G, et al. NEMO-binding domain peptide inhibits proliferation of human melanoma cells. *Cancer Lett*. Nov. 10, 2008.

86. Agou F, Courtois G, Chiaravalli J, et al. Inhibition of NF-kappa B activation by peptides targeting NF-kappa B essential modulator (nemo) oligomerization. *J Biol Chem*. Dec. 24, 2004; 279(52):54248-54257.

87. Carvalho G, Fabre C, Braun T, et al. Inhibition of NEMO, the regulatory subunit of the IKK complex, induces apoptosis in high-risk myelodysplastic syndrome and acute myeloid leukemia. *Oncogene*. Apr. 5, 2007; 26(16):2299-2307.

88. Yaron A, Gonen H, Alkalay I, et al. Inhibition of NF-kappa-B cellular function via specific targeting of the I-kappa-B-ubiquitin ligase. *Embo J*. Nov. 3, 1997; 16(21):6486-6494.

89. Takada Y, Singh S, Aggarwal B B. Identification of a p65 peptide that selectively inhibits NF-kappa B activation induced by various inflammatory stimuli and its role in down-regulation of NF-kappaB-mediated gene expression and up-regulation of apoptosis. *J Biol Chem*. Apr. 9, 2004; 279(15):15096-15104.

90. Torgerson T R, Colosia A D, Donahue J P, Lin Y Z, Hawiger J. Regulation of NF-kappa b, AP-1, NFAT, and STAT1 nuclear import in T lymphocytes by noninvasive delivery of peptide carrying the nuclear localization sequence of NF-kappa B p50. *J Immunol*. Dec. 1, 1998; 161(11):6084-6092.

91. Letoha T, Somlai C, Takaes T, et al. A nuclear import inhibitory peptide ameliorates the severity of cholecystokinin-induced acute pancreatitis. *World J Gastroenterol*. Feb. 21, 2005; 11(7):990-999.

92. Saika S, Miyamoto T, Yamanaka O, et al. Therapeutic effect of topical administration of SN50, an inhibitor of nuclear factor-kappaB, in treatment of corneal alkali burns in mice. *Am J Pathol*. May 2005; 166(5):1393-1403.

93. Gonzalez-Ramos R, Van Langendonckt A, Defrere S, et al. Agents blocking the nuclear factor-kappaB pathway are effective inhibitors of endometriosis in an in vivo experimental model. *Gynecol Obstet Invest*. 2008; 65(3):174-186.

94. Poulaki V, Mitsiades C S, Joussen A M, Lappas A, Kirchhof B, Mitsiades N. Constitutive nuclear factor-kappaB activity is crucial for human retinoblastoma cell viability. *Am J Pathol*. December 2002; 161(6):2229-2240.

95. Starenki D, Namba H, Saenko V, Ohtsuru A, Yamashita S. Inhibition of nuclear factor-kappaB cascade potentiates the effect of a combination treatment of anaplastic thyroid cancer cells. *J Clin Endocrinol Metab*. January 2004; 89(1):410-418.

96. Xu Y, Fang F, St Clair D K, Sompol P, Josson S, St Clair W H. SN52, a novel nuclear factor-kappaB inhibitor, blocks nuclear import of RelB:p52 dimer and sensitizes prostate cancer cells to ionizing radiation. *Mol Cancer Ther*. August 2008; 7(8):2367-2376.

97. Van Liu X, Robinson D, Veach R A, et al. Peptide-directed suppression of a pro-inflammatory cytokine response. *J Biol Chem*. Jun. 2, 2000; 275(22):16774-16778.

98. Lambeth J D, Krause K H, Clark R A. NOX enzymes as novel targets for drug development. *Seminars in immunopathology*. July 2008; 30(3):339-363.

99. Rey F E, Cifuentes M E, Kiarash A, Quinn M T, Pagano P J. Novel competitive inhibitor of NAD(P)H oxidase assembly attenuates vascular O(2)(-) and systolic blood pressure in mice. *Circulation research*. Aug. 31, 2001; 89(5):408-414.

100. Seymour L W, Duncan R, Strohalm J, Kopecek J. Effect of molecular weight (Mw) of N-(2-hydroxypropyl)methacrylamide copolymers on body distribution and rate of excretion after subcutaneous, intraperitoneal, and intravenous administration to rats. *J Biomed Mater Res*. November 1987; 21(11):1341-1358.

101. Pasqualini R, Ruoslahti E. Organ targeting in vivo using phage display peptide libraries. *Nature*. 1996; 380:364-6.

102. Federal Register, Vol. 73, No. 104, May 29, 2008; http://www.gpo.gov/fdsys/pkg/FR-2008-05-29/pdf/E8-11806.pdf 103. Postmarket Drug Safety, Information for Patients and Providers, http://www.fda.gov/Drugs/DrugSafety/PostmarketDrugSafetyInformationforPatientsandProviders/ucm111085.htm

What is claimed is:

1. A method of reducing the severity of eclampsia or preeclampsia in a pregnant subject in need thereof, comprising:
   administering to the pregnant subject an effective amount of a composition comprising an elastin-like polypeptide (ELP) coupled to a therapeutic agent, wherein the ELP includes an amino acid sequence having at least about 5 repeats of the amino acid sequence VPGXG (SEQ ID NO: 1), where X is any amino acid except proline.

2. The method of claim 1, wherein the ELP includes an amino acid sequence comprising about 5 repeats to about 160 repeats of the amino acid sequence VPGXG, and wherein X in the sequence VPGXG is any amino acid except proline.

3. The method of claim 2, wherein the X in the amino acid sequence VPGXG is Val, Ala, and Gly in a ratio of 1:4-8:3-7.

4. The method of claim 2, wherein the ELP comprises an amino acid sequence selected from the amino acid sequences of SEQ ID NOs: 2, 3, 4, 5, 6, 7, 8, 9, 10, 11, 12, and 13.

5. The method of claim 2, wherein the ELP comprises about 160 repeats of the amino acid sequence VPGXG, and wherein X is Val, Ala, and Gly in a 1:8:7 ratio or in a 1:4:3 ratio; or the ELP comprises about 160 repeats of the amino acid sequence VPGXG, and wherein X is Gly or Lys.

6. The method of claim 2, wherein the ELP comprises about 32 repeats of the amino acid sequence VPGXG, and wherein X is Val, Ala, and Gly in a 1:4:3 ratio or in a 1:8:7 ratio.

7. The method of claim 2, wherein the ELP comprises about 80 repeats of the amino acid sequence VPGXG, and wherein X is Val, Ala, or Gly in a 1:4:3 ratio or a 1:8:7 ratio; or the ELP comprises about 80 repeats of the amino acid sequence VPGXG, and wherein X is Gly or Lys.

8. The method of claim 2, wherein the ELP comprises about 40 repeats of the amino acid sequence VPGXG, and wherein X is Lys or Gly.

9. The method of claim 1, wherein the composition further comprises a cell-penetrating peptide coupled to the ELP, wherein the cell-penetrating peptide is selected from a group consisting of penetratin, Tat, SynB1, Bac, polyArg, Membrane Translocating Sequence, Transportan, or pVEC.

10. The method of claim 1, wherein the composition further comprises an organ targeting peptide coupled to the ELP.

11. The method of claim 10, wherein the organ targeting peptide is selected from a kidney targeting peptide, a placenta targeting peptide, and a brain targeting peptide.

12. The method of claim 1, wherein the therapeutic agent is VEGF.

13. The method of claim 12, wherein the VEGF is selected from the group consisting of $VEGF_{121}$, $VEGF_{165}$, $VEGF_{189}$, $VEGF_{206}$, VEGF-A, VEGF-B, VEGF-C, VEGF-D, VEGF-E, or PlGF.

14. The method of claim 1, wherein the therapeutic agent comprises an amino acid sequence selected from the amino acid sequences of SEQ ID NOs: 14, 15, and 16.

15. The method of claim 1, wherein the therapeutic agent is a peptide selected from an NF-κB inhibitory peptide and an NADPH oxidase inhibitory peptide.

16. The method of claim 1, wherein the therapeutic agent is a small molecule drug that causes adverse events during pregnancy.

17. The method of claim 16, wherein the small molecule drug is an anti-hypertensive agent.

18. A method of delivering a therapeutic agent to a pregnant subject in need thereof, comprising:
   administering to the pregnant subject a composition comprising an elastin-like polypeptide (ELP) coupled to the therapeutic agent,
   wherein the ELP includes an amino acid sequence having at least about 5 repeats of the amino acid sequence VPGXG (SEQ ID NO: 1), where X is any amino acid except proline, wherein the therapeutic agent is VEGF.

19. The method of claim 18, wherein the VEGF is selected from the group consisting of $VEGF_{121}$, $VEGF_{165}$, $VEGF_{189}$, $VEGF_{206}$, VEGF-A, VEGF-B, VEGF-C, VEGF-D, VEGF-E, or PlGF.

20. The method of claim 18, wherein the composition comprises the amino acid sequence of SEQ ID NO: 14.

* * * * *

SEQUENCE LISTING

<160> NUMBER OF SEQ ID NOS: 16

<210> SEQ ID NO 1
<211> LENGTH: 5
<212> TYPE: PRT
<213> ORGANISM: Artificial Sequence
<220> FEATURE:
<223> OTHER INFORMATION: X is equal to any amino acid except proline
<220> FEATURE:
<223> OTHER INFORMATION: synthetic ELP

<400> SEQUENCE: 1

Xaa Pro Gly Xaa Gly
1               5

<210> SEQ ID NO 2
<211> LENGTH: 160
<212> TYPE: PRT
<213> ORGANISM: Artificial Sequence
<220> FEATURE:
<223> OTHER INFORMATION: synthetic ELP

<400> SEQUENCE: 2

Val Gly Val Pro Gly Ala Gly Val Pro Gly Gly Val Pro Gly Ala
1               5                   10                  15

Gly Val Pro Gly Gly Val Pro Gly Ala Gly Val Pro Gly Gly Gly
                20                  25                  30

Val Pro Gly Ala Gly Val Pro Gly Gly Val Pro Gly Ala Gly Val
                35                  40                  45

Pro Gly Gly Gly Val Pro Gly Ala Gly Val Pro Gly Gly Val Pro
        50                  55                  60

Gly Ala Gly Val Pro Gly Gly Val Pro Gly Ala Gly Val Pro Gly
65                  70                  75                  80

Val Gly Val Pro Gly Ala Gly Val Pro Gly Gly Val Pro Gly Ala
                85                  90                  95

Gly Val Pro Gly Gly Val Pro Gly Ala Gly Val Pro Gly Gly Gly
                100                 105                 110

Val Pro Gly Ala Gly Val Pro Gly Gly Val Pro Gly Ala Gly Val
                115                 120                 125

Pro Gly Gly Gly Val Pro Gly Ala Gly Val Pro Gly Gly Val Pro
        130                 135                 140

Gly Ala Gly Val Pro Gly Gly Val Pro Gly Ala Gly Val Pro Gly
145                 150                 155                 160

<210> SEQ ID NO 3
<211> LENGTH: 400
<212> TYPE: PRT
<213> ORGANISM: Artificial Sequence
<220> FEATURE:
<223> OTHER INFORMATION: synthetic ELP

<400> SEQUENCE: 3

Val Gly Val Pro Gly Ala Gly Val Pro Gly Gly Val Pro Gly Ala
1               5                   10                  15

Gly Val Pro Gly Gly Val Pro Gly Ala Gly Val Pro Gly Gly Gly
                20                  25                  30

Val Pro Gly Ala Gly Val Pro Gly Gly Val Pro Gly Ala Gly Val
                35                  40                  45

Pro Gly Gly Gly Val Pro Gly Ala Gly Val Pro Gly Gly Val Pro
        50                  55                  60

Gly Ala Gly Val Pro Gly Gly Val Pro Gly Ala Gly Val Pro Gly
65                  70                  75                  80

Val Gly Val Pro Gly Ala Gly Val Pro Gly Gly Val Pro Gly Ala
                85                  90                  95

Gly Val Pro Gly Gly Val Pro Gly Ala Gly Val Pro Gly Gly Gly
            100                 105                 110

Val Pro Gly Ala Gly Val Pro Gly Gly Val Pro Gly Ala Gly Val
        115                 120                 125

Pro Gly Gly Gly Val Pro Gly Ala Gly Val Pro Gly Gly Val Pro
    130                 135                 140

Gly Ala Gly Val Pro Gly Gly Val Pro Gly Ala Gly Val Pro Gly
145                 150                 155                 160

Val Gly Val Pro Gly Ala Gly Val Pro Gly Gly Val Pro Gly Ala
                165                 170                 175

Gly Val Pro Gly Gly Val Pro Gly Ala Gly Val Pro Gly Gly Gly
            180                 185                 190

Val Pro Gly Ala Gly Val Pro Gly Gly Val Pro Gly Ala Gly Val
        195                 200                 205

Pro Gly Gly Gly Val Pro Gly Ala Gly Val Pro Gly Gly Val Pro
    210                 215                 220

Gly Ala Gly Val Pro Gly Gly Val Pro Gly Ala Gly Val Pro Gly
225                 230                 235                 240

Val Gly Val Pro Gly Ala Gly Val Pro Gly Gly Val Pro Gly Ala
                245                 250                 255

Gly Val Pro Gly Gly Val Pro Gly Ala Gly Val Pro Gly Gly Gly
            260                 265                 270

Val Pro Gly Ala Gly Val Pro Gly Gly Val Pro Gly Ala Gly Val
        275                 280                 285

Pro Gly Gly Gly Val Pro Gly Ala Gly Val Pro Gly Gly Val Pro
    290                 295                 300

Gly Ala Gly Val Pro Gly Gly Val Pro Gly Ala Gly Val Pro Gly
305                 310                 315                 320

Val Gly Val Pro Gly Ala Gly Val Pro Gly Gly Val Pro Gly Ala
                325                 330                 335

Gly Val Pro Gly Gly Val Pro Gly Ala Gly Val Pro Gly Gly Gly
            340                 345                 350

Val Pro Gly Ala Gly Val Pro Gly Gly Val Pro Gly Ala Gly Val
        355                 360                 365

Pro Gly Gly Gly Val Pro Gly Ala Gly Val Pro Gly Gly Val Pro
    370                 375                 380

Gly Ala Gly Val Pro Gly Gly Val Pro Gly Ala Gly Val Pro Gly
385                 390                 395                 400

<210> SEQ ID NO 4
<211> LENGTH: 800
<212> TYPE: PRT
<213> ORGANISM: Artificial Sequence
<220> FEATURE:
<223> OTHER INFORMATION: synthetic ELP

<400> SEQUENCE: 4

Val Gly Val Pro Gly Ala Gly Val Pro Gly Gly Gly Val Pro Gly Ala
1               5                   10                  15

Gly Val Pro Gly Gly Gly Val Pro Gly Ala Gly Val Pro Gly Gly Gly
            20                  25                  30

-continued

Val Pro Gly Ala Gly Val Pro Gly Gly Val Pro Gly Ala Gly Val
            35                  40                  45
Pro Gly Gly Gly Val Pro Gly Ala Gly Val Pro Gly Gly Gly Val Pro
    50                  55                  60
Gly Ala Gly Val Pro Gly Gly Val Pro Gly Ala Gly Val Pro Gly
65                  70                  75                  80
Val Gly Val Pro Gly Ala Gly Val Pro Gly Gly Val Pro Gly Ala
                85                  90                  95
Gly Val Pro Gly Gly Gly Val Pro Gly Ala Gly Val Pro Gly Gly Gly
            100                 105                 110
Val Pro Gly Ala Gly Val Pro Gly Gly Val Pro Gly Ala Gly Val
            115                 120                 125
Pro Gly Gly Gly Val Pro Gly Ala Gly Val Pro Gly Gly Gly Val Pro
    130                 135                 140
Gly Ala Gly Val Pro Gly Gly Val Pro Gly Ala Gly Val Pro Gly
145                 150                 155                 160
Val Gly Val Pro Gly Ala Gly Val Pro Gly Gly Val Pro Gly Ala
                165                 170                 175
Gly Val Pro Gly Gly Gly Val Pro Gly Ala Gly Val Pro Gly Gly Gly
            180                 185                 190
Val Pro Gly Ala Gly Val Pro Gly Gly Val Pro Gly Ala Gly Val
            195                 200                 205
Pro Gly Gly Gly Val Pro Gly Ala Gly Val Pro Gly Gly Gly Val Pro
    210                 215                 220
Gly Ala Gly Val Pro Gly Gly Val Pro Gly Ala Gly Val Pro Gly
225                 230                 235                 240
Val Gly Val Pro Gly Ala Gly Val Pro Gly Gly Val Pro Gly Ala
                245                 250                 255
Gly Val Pro Gly Gly Gly Val Pro Gly Ala Gly Val Pro Gly Gly Gly
            260                 265                 270
Val Pro Gly Ala Gly Val Pro Gly Gly Val Pro Gly Ala Gly Val
            275                 280                 285
Pro Gly Gly Gly Val Pro Gly Ala Gly Val Pro Gly Gly Gly Val Pro
    290                 295                 300
Gly Ala Gly Val Pro Gly Gly Val Pro Gly Ala Gly Val Pro Gly
305                 310                 315                 320
Val Gly Val Pro Gly Ala Gly Val Pro Gly Gly Val Pro Gly Ala
                325                 330                 335
Gly Val Pro Gly Gly Gly Val Pro Gly Ala Gly Val Pro Gly Gly Gly
            340                 345                 350
Val Pro Gly Ala Gly Val Pro Gly Gly Val Pro Gly Ala Gly Val
            355                 360                 365
Pro Gly Gly Gly Val Pro Gly Ala Gly Val Pro Gly Gly Gly Val Pro
    370                 375                 380
Gly Ala Gly Val Pro Gly Gly Val Pro Gly Ala Gly Val Pro Gly
385                 390                 395                 400
Val Gly Val Pro Gly Ala Gly Val Pro Gly Gly Val Pro Gly Ala
                405                 410                 415
Gly Val Pro Gly Gly Gly Val Pro Gly Ala Gly Val Pro Gly Gly Gly
            420                 425                 430
Val Pro Gly Ala Gly Val Pro Gly Gly Val Pro Gly Ala Gly Val
            435                 440                 445
Pro Gly Gly Gly Val Pro Gly Ala Gly Val Pro Gly Gly Gly Val Pro

```
                450                 455                 460
Gly Ala Gly Val Pro Gly Gly Val Pro Gly Ala Gly Val Pro Gly
465                 470                 475                 480

Val Gly Val Pro Gly Ala Gly Val Pro Gly Gly Val Pro Gly Ala
                485                 490                 495

Gly Val Pro Gly Gly Val Pro Gly Ala Gly Val Pro Gly Gly Gly
            500                 505                 510

Val Pro Gly Ala Gly Val Pro Gly Gly Val Pro Gly Ala Gly Val
            515                 520                 525

Pro Gly Gly Gly Val Pro Gly Ala Gly Val Pro Gly Gly Val Pro
        530                 535                 540

Gly Ala Gly Val Pro Gly Gly Val Pro Gly Ala Gly Val Pro Gly
545                 550                 555                 560

Val Gly Val Pro Gly Ala Gly Val Pro Gly Gly Val Pro Gly Ala
                565                 570                 575

Gly Val Pro Gly Gly Val Pro Gly Ala Gly Val Pro Gly Gly Gly
            580                 585                 590

Val Pro Gly Ala Gly Val Pro Gly Gly Val Pro Gly Ala Gly Val
            595                 600                 605

Pro Gly Gly Gly Val Pro Gly Ala Gly Val Pro Gly Gly Val Pro
        610                 615                 620

Gly Ala Gly Val Pro Gly Gly Val Pro Gly Ala Gly Val Pro Gly
625                 630                 635                 640

Gly Gly Val Pro Gly Ala Gly Val Pro Gly Gly Val Pro Gly Ala
                645                 650                 655

Gly Val Pro Gly Gly Val Pro Gly Ala Gly Val Pro Gly Gly Gly
            660                 665                 670

Val Pro Gly Ala Gly Val Pro Gly Gly Val Pro Gly Ala Gly Val
            675                 680                 685

Pro Gly Gly Gly Val Pro Gly Ala Gly Val Pro Gly Gly Gly Val Pro
        690                 695                 700

Gly Ala Gly Val Pro Gly Gly Val Pro Gly Ala Gly Val Pro Gly
705                 710                 715                 720

Val Gly Val Pro Gly Ala Gly Val Pro Gly Gly Val Pro Gly Ala
                725                 730                 735

Gly Val Pro Gly Gly Val Pro Gly Ala Gly Val Pro Gly Gly Gly
            740                 745                 750

Val Pro Gly Ala Gly Val Pro Gly Gly Val Pro Gly Ala Gly Val
            755                 760                 765

Pro Gly Gly Gly Val Pro Gly Ala Gly Val Pro Gly Gly Val Pro
        770                 775                 780

Gly Ala Gly Val Pro Gly Gly Val Pro Gly Ala Gly Val Pro Gly
785                 790                 795                 800

<210> SEQ ID NO 5
<211> LENGTH: 200
<212> TYPE: PRT
<213> ORGANISM: Artificial Sequence
<220> FEATURE:
<223> OTHER INFORMATION: synthetic ELP

<400> SEQUENCE: 5

Gly Gly Val Pro Gly Gly Gly Val Pro Gly Gly Gly Val Pro Gly Gly
1               5                   10                  15

Gly Val Pro Gly Gly Gly Val Pro Gly Gly Gly Val Pro Gly Gly Gly
```

```
                20                  25                  30

Val Pro Gly Gly Gly Val Pro Gly Gly Gly Val Pro Gly Gly Gly Val
            35                  40                  45

Pro Gly Gly Gly Val Pro Gly Gly Gly Val Pro Gly Gly Gly Val Pro
        50                  55                  60

Gly Gly Gly Val Pro Gly Gly Gly Val Pro Gly Gly Gly Val Pro Gly
65                  70                  75                  80

Gly Gly Val Pro Gly Gly Gly Val Pro Gly Gly Gly Val Pro Gly Gly
            85                  90                  95

Gly Val Pro Gly Gly Gly Val Pro Gly Gly Gly Val Pro Gly Gly Gly
            100                 105                 110

Val Pro Gly Gly Gly Val Pro Gly Gly Gly Val Pro Gly Gly Gly Val
            115                 120                 125

Pro Gly Gly Gly Val Pro Gly Gly Gly Val Pro Gly Gly Gly Val Pro
        130                 135                 140

Gly Gly Gly Val Pro Gly Gly Gly Val Pro Gly Gly Gly Val Pro Gly
145                 150                 155                 160

Gly Gly Val Pro Gly Gly Gly Val Pro Gly Gly Gly Val Pro Gly Gly
            165                 170                 175

Gly Val Pro Gly Gly Gly Val Pro Gly Gly Gly Val Pro Gly Gly Gly
            180                 185                 190

Val Pro Gly Gly Gly Val Pro Gly
            195                 200

<210> SEQ ID NO 6
<211> LENGTH: 400
<212> TYPE: PRT
<213> ORGANISM: Artificial Sequence
<220> FEATURE:
<223> OTHER INFORMATION: synthetic ELP

<400> SEQUENCE: 6

Gly Gly Val Pro Gly Gly Gly Val Pro Gly Gly Gly Val Pro Gly Gly
1               5                   10                  15

Gly Val Pro Gly Gly Gly Val Pro Gly Gly Gly Val Pro Gly Gly Gly
            20                  25                  30

Val Pro Gly Gly Gly Val Pro Gly Gly Gly Val Pro Gly Gly Gly Val
            35                  40                  45

Pro Gly Gly Gly Val Pro Gly Gly Gly Val Pro Gly Gly Gly Val Pro
        50                  55                  60

Gly Gly Gly Val Pro Gly Gly Gly Val Pro Gly Gly Gly Val Pro Gly
65                  70                  75                  80

Gly Gly Val Pro Gly Gly Gly Val Pro Gly Gly Gly Val Pro Gly Gly
            85                  90                  95

Gly Val Pro Gly Gly Gly Val Pro Gly Gly Gly Val Pro Gly Gly Gly
            100                 105                 110

Val Pro Gly Gly Gly Val Pro Gly Gly Gly Val Pro Gly Gly Gly Val
            115                 120                 125

Pro Gly Gly Gly Val Pro Gly Gly Gly Val Pro Gly Gly Gly Val Pro
        130                 135                 140

Gly Gly Gly Val Pro Gly Gly Gly Val Pro Gly Gly Gly Val Pro Gly
145                 150                 155                 160

Gly Gly Val Pro Gly Gly Gly Val Pro Gly Gly Gly Val Pro Gly Gly
            165                 170                 175

Gly Val Pro Gly Gly Gly Val Pro Gly Gly Gly Val Pro Gly Gly Gly
```

```
                180                 185                 190
Val Pro Gly Gly Val Pro Gly Gly Val Pro Gly Gly Val
            195                 200                 205

Pro Gly Gly Gly Val Pro Gly Gly Gly Val Pro Gly Gly Gly Val Pro
            210                 215                 220

Gly Gly Gly Val Pro Gly Gly Gly Val Pro Gly Gly Gly Val Pro Gly
225                 230                 235                 240

Gly Gly Val Pro Gly Gly Gly Val Pro Gly Gly Gly Val Pro Gly Gly
                245                 250                 255

Gly Val Pro Gly Gly Gly Val Pro Gly Gly Gly Val Pro Gly Gly Gly
            260                 265                 270

Val Pro Gly Gly Gly Val Pro Gly Gly Gly Val Pro Gly Gly Gly Val
            275                 280                 285

Pro Gly Gly Gly Val Pro Gly Gly Gly Val Pro Gly Gly Gly Val Pro
            290                 295                 300

Gly Gly Gly Val Pro Gly Gly Gly Val Pro Gly Gly Gly Val Pro Gly
305                 310                 315                 320

Gly Gly Val Pro Gly Gly Gly Val Pro Gly Gly Gly Val Pro Gly Gly
                325                 330                 335

Gly Val Pro Gly Gly Gly Val Pro Gly Gly Gly Val Pro Gly Gly Gly
            340                 345                 350

Val Pro Gly Gly Gly Val Pro Gly Gly Gly Val Pro Gly Gly Gly Val
            355                 360                 365

Pro Gly Gly Gly Val Pro Gly Gly Gly Val Pro Gly Gly Gly Val Pro
            370                 375                 380

Gly Gly Gly Val Pro Gly Gly Gly Val Pro Gly Gly Gly Val Pro Gly
385                 390                 395                 400

<210> SEQ ID NO 7
<211> LENGTH: 800
<212> TYPE: PRT
<213> ORGANISM: Artificial Sequence
<220> FEATURE:
<223> OTHER INFORMATION: synthetic ELP

<400> SEQUENCE: 7

Gly Gly Val Pro Gly Gly Val Pro Gly Gly Gly Val Pro Gly Gly
1               5                   10                  15

Gly Val Pro Gly Gly Gly Val Pro Gly Gly Gly Val Pro Gly Gly Gly
                20                  25                  30

Val Pro Gly Gly Gly Val Pro Gly Gly Gly Val Pro Gly Gly Gly Val
            35                  40                  45

Pro Gly Gly Gly Val Pro Gly Gly Gly Val Pro Gly Gly Gly Val Pro
            50                  55                  60

Gly Gly Gly Val Pro Gly Gly Gly Val Pro Gly Gly Gly Val Pro Gly
65                  70                  75                  80

Gly Gly Val Pro Gly Gly Gly Val Pro Gly Gly Gly Val Pro Gly Gly
                85                  90                  95

Gly Val Pro Gly Gly Gly Val Pro Gly Gly Gly Val Pro Gly Gly Gly
            100                 105                 110

Val Pro Gly Gly Gly Val Pro Gly Gly Gly Val Pro Gly Gly Gly Val
            115                 120                 125

Pro Gly Gly Gly Val Pro Gly Gly Gly Val Pro Gly Gly Gly Val Pro
            130                 135                 140

Gly Gly Gly Val Pro Gly Gly Gly Val Pro Gly Gly Gly Val Pro Gly
```

-continued

```
            145                 150                 155                 160
Gly Gly Val Pro Gly Gly Val Pro Gly Gly Val Pro Gly Gly
                165                 170                 175
Gly Val Pro Gly Gly Val Pro Gly Gly Val Pro Gly Gly
            180                 185                 190
Val Pro Gly Gly Val Pro Gly Gly Val Pro Gly Gly Val
        195                 200                 205
Pro Gly Gly Gly Val Pro Gly Gly Val Pro Gly Gly Val Pro
    210                 215                 220
Gly Gly Gly Val Pro Gly Gly Val Pro Gly Gly Val Pro Gly
225                 230                 235                 240
Gly Gly Val Pro Gly Gly Val Pro Gly Gly Val Pro Gly Gly
                245                 250                 255
Gly Val Pro Gly Gly Val Pro Gly Gly Val Pro Gly Gly Gly
            260                 265                 270
Val Pro Gly Gly Val Pro Gly Gly Val Pro Gly Gly Gly Val
        275                 280                 285
Pro Gly Gly Gly Val Pro Gly Gly Val Pro Gly Gly Val Pro
    290                 295                 300
Gly Gly Gly Val Pro Gly Gly Val Pro Gly Gly Val Pro Gly
305                 310                 315                 320
Gly Gly Val Pro Gly Gly Gly Val Pro Gly Gly Val Pro Gly Gly
                325                 330                 335
Gly Val Pro Gly Gly Gly Val Pro Gly Gly Val Pro Gly Gly Gly
            340                 345                 350
Val Pro Gly Gly Gly Val Pro Gly Gly Val Pro Gly Gly Gly Val
        355                 360                 365
Pro Gly Gly Gly Val Pro Gly Gly Val Pro Gly Gly Val Pro
    370                 375                 380
Gly Gly Gly Val Pro Gly Gly Val Pro Gly Gly Val Pro Gly
385                 390                 395                 400
Gly Gly Val Pro Gly Gly Gly Val Pro Gly Gly Val Pro Gly Gly
                405                 410                 415
Gly Val Pro Gly Gly Gly Val Pro Gly Gly Val Pro Gly Gly Gly
            420                 425                 430
Val Pro Gly Gly Gly Val Pro Gly Gly Val Pro Gly Gly Gly Val
        435                 440                 445
Pro Gly Gly Gly Val Pro Gly Gly Val Pro Gly Gly Val Pro
    450                 455                 460
Gly Gly Gly Val Pro Gly Gly Val Pro Gly Gly Val Pro Gly
465                 470                 475                 480
Gly Gly Val Pro Gly Gly Gly Val Pro Gly Gly Val Pro Gly Gly
                485                 490                 495
Gly Val Pro Gly Gly Gly Val Pro Gly Gly Val Pro Gly Gly Gly
            500                 505                 510
Val Pro Gly Gly Gly Val Pro Gly Gly Val Pro Gly Gly Gly Val
        515                 520                 525
Pro Gly Gly Gly Val Pro Gly Gly Val Pro Gly Gly Val Pro
    530                 535                 540
Gly Gly Gly Val Pro Gly Gly Val Pro Gly Gly Val Pro Gly
545                 550                 555                 560
Gly Gly Val Pro Gly Gly Gly Val Pro Gly Gly Val Pro Gly Gly
                565                 570                 575
```

-continued

```
Gly Val Pro Gly Gly Val Pro Gly Gly Val Pro Gly Gly
            580             585             590

Val Pro Gly Gly Val Pro Gly Gly Val Pro Gly Gly Val
        595             600             605

Pro Gly Gly Gly Val Pro Gly Gly Gly Val Pro Gly Gly Gly Val Pro
    610             615             620

Gly Gly Gly Val Pro Gly Gly Gly Val Pro Gly Gly Gly Val Pro Gly
625             630             635             640

Gly Gly Val Pro Gly Gly Gly Val Pro Gly Gly Val Pro Gly Gly
            645             650             655

Gly Val Pro Gly Gly Gly Val Pro Gly Gly Val Pro Gly Gly Gly
            660             665             670

Val Pro Gly Gly Val Pro Gly Gly Gly Val Pro Gly Gly Gly Val
        675             680             685

Pro Gly Gly Gly Val Pro Gly Gly Gly Val Pro Gly Gly Gly Val Pro
    690             695             700

Gly Gly Gly Val Pro Gly Gly Gly Val Pro Gly Gly Val Pro Gly
705             710             715             720

Gly Gly Val Pro Gly Gly Gly Val Pro Gly Gly Val Pro Gly Gly
            725             730             735

Gly Val Pro Gly Gly Gly Val Pro Gly Gly Val Pro Gly Gly Gly
            740             745             750

Val Pro Gly Gly Gly Val Pro Gly Gly Gly Val Pro Gly Gly Gly Val
        755             760             765

Pro Gly Gly Val Pro Gly Gly Gly Val Pro Gly Gly Gly Val Pro
    770             775             780

Gly Gly Gly Val Pro Gly Gly Gly Val Pro Gly Gly Gly Val Pro Gly
785             790             795             800
```

<210> SEQ ID NO 8
<211> LENGTH: 160
<212> TYPE: PRT
<213> ORGANISM: Artificial Sequence
<220> FEATURE:
<223> OTHER INFORMATION: synthetic ELP

<400> SEQUENCE: 8

```
Val Gly Val Pro Gly Ala Gly Val Pro Gly Gly Val Pro Gly Ala
1               5               10              15

Gly Val Pro Gly Gly Val Pro Gly Ala Gly Val Pro Gly Gly Gly
            20              25              30

Val Pro Gly Ala Gly Val Pro Gly Val Gly Pro Gly Ala Gly Val
        35              40              45

Pro Gly Gly Gly Val Pro Gly Ala Gly Val Pro Gly Gly Val Pro
    50              55              60

Gly Ala Gly Val Pro Gly Gly Val Pro Gly Ala Gly Val Pro Gly
65              70              75              80

Val Gly Val Pro Gly Ala Gly Val Pro Gly Gly Val Pro Gly Ala
            85              90              95

Gly Val Pro Gly Gly Val Pro Gly Ala Gly Val Pro Gly Gly Gly
            100             105             110

Val Pro Gly Ala Gly Val Pro Gly Val Gly Pro Gly Ala Gly Val
        115             120             125

Pro Gly Gly Gly Val Pro Gly Ala Gly Val Pro Gly Gly Val Pro
    130             135             140
```

```
Gly Ala Gly Val Pro Gly Gly Val Pro Gly Ala Gly Val Pro Gly
145                 150                 155                 160
```

<210> SEQ ID NO 9
<211> LENGTH: 400
<212> TYPE: PRT
<213> ORGANISM: Artificial Sequence
<220> FEATURE:
<223> OTHER INFORMATION: synthetic ELP

<400> SEQUENCE: 9

```
Val Gly Val Pro Gly Ala Gly Val Pro Gly Gly Gly Val Pro Gly Ala
1               5                   10                  15
Gly Val Pro Gly Gly Val Pro Gly Ala Gly Val Pro Gly Gly Gly
            20                  25                  30
Val Pro Gly Ala Gly Val Pro Gly Val Gly Val Pro Gly Ala Gly Val
            35                  40                  45
Pro Gly Gly Gly Val Pro Gly Ala Gly Val Pro Gly Gly Gly Val Pro
    50                  55                  60
Gly Ala Gly Val Pro Gly Gly Val Pro Gly Ala Gly Val Pro Gly
65                  70                  75                  80
Val Gly Val Pro Gly Ala Gly Val Pro Gly Gly Val Pro Gly Ala
                85                  90                  95
Gly Val Pro Gly Gly Val Pro Gly Ala Gly Val Pro Gly Gly Gly
            100                 105                 110
Val Pro Gly Ala Gly Val Pro Gly Val Gly Val Pro Gly Ala Gly Val
            115                 120                 125
Pro Gly Gly Gly Val Pro Gly Ala Gly Val Pro Gly Gly Gly Val Pro
    130                 135                 140
Gly Ala Gly Val Pro Gly Gly Val Pro Gly Ala Gly Val Pro Gly
145                 150                 155                 160
Val Gly Val Pro Gly Ala Gly Val Pro Gly Gly Gly Val Pro Gly Ala
                165                 170                 175
Gly Val Pro Gly Gly Val Pro Gly Ala Gly Val Pro Gly Gly Gly
            180                 185                 190
Val Pro Gly Ala Gly Val Pro Gly Val Gly Val Pro Gly Ala Gly Val
            195                 200                 205
Pro Gly Gly Gly Val Pro Gly Ala Gly Val Pro Gly Gly Gly Val Pro
    210                 215                 220
Gly Ala Gly Val Pro Gly Gly Val Pro Gly Ala Gly Val Pro Gly
225                 230                 235                 240
Val Gly Val Pro Gly Ala Gly Val Pro Gly Gly Gly Val Pro Gly Ala
                245                 250                 255
Gly Val Pro Gly Gly Val Pro Gly Ala Gly Val Pro Gly Gly Gly
            260                 265                 270
Val Pro Gly Ala Gly Val Pro Gly Val Gly Val Pro Gly Ala Gly Val
            275                 280                 285
Pro Gly Gly Gly Val Pro Gly Ala Gly Val Pro Gly Gly Gly Val Pro
    290                 295                 300
Gly Ala Gly Val Pro Gly Gly Val Pro Gly Ala Gly Val Pro Gly
305                 310                 315                 320
Val Gly Val Pro Gly Ala Gly Val Pro Gly Gly Gly Val Pro Gly Ala
                325                 330                 335
Gly Val Pro Gly Gly Val Pro Gly Ala Gly Val Pro Gly Gly Gly
            340                 345                 350
```

```
Val Pro Gly Ala Gly Val Pro Gly Val Gly Val Pro Gly Ala Gly Val
        355                 360                 365

Pro Gly Gly Gly Val Pro Gly Ala Gly Val Pro Gly Gly Gly Val Pro
    370                 375                 380

Gly Ala Gly Val Pro Gly Gly Val Pro Gly Ala Gly Val Pro Gly
385                 390                 395                 400

<210> SEQ ID NO 10
<211> LENGTH: 800
<212> TYPE: PRT
<213> ORGANISM: Artificial Sequence
<220> FEATURE:
<223> OTHER INFORMATION: synthetic ELP

<400> SEQUENCE: 10

Val Gly Val Pro Gly Ala Gly Val Pro Gly Gly Val Pro Gly Ala
1               5                   10                  15

Gly Val Pro Gly Gly Val Pro Gly Ala Gly Val Pro Gly Gly Gly
            20                  25                  30

Val Pro Gly Ala Gly Val Pro Gly Val Gly Val Pro Gly Ala Gly Val
        35                  40                  45

Pro Gly Gly Gly Val Pro Gly Ala Gly Val Pro Gly Gly Gly Val Pro
    50                  55                  60

Gly Ala Gly Val Pro Gly Gly Val Pro Gly Ala Gly Val Pro Gly
65                  70                  75                  80

Val Gly Val Pro Gly Ala Gly Val Pro Gly Gly Gly Val Pro Gly Ala
                85                  90                  95

Gly Val Pro Gly Gly Val Pro Gly Ala Gly Val Pro Gly Gly Gly
            100                 105                 110

Val Pro Gly Ala Gly Val Pro Gly Val Gly Val Pro Gly Ala Gly Val
        115                 120                 125

Pro Gly Gly Gly Val Pro Gly Ala Gly Val Pro Gly Gly Gly Val Pro
    130                 135                 140

Gly Ala Gly Val Pro Gly Gly Val Pro Gly Ala Gly Val Pro Gly
145                 150                 155                 160

Val Gly Val Pro Gly Ala Gly Val Pro Gly Gly Gly Val Pro Gly Ala
                165                 170                 175

Gly Val Pro Gly Gly Gly Val Pro Gly Ala Gly Val Pro Gly Gly Gly
            180                 185                 190

Val Pro Gly Ala Gly Val Pro Gly Val Gly Val Pro Gly Ala Gly Val
        195                 200                 205

Pro Gly Gly Gly Val Pro Gly Ala Gly Val Pro Gly Gly Gly Val Pro
    210                 215                 220

Gly Ala Gly Val Pro Gly Gly Gly Val Pro Gly Ala Gly Val Pro Gly
225                 230                 235                 240

Val Gly Val Pro Gly Ala Gly Val Pro Gly Gly Gly Val Pro Gly Ala
                245                 250                 255

Gly Val Pro Gly Gly Val Pro Gly Ala Gly Val Pro Gly Gly Gly
            260                 265                 270

Val Pro Gly Ala Gly Val Pro Gly Val Gly Val Pro Gly Ala Gly Val
        275                 280                 285

Pro Gly Gly Gly Val Pro Gly Ala Gly Val Pro Gly Gly Gly Val Pro
    290                 295                 300

Gly Ala Gly Val Pro Gly Gly Gly Val Pro Gly Ala Gly Val Pro Gly
305                 310                 315                 320
```

```
Val Gly Val Pro Gly Ala Gly Val Pro Gly Gly Val Pro Gly Ala
            325                 330                 335

Gly Val Pro Gly Gly Val Pro Gly Ala Gly Val Pro Gly Gly Gly
            340                 345                 350

Val Pro Gly Ala Gly Val Pro Gly Val Gly Val Pro Gly Ala Gly Val
            355                 360                 365

Pro Gly Gly Gly Val Pro Gly Ala Gly Val Pro Gly Gly Val Pro
            370                 375                 380

Gly Ala Gly Val Pro Gly Gly Val Pro Gly Ala Gly Val Pro Gly
385                 390                 395                 400

Val Gly Val Pro Gly Ala Gly Val Pro Gly Gly Val Pro Gly Ala
            405                 410                 415

Gly Val Pro Gly Gly Val Pro Gly Ala Gly Val Pro Gly Gly Gly
            420                 425                 430

Val Pro Gly Ala Gly Val Pro Gly Val Gly Val Pro Gly Ala Gly Val
            435                 440                 445

Pro Gly Gly Gly Val Pro Gly Ala Gly Val Pro Gly Gly Val Pro
            450                 455                 460

Gly Ala Gly Val Pro Gly Gly Val Pro Gly Ala Gly Val Pro Gly
465                 470                 475                 480

Val Gly Val Pro Gly Ala Gly Val Pro Gly Gly Val Pro Gly Ala
            485                 490                 495

Gly Val Pro Gly Gly Val Pro Gly Ala Gly Val Pro Gly Gly Gly
            500                 505                 510

Val Pro Gly Ala Gly Val Pro Gly Val Gly Val Pro Gly Ala Gly Val
            515                 520                 525

Pro Gly Gly Gly Val Pro Gly Ala Gly Val Pro Gly Gly Val Pro
            530                 535                 540

Gly Ala Gly Val Pro Gly Gly Val Pro Gly Ala Gly Val Pro Gly
545                 550                 555                 560

Val Gly Val Pro Gly Ala Gly Val Pro Gly Gly Val Pro Gly Ala
            565                 570                 575

Gly Val Pro Gly Gly Val Pro Gly Ala Gly Val Pro Gly Gly Gly
            580                 585                 590

Val Pro Gly Ala Gly Val Pro Gly Val Gly Val Pro Gly Ala Gly Val
            595                 600                 605

Pro Gly Gly Gly Val Pro Gly Ala Gly Val Pro Gly Gly Val Pro
            610                 615                 620

Gly Ala Gly Val Pro Gly Gly Val Pro Gly Ala Gly Val Pro Gly
625                 630                 635                 640

Val Gly Val Pro Gly Ala Gly Val Pro Gly Gly Val Pro Gly Ala
            645                 650                 655

Gly Val Pro Gly Gly Val Pro Gly Ala Gly Val Pro Gly Gly Gly
            660                 665                 670

Val Pro Gly Ala Gly Val Pro Gly Val Gly Val Pro Gly Ala Gly Val
            675                 680                 685

Pro Gly Gly Gly Val Pro Gly Ala Gly Val Pro Gly Gly Val Pro
            690                 695                 700

Gly Ala Gly Val Pro Gly Gly Val Pro Gly Ala Gly Val Pro Gly
705                 710                 715                 720

Val Gly Val Pro Gly Ala Gly Val Pro Gly Gly Val Pro Gly Ala
            725                 730                 735
```

Gly Val Pro Gly Gly Val Pro Gly Ala Gly Val Pro Gly Gly Gly
            740                 745                 750

Val Pro Gly Ala Gly Val Pro Gly Val Gly Val Pro Gly Ala Gly Val
            755                 760                 765

Pro Gly Gly Gly Val Pro Gly Ala Gly Val Pro Gly Gly Gly Val Pro
            770                 775                 780

Gly Ala Gly Val Pro Gly Gly Val Pro Gly Ala Gly Val Pro Gly
785                 790                 795                 800

<210> SEQ ID NO 11
<211> LENGTH: 200
<212> TYPE: PRT
<213> ORGANISM: Artificial Sequence
<220> FEATURE:
<223> OTHER INFORMATION: synthetic ELP

<400> SEQUENCE: 11

Lys Gly Val Pro Gly Lys Gly Val Pro Gly Lys Gly Val Pro Gly Lys
1               5                   10                  15

Gly Val Pro Gly Lys Gly Val Pro Gly Lys Gly Val Pro Gly Lys Gly
            20                  25                  30

Val Pro Gly Lys Gly Val Pro Gly Lys Gly Val Pro Gly Lys Gly Val
            35                  40                  45

Pro Gly Lys Gly Val Pro Gly Lys Gly Val Pro Gly Lys Gly Val Pro
    50                  55                  60

Gly Lys Gly Val Pro Gly Lys Gly Val Pro Gly Lys Gly Val Pro Gly
65                  70                  75                  80

Lys Gly Val Pro Gly Lys Gly Val Pro Gly Lys Gly Val Pro Gly Lys
                85                  90                  95

Gly Val Pro Gly Lys Gly Val Pro Gly Lys Gly Val Pro Gly Lys Gly
            100                 105                 110

Val Pro Gly Lys Gly Val Pro Gly Lys Gly Val Pro Gly Lys Gly Val
            115                 120                 125

Pro Gly Lys Gly Val Pro Gly Lys Gly Val Pro Gly Lys Gly Val Pro
    130                 135                 140

Gly Lys Gly Val Pro Gly Lys Gly Val Pro Gly Lys Gly Val Pro Gly
145                 150                 155                 160

Lys Gly Val Pro Gly Lys Gly Val Pro Gly Lys Gly Val Pro Gly Lys
                165                 170                 175

Gly Val Pro Gly Lys Gly Val Pro Gly Lys Gly Val Pro Gly Lys Gly
            180                 185                 190

Val Pro Gly Lys Gly Val Pro Gly
            195                 200

<210> SEQ ID NO 12
<211> LENGTH: 400
<212> TYPE: PRT
<213> ORGANISM: Artificial Sequence
<220> FEATURE:
<223> OTHER INFORMATION: synthetic ELP

<400> SEQUENCE: 12

Lys Gly Val Pro Gly Lys Gly Val Pro Gly Lys Gly Val Pro Gly Lys
1               5                   10                  15

Gly Val Pro Gly Lys Gly Val Pro Gly Lys Gly Val Pro Gly Lys Gly
            20                  25                  30

Val Pro Gly Lys Gly Val Pro Gly Lys Gly Val Pro Gly Lys Gly Val
            35                  40                  45

Pro Gly Lys Gly Val Pro Gly Lys Gly Val Pro Gly Lys Gly Val Pro
    50                  55                  60

Gly Lys Gly Val Pro Gly Lys Gly Val Pro Gly Lys Gly Val Pro Gly
65                  70                  75                  80

Lys Gly Val Pro Gly Lys Gly Val Pro Gly Lys Gly Val Pro Gly Lys
                85                  90                  95

Gly Val Pro Gly Lys Gly Val Pro Gly Lys Gly Val Pro Gly Lys Gly
            100                 105                 110

Val Pro Gly Lys Gly Val Pro Gly Lys Gly Val Pro Gly Lys Gly Val
        115                 120                 125

Pro Gly Lys Gly Val Pro Gly Lys Gly Val Pro Gly Lys Gly Val Pro
    130                 135                 140

Gly Lys Gly Val Pro Gly Lys Gly Val Pro Gly Lys Gly Val Pro Gly
145                 150                 155                 160

Lys Gly Val Pro Gly Lys Gly Val Pro Gly Lys Gly Val Pro Gly Lys
                165                 170                 175

Gly Val Pro Gly Lys Gly Val Pro Gly Lys Gly Val Pro Gly Lys Gly
            180                 185                 190

Val Pro Gly Lys Gly Val Pro Gly Lys Gly Val Pro Gly Lys Gly Val
        195                 200                 205

Pro Gly Lys Gly Val Pro Gly Lys Gly Val Pro Gly Lys Gly Val Pro
    210                 215                 220

Gly Lys Gly Val Pro Gly Lys Gly Val Pro Gly Lys Gly Val Pro Gly
225                 230                 235                 240

Lys Gly Val Pro Gly Lys Gly Val Pro Gly Lys Gly Val Pro Gly Lys
                245                 250                 255

Gly Val Pro Gly Lys Gly Val Pro Gly Lys Gly Val Pro Gly Lys Gly
            260                 265                 270

Val Pro Gly Lys Gly Val Pro Gly Lys Gly Val Pro Gly Lys Gly Val
        275                 280                 285

Pro Gly Lys Gly Val Pro Gly Lys Gly Val Pro Gly Lys Gly Val Pro
    290                 295                 300

Gly Lys Gly Val Pro Gly Lys Gly Val Pro Gly Lys Gly Val Pro Gly
305                 310                 315                 320

Lys Gly Val Pro Gly Lys Gly Val Pro Gly Lys Gly Val Pro Gly Lys
                325                 330                 335

Gly Val Pro Gly Lys Gly Val Pro Gly Lys Gly Val Pro Gly Lys Gly
            340                 345                 350

Val Pro Gly Lys Gly Val Pro Gly Lys Gly Val Pro Gly Lys Gly Val
        355                 360                 365

Pro Gly Lys Gly Val Pro Gly Lys Gly Val Pro Gly Lys Gly Val Pro
    370                 375                 380

Gly Lys Gly Val Pro Gly Lys Gly Val Pro Gly Lys Gly Val Pro Gly
385                 390                 395                 400

<210> SEQ ID NO 13
<211> LENGTH: 800
<212> TYPE: PRT
<213> ORGANISM: Artificial Sequence
<220> FEATURE:
<223> OTHER INFORMATION: synthetic ELP

<400> SEQUENCE: 13

Lys Gly Val Pro Gly Lys Gly Val Pro Gly Lys Gly Val Pro Gly Lys
1               5                   10                  15

-continued

Gly Val Pro Gly Lys Gly Val Pro Gly Lys Gly Val Pro Gly Lys Gly
            20                  25                  30
Val Pro Gly Lys Gly Val Pro Gly Lys Gly Val Pro Gly Lys Gly Val
            35                  40                  45
Pro Gly Lys Gly Val Pro Gly Lys Gly Val Pro Gly Lys Gly Val Pro
            50                  55                  60
Gly Lys Gly Val Pro Gly Lys Gly Val Pro Gly Lys Gly Val Pro Gly
65                  70                  75                  80
Lys Gly Val Pro Gly Lys Gly Val Pro Gly Lys Gly Val Pro Gly Lys
                85                  90                  95
Gly Val Pro Gly Lys Gly Val Pro Gly Lys Gly Val Pro Gly Lys Gly
            100                 105                 110
Val Pro Gly Lys Gly Val Pro Gly Lys Gly Val Pro Gly Lys Gly Val
            115                 120                 125
Pro Gly Lys Gly Val Pro Gly Lys Gly Val Pro Gly Lys Gly Val Pro
            130                 135                 140
Gly Lys Gly Val Pro Gly Lys Gly Val Pro Gly Lys Gly Val Pro Gly
145                 150                 155                 160
Lys Gly Val Pro Gly Lys Gly Val Pro Gly Lys Gly Val Pro Gly Lys
                165                 170                 175
Gly Val Pro Gly Lys Gly Val Pro Gly Lys Gly Val Pro Gly Lys Gly
            180                 185                 190
Val Pro Gly Lys Gly Val Pro Gly Lys Gly Val Pro Gly Lys Gly Val
            195                 200                 205
Pro Gly Lys Gly Val Pro Gly Lys Gly Val Pro Gly Lys Gly Val Pro
            210                 215                 220
Gly Lys Gly Val Pro Gly Lys Gly Val Pro Gly Lys Gly Val Pro Gly
225                 230                 235                 240
Lys Gly Val Pro Gly Lys Gly Val Pro Gly Lys Gly Val Pro Gly Lys
                245                 250                 255
Gly Val Pro Gly Lys Gly Val Pro Gly Lys Gly Val Pro Gly Lys Gly
            260                 265                 270
Val Pro Gly Lys Gly Val Pro Gly Lys Gly Val Pro Gly Lys Gly Val
            275                 280                 285
Pro Gly Lys Gly Val Pro Gly Lys Gly Val Pro Gly Lys Gly Val Pro
            290                 295                 300
Gly Lys Gly Val Pro Gly Lys Gly Val Pro Gly Lys Gly Val Pro Gly
305                 310                 315                 320
Lys Gly Val Pro Gly Lys Gly Val Pro Gly Lys Gly Val Pro Gly Lys
                325                 330                 335
Gly Val Pro Gly Lys Gly Val Pro Gly Lys Gly Val Pro Gly Lys Gly
            340                 345                 350
Val Pro Gly Lys Gly Val Pro Gly Lys Gly Val Pro Gly Lys Gly Val
            355                 360                 365
Pro Gly Lys Gly Val Pro Gly Lys Gly Val Pro Gly Lys Gly Val Pro
            370                 375                 380
Gly Lys Gly Val Pro Gly Lys Gly Val Pro Gly Lys Gly Val Pro Gly
385                 390                 395                 400
Lys Gly Val Pro Gly Lys Gly Val Pro Gly Lys Gly Val Pro Gly Lys
                405                 410                 415
Gly Val Pro Gly Lys Gly Val Pro Gly Lys Gly Val Pro Gly Lys Gly
            420                 425                 430

Val Pro Gly Lys Gly Val Pro Gly Lys Gly Val
            435                 440                 445

Pro Gly Lys Gly Val Pro Gly Lys Gly Val P

```
Met Ser Lys Gly Pro Gly Val Gly Val Pro Gly Ala Gly Val Pro Gly
1               5                   10                  15
Gly Gly Val Pro Gly Ala Gly Val Pro Gly Gly Val Pro Gly Ala
            20                  25                  30
Gly Val Pro Gly Gly Val Pro Gly Ala Gly Val Pro Gly Gly Gly
            35                  40                  45
Val Pro Gly Ala Gly Val Pro Gly Gly Val Pro Gly Ala Gly Val
    50                  55                  60
Pro Gly Gly Gly Val Pro Gly Ala Gly Val Pro Gly Gly Val Pro
65              70                  75                  80
Gly Ala Gly Val Pro Gly Val Gly Val Pro Gly Ala Gly Val Pro Gly
                85                  90                  95
Gly Gly Val Pro Gly Ala Gly Val Pro Gly Gly Val Pro Gly Ala
            100                 105                 110
Gly Val Pro Gly Gly Val Pro Gly Ala Gly Val Pro Gly Gly Gly
            115                 120                 125
Val Pro Gly Ala Gly Val Pro Gly Gly Val Pro Gly Ala Gly Val
    130                 135                 140
Pro Gly Gly Gly Val Pro Gly Ala Gly Val Pro Gly Gly Val Pro
145             150                 155                 160
Gly Ala Gly Val Pro Gly Val Gly Val Pro Gly Ala Gly Val Pro Gly
                165                 170                 175
Gly Gly Val Pro Gly Ala Gly Val Pro Gly Gly Val Pro Gly Ala
            180                 185                 190
Gly Val Pro Gly Gly Val Pro Gly Ala Gly Val Pro Gly Gly Gly
            195                 200                 205
Val Pro Gly Ala Gly Val Pro Gly Gly Val Pro Gly Ala Gly Val
    210                 215                 220
Pro Gly Gly Gly Val Pro Gly Ala Gly Val Pro Gly Gly Val Pro
225             230                 235                 240
Gly Ala Gly Val Pro Gly Val Gly Val Pro Gly Ala Gly Val Pro Gly
                245                 250                 255
Gly Gly Val Pro Gly Ala Gly Val Pro Gly Gly Val Pro Gly Ala
            260                 265                 270
Gly Val Pro Gly Gly Val Pro Gly Ala Gly Val Pro Gly Gly Gly
            275                 280                 285
Val Pro Gly Ala Gly Val Pro Gly Gly Val Pro Gly Ala Gly Val
    290                 295                 300
Pro Gly Gly Gly Val Pro Gly Ala Gly Val Pro Gly Gly Val Pro
305             310                 315                 320
Gly Ala Gly Val Pro Gly Val Gly Val Pro Gly Ala Gly Val Pro Gly
                325                 330                 335
Gly Gly Val Pro Gly Ala Gly Val Pro Gly Gly Val Pro Gly Ala
            340                 345                 350
Gly Val Pro Gly Gly Val Pro Gly Ala Gly Val Pro Gly Gly Gly
            355                 360                 365
Val Pro Gly Ala Gly Val Pro Gly Gly Val Pro Gly Ala Gly Val
    370                 375                 380
Pro Gly Gly Gly Val Pro Gly Ala Gly Val Pro Gly Gly Val Pro
385             390                 395                 400
Gly Ala Gly Val Pro Gly Val Gly Val Pro Gly Ala Gly Val Pro Gly
                405                 410                 415
Gly Gly Val Pro Gly Ala Gly Val Pro Gly Gly Gly Val Pro Gly Ala
```

```
                420             425             430
Gly Val Pro Gly Gly Val Pro Gly Ala Gly Val Pro Gly Gly
            435             440             445
Val Pro Gly Ala Gly Val Pro Gly Gly Gly Val Pro Gly Ala Gly Val
450             455             460
Pro Gly Gly Gly Val Pro Gly Ala Gly Val Pro Gly Gly Gly Val Pro
465             470             475             480
Gly Ala Gly Val Pro Gly Val Gly Val Pro Gly Ala Gly Val Pro Gly
            485             490             495
Gly Gly Val Pro Gly Ala Gly Val Pro Gly Gly Gly Val Pro Gly Ala
            500             505             510
Gly Val Pro Gly Gly Val Pro Gly Ala Gly Val Pro Gly Gly Gly
            515             520             525
Val Pro Gly Ala Gly Val Pro Gly Gly Gly Val Pro Gly Ala Gly Val
530             535             540
Pro Gly Gly Gly Val Pro Gly Ala Gly Val Pro Gly Gly Gly Val Pro
545             550             555             560
Gly Ala Gly Val Pro Gly Val Gly Val Pro Gly Ala Gly Val Pro Gly
            565             570             575
Gly Gly Val Pro Gly Ala Gly Val Pro Gly Gly Gly Val Pro Gly Ala
            580             585             590
Gly Val Pro Gly Gly Gly Val Pro Gly Ala Gly Val Pro Gly Gly Gly
            595             600             605
Val Pro Gly Ala Gly Val Pro Gly Gly Gly Val Pro Gly Ala Gly Val
610             615             620
Pro Gly Gly Gly Val Pro Gly Ala Gly Val Pro Gly Gly Gly Val Pro
625             630             635             640
Gly Ala Gly Val Pro Gly Val Gly Val Pro Gly Ala Gly Val Pro Gly
            645             650             655
Gly Gly Val Pro Gly Ala Gly Val Pro Gly Gly Gly Val Pro Gly Ala
            660             665             670
Gly Val Pro Gly Gly Gly Val Pro Gly Ala Gly Val Pro Gly Gly Gly
            675             680             685
Val Pro Gly Ala Gly Val Pro Gly Gly Gly Val Pro Gly Ala Gly Val
690             695             700
Pro Gly Gly Gly Val Pro Gly Ala Gly Val Pro Gly Gly Gly Val Pro
705             710             715             720
Gly Ala Gly Val Pro Gly Val Gly Val Pro Gly Ala Gly Val Pro Gly
            725             730             735
Gly Gly Val Pro Gly Ala Gly Val Pro Gly Gly Gly Val Pro Gly Ala
            740             745             750
Gly Val Pro Gly Gly Gly Val Pro Gly Ala Gly Val Pro Gly Gly Gly
            755             760             765
Val Pro Gly Ala Gly Val Pro Gly Gly Gly Val Pro Gly Ala Gly Val
770             775             780
Pro Gly Gly Gly Val Pro Gly Ala Gly Val Pro Gly Gly Gly Val Pro
785             790             795             800
Gly Ala Gly Val Pro Gly Trp Pro Gly Ser Ala Pro Met Ala Glu
            805             810             815
Gly Gly Gly Gln Asn His His Glu Val Val Lys Phe Met Asp Val Tyr
            820             825             830
Gln Arg Ser Tyr Cys His Pro Ile Glu Thr Leu Val Asp Ile Phe Gln
            835             840             845
```

```
Glu Tyr Pro Asp Glu Ile Glu Tyr Ile Phe Lys Pro Ser Cys Val Pro
        850                 855                 860

Leu Met Arg Cys Gly Gly Cys Cys Asn Asp Glu Gly Leu Glu Cys Val
865                 870                 875                 880

Pro Thr Glu Glu Ser Asn Ile Thr Met Gln Ile Met Arg Ile Lys Pro
                885                 890                 895

His Gln Gly Gln His Ile Gly Glu Met Ser Phe Leu Gln His Asn Lys
            900                 905                 910

Cys Glu Cys Arg Pro Lys Lys Asp Arg Ala Arg Gln Glu Lys Cys Asp
        915                 920                 925

Lys Pro Arg Arg
    930

<210> SEQ ID NO 15
<211> LENGTH: 840
<212> TYPE: PRT
<213> ORGANISM: Artificial Sequence
<220> FEATURE:
<223> OTHER INFORMATION: synthetic SynB1-ELP-p50 sequence

<400> SEQUENCE: 15

Met Arg Gly Gly Arg Leu Ser Tyr Ser Arg Arg Phe Ser Thr Ser
1               5                   10                  15

Thr Gly Arg Gly Cys Gly Pro Gly Val Gly Val Pro Gly Ala Gly Val
                20                  25                  30

Pro Gly Gly Gly Val Pro Gly Ala Gly Val Pro Gly Gly Gly Val Pro
            35                  40                  45

Gly Ala Gly Val Pro Gly Gly Gly Val Pro Gly Ala Gly Val Pro Gly
        50                  55                  60

Gly Gly Val Pro Gly Ala Gly Val Pro Gly Gly Gly Val Pro Gly Ala
65                  70                  75                  80

Gly Val Pro Gly Gly Gly Val Pro Gly Ala Gly Val Pro Gly Gly Gly
                85                  90                  95

Val Pro Gly Ala Gly Val Pro Gly Gly Gly Val Pro Gly Ala Gly Val
            100                 105                 110

Pro Gly Gly Gly Val Pro Gly Ala Gly Val Pro Gly Gly Gly Val Pro
        115                 120                 125

Gly Ala Gly Val Pro Gly Gly Gly Val Pro Gly Ala Gly Val Pro Gly
    130                 135                 140

Gly Gly Val Pro Gly Ala Gly Val Pro Gly Gly Gly Val Pro Gly Ala
145                 150                 155                 160

Gly Val Pro Gly Gly Gly Val Pro Gly Ala Gly Val Pro Gly Gly Gly
                165                 170                 175

Val Pro Gly Ala Gly Val Pro Gly Gly Gly Val Pro Gly Ala Gly Val
            180                 185                 190

Pro Gly Gly Gly Val Pro Gly Ala Gly Val Pro Gly Gly Gly Val Pro
        195                 200                 205

Gly Ala Gly Val Pro Gly Gly Gly Val Pro Gly Ala Gly Val Pro Gly
    210                 215                 220

Gly Gly Val Pro Gly Ala Gly Val Pro Gly Gly Gly Val Pro Gly Ala
225                 230                 235                 240

Gly Val Pro Gly Gly Gly Val Pro Gly Ala Gly Val Pro Gly Gly Gly
                245                 250                 255

Val Pro Gly Ala Gly Val Pro Gly Gly Gly Val Pro Gly Ala Gly Val
            260                 265                 270
```

```
Pro Gly Gly Gly Val Pro Gly Ala Gly Val Pro Gly Gly Gly Val Pro
        275                 280                 285
Gly Ala Gly Val Pro Gly Gly Gly Val Pro Gly Ala Gly Val Pro Gly
        290                 295                 300
Gly Gly Val Pro Gly Ala Gly Val Pro Gly Gly Gly Val Pro Gly Ala
305                 310                 315                 320
Gly Val Pro Gly Gly Gly Val Pro Gly Ala Gly Val Pro Gly Gly Gly
                325                 330                 335
Val Pro Gly Ala Gly Val Pro Gly Val Gly Val Pro Gly Ala Gly Val
            340                 345                 350
Pro Gly Gly Gly Val Pro Gly Ala Gly Val Pro Gly Gly Gly Val Pro
        355                 360                 365
Gly Ala Gly Val Pro Gly Gly Gly Val Pro Gly Ala Gly Val Pro Gly
        370                 375                 380
Gly Gly Val Pro Gly Ala Gly Val Pro Gly Gly Gly Val Pro Gly Ala
385                 390                 395                 400
Gly Val Pro Gly Gly Gly Val Pro Gly Ala Gly Val Pro Gly Gly Gly
                405                 410                 415
Val Pro Gly Ala Gly Val Pro Gly Val Gly Val Pro Gly Ala Gly Val
            420                 425                 430
Pro Gly Gly Gly Val Pro Gly Ala Gly Val Pro Gly Gly Gly Val Pro
        435                 440                 445
Gly Ala Gly Val Pro Gly Gly Gly Val Pro Gly Ala Gly Val Pro Gly
        450                 455                 460
Gly Gly Val Pro Gly Ala Gly Val Pro Gly Gly Gly Val Pro Gly Ala
465                 470                 475                 480
Gly Val Pro Gly Gly Gly Val Pro Gly Ala Gly Val Pro Gly Gly Gly
                485                 490                 495
Val Pro Gly Ala Gly Val Pro Gly Val Gly Val Pro Gly Ala Gly Val
            500                 505                 510
Pro Gly Gly Gly Val Pro Gly Ala Gly Val Pro Gly Gly Gly Val Pro
        515                 520                 525
Gly Ala Gly Val Pro Gly Gly Gly Val Pro Gly Ala Gly Val Pro Gly
        530                 535                 540
Gly Gly Val Pro Gly Ala Gly Val Pro Gly Gly Gly Val Pro Gly Ala
545                 550                 555                 560
Gly Val Pro Gly Gly Gly Val Pro Gly Ala Gly Val Pro Gly Gly Gly
                565                 570                 575
Val Pro Gly Ala Gly Val Pro Gly Val Gly Val Pro Gly Ala Gly Val
            580                 585                 590
Pro Gly Gly Gly Val Pro Gly Ala Gly Val Pro Gly Gly Gly Val Pro
        595                 600                 605
Gly Ala Gly Val Pro Gly Gly Gly Val Pro Gly Ala Gly Val Pro Gly
        610                 615                 620
Gly Gly Val Pro Gly Ala Gly Val Pro Gly Gly Gly Val Pro Gly Ala
625                 630                 635                 640
Gly Val Pro Gly Gly Gly Val Pro Gly Ala Gly Val Pro Gly Gly Gly
                645                 650                 655
Val Pro Gly Ala Gly Val Pro Gly Val Gly Val Pro Gly Ala Gly Val
            660                 665                 670
Pro Gly Gly Gly Val Pro Gly Ala Gly Val Pro Gly Gly Gly Val Pro
        675                 680                 685
```

```
Gly Ala Gly Val Pro Gly Gly Val Pro Gly Gly Val Pro Gly
    690                 695                 700
Gly Gly Val Pro Gly Ala Gly Val Pro Gly Gly Val Pro Gly Ala
705                 710                 715                 720
Gly Val Pro Gly Gly Val Pro Gly Ala Gly Val Pro Gly Gly
                725                 730                 735
Val Pro Gly Ala Gly Val Pro Gly Val Gly Val Pro Gly Ala Gly Val
            740                 745                 750
Pro Gly Gly Gly Val Pro Gly Ala Gly Val Pro Gly Gly Gly Val Pro
        755                 760                 765
Gly Ala Gly Val Pro Gly Gly Val Pro Gly Ala Gly Val Pro Gly
    770                 775                 780
Gly Gly Val Pro Gly Ala Gly Val Pro Gly Gly Val Pro Gly Ala
785                 790                 795                 800
Gly Val Pro Gly Gly Val Pro Gly Ala Gly Val Pro Gly Gly Gly
                805                 810                 815
Val Pro Gly Ala Gly Val Pro Gly Trp Pro Gly Ser Gly Gly Val Gln
            820                 825                 830
Arg Lys Arg Gln Lys Leu Met Pro
        835                 840

<210> SEQ ID NO 16
<211> LENGTH: 839
<212> TYPE: PRT
<213> ORGANISM: Artificial Sequence
<220> FEATURE:
<223> OTHER INFORMATION: synthetic SynB1-ELP-NOX sequence

<400> SEQUENCE: 16

Met Arg Gly Gly Arg Leu Ser Tyr Ser Arg Arg Phe Ser Thr Ser
1               5                   10                  15
Thr Gly Arg Gly Cys Gly Pro Gly Val Gly Val Pro Gly Ala Gly Val
            20                  25                  30
Pro Gly Gly Gly Val Pro Gly Ala Gly Val Pro Gly Gly Gly Val Pro
        35                  40                  45
Gly Ala Gly Val Pro Gly Gly Val Pro Gly Ala Gly Val Pro Gly
    50                  55                  60
Gly Gly Val Pro Gly Ala Gly Val Pro Gly Gly Val Pro Gly Ala
65                  70                  75                  80
Gly Val Pro Gly Gly Val Pro Gly Ala Gly Val Pro Gly Gly Gly
                85                  90                  95
Val Pro Gly Ala Gly Val Pro Gly Val Gly Val Pro Gly Ala Gly Val
            100                 105                 110
Pro Gly Gly Gly Val Pro Gly Ala Gly Val Pro Gly Gly Gly Val Pro
        115                 120                 125
Gly Ala Gly Val Pro Gly Gly Val Pro Gly Ala Gly Val Pro Gly
    130                 135                 140
Gly Gly Val Pro Gly Ala Gly Val Pro Gly Gly Val Pro Gly Ala
145                 150                 155                 160
Gly Val Pro Gly Gly Val Pro Gly Ala Gly Val Pro Gly Gly Gly
                165                 170                 175
Val Pro Gly Ala Gly Val Pro Gly Val Gly Val Pro Gly Ala Gly Val
            180                 185                 190
Pro Gly Gly Gly Val Pro Gly Ala Gly Val Pro Gly Gly Gly Val Pro
        195                 200                 205
```

```
Gly Ala Gly Val Pro Gly Gly Val Pro Gly Ala Gly Val Pro Gly
    210                 215                 220
Gly Gly Val Pro Gly Ala Gly Val Pro Gly Gly Gly Val Pro Gly Ala
225                 230                 235                 240
Gly Val Pro Gly Gly Gly Val Pro Gly Ala Gly Val Pro Gly Gly Gly
                245                 250                 255
Val Pro Gly Ala Gly Val Pro Gly Val Gly Val Pro Gly Ala Gly Val
            260                 265                 270
Pro Gly Gly Gly Val Pro Gly Ala Gly Val Pro Gly Gly Gly Val Pro
        275                 280                 285
Gly Ala Gly Val Pro Gly Gly Val Pro Gly Ala Gly Val Pro Gly
    290                 295                 300
Gly Gly Val Pro Gly Ala Gly Val Pro Gly Gly Gly Val Pro Gly Ala
305                 310                 315                 320
Gly Val Pro Gly Gly Gly Val Pro Gly Ala Gly Val Pro Gly Gly Gly
                325                 330                 335
Val Pro Gly Ala Gly Val Pro Gly Val Gly Val Pro Gly Ala Gly Val
            340                 345                 350
Pro Gly Gly Gly Val Pro Gly Ala Gly Val Pro Gly Gly Gly Val Pro
        355                 360                 365
Gly Ala Gly Val Pro Gly Gly Val Pro Gly Ala Gly Val Pro Gly
    370                 375                 380
Gly Gly Val Pro Gly Ala Gly Val Pro Gly Gly Gly Val Pro Gly Ala
385                 390                 395                 400
Gly Val Pro Gly Gly Gly Val Pro Gly Ala Gly Val Pro Gly Gly Gly
                405                 410                 415
Val Pro Gly Ala Gly Val Pro Gly Val Gly Val Pro Gly Ala Gly Val
            420                 425                 430
Pro Gly Gly Gly Val Pro Gly Ala Gly Val Pro Gly Gly Gly Val Pro
        435                 440                 445
Gly Ala Gly Val Pro Gly Gly Val Pro Gly Ala Gly Val Pro Gly
    450                 455                 460
Gly Gly Val Pro Gly Ala Gly Val Pro Gly Gly Gly Val Pro Gly Ala
465                 470                 475                 480
Gly Val Pro Gly Gly Gly Val Pro Gly Ala Gly Val Pro Gly Gly Gly
                485                 490                 495
Val Pro Gly Ala Gly Val Pro Gly Val Gly Val Pro Gly Ala Gly Val
            500                 505                 510
Pro Gly Gly Gly Val Pro Gly Ala Gly Val Pro Gly Gly Gly Val Pro
        515                 520                 525
Gly Ala Gly Val Pro Gly Gly Val Pro Gly Ala Gly Val Pro Gly
    530                 535                 540
Gly Gly Val Pro Gly Ala Gly Val Pro Gly Gly Gly Val Pro Gly Ala
545                 550                 555                 560
Gly Val Pro Gly Gly Gly Val Pro Gly Ala Gly Val Pro Gly Gly Gly
                565                 570                 575
Val Pro Gly Ala Gly Val Pro Gly Val Gly Val Pro Gly Ala Gly Val
            580                 585                 590
Pro Gly Gly Gly Val Pro Gly Ala Gly Val Pro Gly Gly Gly Val Pro
        595                 600                 605
Gly Ala Gly Val Pro Gly Gly Val Pro Gly Ala Gly Val Pro Gly
    610                 615                 620
Gly Gly Val Pro Gly Ala Gly Val Pro Gly Gly Gly Val Pro Gly Ala
```

-continued

```
            625                 630                 635                 640
Gly Val Pro Gly Gly Val Pro Gly Ala Gly Val Pro Gly Gly Gly
                    645                 650                 655
Val Pro Gly Ala Gly Val Pro Gly Val Gly Val Pro Gly Ala Gly Val
                660                 665                 670
Pro Gly Gly Gly Val Pro Gly Ala Gly Val Pro Gly Gly Gly Val Pro
            675                 680                 685
Gly Ala Gly Val Pro Gly Gly Val Pro Gly Ala Gly Val Pro Gly
        690                 695                 700
Gly Gly Val Pro Gly Ala Gly Val Pro Gly Gly Gly Val Pro Gly Ala
705                 710                 715                 720
Gly Val Pro Gly Gly Gly Val Pro Gly Ala Gly Val Pro Gly Gly Gly
                    725                 730                 735
Val Pro Gly Ala Gly Val Pro Gly Val Gly Val Pro Gly Ala Gly Val
                740                 745                 750
Pro Gly Gly Gly Val Pro Gly Ala Gly Val Pro Gly Gly Gly Val Pro
            755                 760                 765
Gly Ala Gly Val Pro Gly Gly Gly Val Pro Gly Ala Gly Val Pro Gly
    770                 775                 780
Gly Gly Val Pro Gly Ala Gly Val Pro Gly Gly Gly Val Pro Gly Ala
785                 790                 795                 800
Gly Val Pro Gly Gly Gly Val Pro Gly Ala Gly Val Pro Gly Gly Gly
                    805                 810                 815
Val Pro Gly Ala Gly Val Pro Gly Trp Pro Gly Ser Gly Gly Cys Ser
                820                 825                 830
Thr Arg Ile Arg Arg Gln Leu
            835
```